United States Patent
Hofstadler et al.

(10) Patent No.: US 7,964,343 B2
(45) Date of Patent: Jun. 21, 2011

(54) METHOD FOR RAPID PURIFICATION OF NUCLEIC ACIDS FOR SUBSEQUENT ANALYSIS BY MASS SPECTROMETRY BY SOLUTION CAPTURE

(75) Inventors: Steven A. Hofstadler, Oceanside, CA (US); Lendell L. Cummins, San Diego, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 903 days.

(21) Appl. No.: 10/844,938

(22) Filed: May 12, 2004

(65) Prior Publication Data

US 2005/0164215 A1 Jul. 28, 2005

Related U.S. Application Data

(60) Provisional application No. 60/470,547, filed on May 13, 2003.

(51) Int. Cl.
*C12Q 1/68* (2006.01)
*C07H 21/04* (2006.01)

(52) U.S. Cl. ......................................... 435/6; 536/23.1

(58) Field of Classification Search ........ 435/6; 536/23.1
See application file for complete search history.

(56) References Cited

U.S. PATENT DOCUMENTS

| | | | |
|---|---|---|---|
| 4,075,475 A | 2/1978 | Risby et al. | |
| 4,683,195 A | 7/1987 | Mullis et al. | |
| 4,683,202 A | 7/1987 | Mullis | |
| 4,965,188 A | 10/1990 | Mullis et al. | |
| 5,015,845 A | 5/1991 | Allen et al. | |
| 5,072,115 A | 12/1991 | Zhou | |
| 5,143,905 A | 9/1992 | Sivasubramanian et al. | |
| 5,213,961 A | 5/1993 | Bunn et al. | |
| 5,219,727 A | 6/1993 | Wang et al. | |
| 5,288,611 A | 2/1994 | Kohne | |
| 5,436,129 A | 7/1995 | Stapleton | |
| 5,451,500 A | 9/1995 | Stapleton | |
| 5,472,843 A | 12/1995 | Milliman | |
| 5,476,774 A | 12/1995 | Wang et al. | |
| 5,484,808 A | 1/1996 | Grinnell | |
| 5,484,908 A | 1/1996 | Froehler et al. | |
| 5,502,177 A | 3/1996 | Matteucci et al. | |
| 5,503,980 A | 4/1996 | Cantor | |

(Continued)

FOREIGN PATENT DOCUMENTS

AU 2003282352 11/2002

(Continued)

OTHER PUBLICATIONS

Jiang et al. A highly efficient and automated method for purifying and desalting PCR products for analysis by electrospray ionization mass spectrometry, Analytical Biochemistry, vol. 316, p. 50-57, May 1, 2003.*

(Continued)

*Primary Examiner* — Suryaprabha Chunduru
(74) *Attorney, Agent, or Firm* — Casimir Jones S.C.; Christopher C. Sappenfield

(57) ABSTRACT

The present invention provides a method for rapid solution capture purification of nucleic acids for subsequent analysis by electrospray mass spectrometry which is efficient and cost-effective relative to existing methods. The present invention also provides kits useful for practicing rapid solution capture of nucleic acids so that purified samples are in condition for analysis by electrospray mass spectrometry.

24 Claims, 2 Drawing Sheets

U.S. PATENT DOCUMENTS

| | | | |
|---|---|---|---|
| 5,504,327 | A | 4/1996 | Sproch et al. |
| 5,504,329 | A | 4/1996 | Mann et al. |
| 5,523,217 | A | 6/1996 | Lupski et al. |
| 5,527,669 | A | 6/1996 | Resnick et al. |
| 5,527,675 | A | 6/1996 | Coull et al. |
| 5,527,875 | A | 6/1996 | Yokoyama et al. |
| 5,547,835 | A | 8/1996 | Koster |
| 5,567,587 | A | 10/1996 | Kohne |
| 5,576,204 | A | 11/1996 | Blanco et al. |
| 5,580,733 | A | 12/1996 | Levis et al. |
| 5,605,798 | A | 2/1997 | Koster |
| 5,608,217 | A | 3/1997 | Franzen et al. |
| 5,612,179 | A | 3/1997 | Simons |
| 5,622,824 | A | 4/1997 | K oster |
| 5,625,184 | A | 4/1997 | Vestal et al. |
| 5,639,606 | A | 6/1997 | Willey |
| 5,641,632 | A | 6/1997 | Kohne |
| 5,645,985 | A | 7/1997 | Froehler et al. |
| 5,683,869 | A | 11/1997 | Ramsay Shaw et al. |
| 5,686,242 | A | 11/1997 | Bruice et al. |
| 5,691,141 | A | 11/1997 | Koster |
| 5,700,642 | A | 12/1997 | Monforte et al. |
| 5,702,895 | A | 12/1997 | Matsunaga et al. |
| 5,707,802 | A | 1/1998 | Sandhu et al. |
| 5,712,125 | A | 1/1998 | Uhlen |
| 5,716,825 | A | 2/1998 | Hancock et al. |
| 5,727,202 | A | 3/1998 | Kucala |
| 5,745,751 | A | 4/1998 | Nelson et al. |
| 5,747,246 | A | 5/1998 | Pannetier et al. |
| 5,747,251 | A | 5/1998 | Carson et al. |
| 5,753,467 | A | 5/1998 | Jensen et al. |
| 5,753,489 | A | 5/1998 | Kistner et al. |
| 5,759,771 | A | 6/1998 | Tilanus |
| 5,763,169 | A | 6/1998 | Sandhu et al. |
| 5,763,588 | A | 6/1998 | Matteucci et al. |
| 5,770,367 | A | 6/1998 | Southern et al. |
| 5,777,324 | A | 7/1998 | Hillenkamp |
| 5,814,442 | A | 9/1998 | Natarajan et al. |
| 5,822,824 | A | 10/1998 | Dion |
| 5,828,062 | A | 10/1998 | Jarrell et al. |
| 5,830,653 | A | 11/1998 | Froehler et al. |
| 5,830,655 | A | 11/1998 | Monforte et al. |
| 5,830,853 | A | 11/1998 | Backstrom et al. |
| 5,832,489 | A | 11/1998 | Kucala |
| 5,834,255 | A | 11/1998 | Van Gemen et al. |
| 5,845,174 | A | 12/1998 | Yasui et al. |
| 5,849,492 | A | 12/1998 | Rogan |
| 5,849,497 | A | 12/1998 | Steinman |
| 5,849,901 | A | 12/1998 | Mabilat et al. |
| 5,851,765 | A | 12/1998 | Koster |
| 5,856,174 | A | 1/1999 | Lipshutz et al. |
| 5,864,137 | A | 1/1999 | Becker et al. |
| 5,866,429 | A * | 2/1999 | Bloch ............................ 436/94 |
| 5,869,242 | A | 2/1999 | Kamb |
| 5,871,697 | A | 2/1999 | Rothberg et al. |
| 5,872,003 | A | 2/1999 | Koster |
| 5,876,936 | A | 3/1999 | Ju |
| 5,876,938 | A | 3/1999 | Stolowitz et al. |
| 5,885,775 | A | 3/1999 | Haff et al. |
| 5,900,481 | A | 5/1999 | Lough et al. |
| 5,928,905 | A | 7/1999 | Stemmer et al. |
| 5,928,906 | A | 7/1999 | Koster et al. |
| 5,965,363 | A | 10/1999 | Monforte et al. |
| 5,965,383 | A | 10/1999 | Vogel et al. |
| 5,972,693 | A | 10/1999 | Rothberg et al. |
| 5,976,798 | A | 11/1999 | Parker et al. |
| 5,981,176 | A | 11/1999 | Wallace |
| 5,981,178 | A | 11/1999 | Tsui et al. |
| 5,981,190 | A | 11/1999 | Israel |
| 5,994,066 | A | 11/1999 | Bergeron et al. |
| 6,001,564 | A | 12/1999 | Bergeron et al. |
| 6,001,584 | A | 12/1999 | Karin et al. |
| 6,005,096 | A | 12/1999 | Matteucci et al. |
| 6,007,690 | A | 12/1999 | Nelson et al. |
| 6,007,992 | A | 12/1999 | Lin et al. |
| 6,015,666 | A | 1/2000 | Springer et al. |
| 6,018,713 | A | 1/2000 | Coli et al. |
| 6,024,925 | A | 2/2000 | Little et al. |
| 6,028,183 | A | 2/2000 | Lin et al. |
| 6,043,031 | A | 3/2000 | Koster et al. |
| 6,046,005 | A | 4/2000 | Ju et al. |
| 6,051,378 | A | 4/2000 | Monforte et al. |
| 6,054,278 | A | 4/2000 | Dodge et al. |
| 6,055,487 | A | 4/2000 | Margery et al. |
| 6,060,246 | A | 5/2000 | Summerton et al. |
| 6,061,686 | A | 5/2000 | Gauvin et al. |
| 6,063,031 | A | 5/2000 | Cundari et al. |
| 6,074,823 | A | 6/2000 | Koster |
| 6,074,831 | A | 6/2000 | Yakhini et al. |
| 6,090,558 | A | 7/2000 | Butler et al. |
| 6,104,028 | A | 8/2000 | Hunter et al. |
| 6,110,710 | A | 8/2000 | Smith et al. |
| 6,111,251 | A | 8/2000 | Hillenkamp |
| 6,133,436 | A | 10/2000 | Koster et al. |
| 6,140,053 | A | 10/2000 | Koster |
| 6,146,144 | A | 11/2000 | Fowler et al. |
| 6,146,854 | A | 11/2000 | Koster et al. |
| 6,153,389 | A | 11/2000 | Haarer et al. |
| 6,159,681 | A | 12/2000 | Zebala |
| 6,180,339 | B1 | 1/2001 | Sandhu et al. |
| 6,180,372 | B1 | 1/2001 | Franzen |
| 6,187,842 | B1 | 2/2001 | Kobayashi et al. |
| 6,194,144 | B1 | 2/2001 | Koster |
| 6,197,498 | B1 | 3/2001 | Koster |
| 6,214,555 | B1 | 4/2001 | Leushner et al. |
| 6,218,118 | B1 | 4/2001 | Sampson et al. |
| 6,221,587 | B1 | 4/2001 | Ecker et al. |
| 6,221,598 | B1 | 4/2001 | Schumm et al. |
| 6,221,601 | B1 | 4/2001 | Koster et al. |
| 6,221,605 | B1 | 4/2001 | Koster |
| 6,225,450 | B1 | 5/2001 | Koster |
| 6,227,634 | B1 | 5/2001 | Cittadini et al. |
| 6,235,476 | B1 | 5/2001 | Bergmann et al. |
| 6,235,478 | B1 | 5/2001 | Koster |
| 6,235,480 | B1 | 5/2001 | Shultz et al. |
| 6,238,871 | B1 | 5/2001 | Koster |
| 6,238,927 | B1 | 5/2001 | Abrams et al. |
| 6,239,159 | B1 | 5/2001 | Brown et al. |
| 6,258,538 | B1 | 7/2001 | Koster et al. |
| 6,261,769 | B1 | 7/2001 | Everett et al. |
| 6,265,716 | B1 | 7/2001 | Hunter et al. |
| 6,265,718 | B1 | 7/2001 | Park, II et al. |
| 6,266,131 | B1 | 7/2001 | Hamada et al. |
| 6,266,144 | B1 | 7/2001 | Li |
| 6,268,129 | B1 | 7/2001 | Gut et al. |
| 6,268,131 | B1 | 7/2001 | Kang et al. |
| 6,268,144 | B1 | 7/2001 | Koster |
| 6,268,146 | B1 | 7/2001 | Shultz et al. |
| 6,270,973 | B1 | 8/2001 | Lewis et al. |
| 6,270,974 | B1 | 8/2001 | Shultz et al. |
| 6,274,726 | B1 | 8/2001 | Laugharn, Jr. et al. |
| 6,277,573 | B1 | 8/2001 | Koster |
| 6,277,578 | B1 | 8/2001 | Shultz et al. |
| 6,277,634 | B1 | 8/2001 | McCall et al. |
| 6,286,146 | B1 | 9/2001 | Rocker |
| 6,288,148 | B1 | 9/2001 | Samukawa et al. |
| 6,300,076 | B1 | 10/2001 | Koster |
| 6,303,297 | B1 | 10/2001 | Lincoln et al. |
| 6,312,893 | B1 | 11/2001 | Van Ness et al. |
| 6,312,902 | B1 | 11/2001 | Shultz et al. |
| 6,322,970 | B1 | 11/2001 | Little et al. |
| 6,361,940 | B1 | 3/2002 | Van Ness et al. |
| 6,372,424 | B1 | 4/2002 | Brow et al. |
| 6,389,428 | B1 | 5/2002 | Rigault et al. |
| 6,391,551 | B1 | 5/2002 | Shultz et al. |
| 6,393,367 | B1 | 5/2002 | Tang et al. |
| 6,419,932 | B1 | 7/2002 | Dale |
| 6,423,966 | B2 | 7/2002 | Hillenkamp et al. |
| 6,428,955 | B1 | 8/2002 | Koster et al. |
| 6,428,956 | B1 | 8/2002 | Crooke et al. |
| 6,432,651 | B1 | 8/2002 | Hughes et al. |
| 6,436,635 | B1 | 8/2002 | Fu et al. |
| 6,436,640 | B1 | 8/2002 | Simmons et al. |
| 6,453,244 | B1 | 9/2002 | Oefner |
| 6,458,533 | B1 | 10/2002 | Felder et al. |
| 6,468,743 | B1 | 10/2002 | Romick et al. |
| 6,468,748 | B1 | 10/2002 | Monforte et al. |

| Patent No. | Date | Inventor |
|---|---|---|
| 6,475,143 B2 | 11/2002 | Iliff |
| 6,475,736 B1 | 11/2002 | Stanton, Jr. |
| 6,475,738 B2 | 11/2002 | Shuber et al. |
| 6,479,239 B1 | 11/2002 | Anderson et al. |
| 6,500,621 B2 | 12/2002 | Koster |
| 6,533,317 B2 | 3/2003 | Kath |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton, Jr. et al. |
| 6,613,509 B1 | 9/2003 | Chen |
| 6,613,520 B2 | 9/2003 | Ashby |
| 6,623,928 B2 | 9/2003 | Van Ness et al. |
| 6,638,714 B1 | 10/2003 | Linnen et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,716,634 B1 | 4/2004 | Myerson |
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 * | 7/2005 | Baker .......... 536/25.4 |
| 6,977,148 B2 | 12/2005 | Dean et al. |
| 6,994,962 B1 | 2/2006 | Thilly |
| 7,022,835 B1 * | 4/2006 | Rauth et al. .......... 536/25.4 |
| 7,024,370 B2 | 4/2006 | Epler et al. |
| 7,108,974 B2 | 9/2006 | Ecker et al. |
| 7,198,893 B1 | 4/2007 | Köster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Köster |
| 7,501,251 B2 | 3/2009 | Köster et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 2001/0039263 A1 | 11/2001 | Matthes et al. |
| 2002/0006611 A1 | 1/2002 | Portugal et al. |
| 2002/0042112 A1 | 4/2002 | Koster et al. |
| 2002/0042506 A1 * | 4/2002 | Kristyanne et al. .......... 536/25.4 |
| 2002/0045178 A1 | 4/2002 | Cantor et al. |
| 2002/0055101 A1 | 5/2002 | Bergeron et al. |
| 2002/0090320 A1 | 7/2002 | Burow et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150903 A1 | 10/2002 | Koster |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0082539 A1 | 5/2003 | Ecker et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0124556 A1 | 7/2003 | Ecker et al. |
| 2003/0129589 A1 | 7/2003 | Koster et al. |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0187615 A1 | 10/2003 | Epler et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0006611 A1 | 1/2004 | Yi |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0161770 A1 | 8/2004 | Ecker et al. |
| 2004/0180328 A1 | 9/2004 | Ecker et al. |
| 2004/0185438 A1 | 9/2004 | Ecker |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0219517 A1 | 11/2004 | Ecker et al. |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130196 A1 | 6/2005 | Hofstadler et al. |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler et al. |

| | | | |
|---|---|---|---|
| 2006/0020391 A1 | 1/2006 | Kreiswirth et al. | |
| 2006/0057605 A1 | 3/2006 | Sampath et al. | |
| 2006/0121520 A1 | 6/2006 | Ecker et al. | |
| 2006/0172330 A1 | 8/2006 | Osborn et al. | |
| 2006/0205040 A1 | 9/2006 | Sampath | |
| 2006/0240412 A1 | 10/2006 | Hall et al. | |
| 2006/0259249 A1 | 11/2006 | Sampath et al. | |
| 2006/0275788 A1 | 12/2006 | Ecker et al. | |
| 2007/0048735 A1 | 3/2007 | Ecker et al. | |
| 2007/0218467 A1 | 9/2007 | Ecker et al. | |
| 2008/0160512 A1 | 7/2008 | Ecker et al. | |
| 2008/0311558 A1 | 12/2008 | Ecker et al. | |
| 2009/0004643 A1 | 1/2009 | Ecker et al. | |
| 2009/0023150 A1 | 1/2009 | Koster et al. | |
| 2009/0042203 A1 | 2/2009 | Koster | |
| 2009/0092977 A1 | 4/2009 | Koster | |
| 2009/0125245 A1 | 5/2009 | Hofstadler et al. | |
| 2009/0148829 A1 | 6/2009 | Ecker et al. | |
| 2009/0148836 A1 | 6/2009 | Ecker et al. | |
| 2009/0148837 A1 | 6/2009 | Ecker et al. | |
| 2009/0182511 A1 | 7/2009 | Ecker et al. | |
| 2009/0239224 A1 | 9/2009 | Ecker et al. | |
| 2009/0280471 A1 | 11/2009 | Ecker et al. | |
| 2010/0070194 A1 | 3/2010 | Ecker et al. | |
| 2010/0145626 A1 | 6/2010 | Ecker et al. | |
| 2010/0184035 A1 | 7/2010 | Hall et al. | |

FOREIGN PATENT DOCUMENTS

| | | | |
|---|---|---|---|
| AU | 3245488 A | 12/2003 | |
| AU | 3302236 A | 6/2004 | |
| AU | 2003298030 A | 6/2004 | |
| AU | 3297687 A | 7/2004 | |
| AU | 2244250 B | 11/2006 | |
| AU | 6272776 A | 2/2007 | |
| AU | 10200686 A | 3/2010 | |
| CA | 2439655 A | 9/2002 | |
| CA | 2508584 A | 6/2004 | |
| CA | 2510007 A | 6/2004 | |
| CA | 2508726 A | 7/2004 | |
| CA | 2616281 A | 2/2007 | |
| CN | 1202204 A | 12/1998 | |
| DE | 19732086 A1 | 1/1999 | |
| DE | 19802905 A1 | 7/1999 | |
| DE | 19824280 A1 | 12/1999 | |
| DE | 19852167 A1 | 5/2000 | |
| DE | 19943374 A1 | 3/2001 | |
| DE | 10132147 B4 | 2/2003 | |
| EP | 281390 A2 | 9/1988 | |
| EP | 633321 A1 | 1/1995 | |
| EP | 620862 B1 | 4/1998 | |
| EP | 1035219 A1 | 9/2000 | |
| EP | 1138782 A2 | 10/2001 | |
| EP | 1234888 A2 | 8/2002 | |
| EP | 1138782 A3 | 2/2003 | |
| EP | 1308506 A1 | 5/2003 | |
| EP | 1310571 A2 | 5/2003 | |
| EP | 1333101 A1 | 8/2003 | |
| EP | 1364064 A2 | 11/2003 | |
| EP | 1365031 A1 | 11/2003 | |
| EP | 1234888 A3 | 1/2004 | |
| EP | 1573065 A2 | 9/2005 | |
| EP | 1578399 A2 | 9/2005 | |
| EP | 1581657 A2 | 10/2005 | |
| EP | 1748072 A1 | 1/2007 | |
| EP | 1904655 A2 | 4/2008 | |
| EP | 2126132 A2 | 8/2008 | |
| FR | 2811321 A1 | 1/2002 | |
| GB | 2325002 A | 11/1998 | |
| GB | 2339905 A | 2/2000 | |
| IL | 157661 | 3/2004 | |
| JP | 5276999 A2 | 10/1993 | |
| JP | 11137259 A | 5/1999 | |
| JP | 2002541839 T2 | 12/2002 | |
| JP | 2004200 A2 | 1/2004 | |
| JP | 24024206 A2 | 1/2004 | |
| JP | 24201641 A2 | 7/2004 | |
| JP | 24201679 A2 | 7/2004 | |
| JP | 25504508 T2 | 2/2005 | |
| JP | 26516193 T2 | 6/2006 | |
| JP | 29502137 T2 | 1/2009 | |
| JP | 2009245976 | 10/2009 | |
| MX | 3007927 A | 10/2004 | |
| NZ | 527857 A | 8/2005 | |
| PH | 1-2003-500824 | 9/2008 | |
| RU | 3129269 A | 4/2005 | |
| SG | 98824 | 12/2005 | |
| WO | WO8803957 A1 | 6/1988 | |
| WO | WO9015157 A1 | 12/1990 | |
| WO | WO9205182 A1 | 4/1992 | |
| WO | WO9208117 A1 | 5/1992 | |
| WO | WO9209703 A1 | 6/1992 | |
| WO | WO9219774 A1 | 11/1992 | |
| WO | WO9303186 A1 | 2/1993 | |
| WO | WO9305182 A1 | 3/1993 | |
| WO | WO9308297 A1 | 4/1993 | |
| WO | WO 9411103 A1 | * | 5/1994 |
| WO | WO9416101 A2 | 7/1994 | |
| WO | WO9419490 A1 | 9/1994 | |
| WO | WO9421822 A1 | 9/1994 | |
| WO | WO9504161 A1 | 2/1995 | |
| WO | WO9511996 A1 | 5/1995 | |
| WO | WO9513395 A1 | 5/1995 | |
| WO | WO9513396 A2 | 5/1995 | |
| WO | WO9531997 A1 | 11/1995 | |
| WO | WO9603763 A1 | 2/1996 | |
| WO | WO9606187 A1 | 2/1996 | |
| WO | WO9616186 A1 | 5/1996 | |
| WO | WO9629431 A2 | 9/1996 | |
| WO | WO9632504 A2 | 10/1996 | |
| WO | WO9635450 A1 | 11/1996 | |
| WO | WO9637630 A1 | 11/1996 | |
| WO | WO9733000 A1 | 9/1997 | |
| WO | WO9734909 A1 | 9/1997 | |
| WO | WO9737041 A2 | 10/1997 | |
| WO | WO9747766 A1 | 12/1997 | |
| WO | WO9803684 A1 | 1/1998 | |
| WO | WO9812355 A1 | 3/1998 | |
| WO | WO9814616 A1 | 4/1998 | |
| WO | WO9815652 A1 | 4/1998 | |
| WO | WO9820020 A2 | 5/1998 | |
| WO | WO9820157 A2 | 5/1998 | |
| WO | WO9820166 A2 | 5/1998 | |
| WO | WO9826095 A1 | 6/1998 | |
| WO | WO9831830 A1 | 7/1998 | |
| WO | WO9835057 A1 | 8/1998 | |
| WO | WO9840520 A1 | 9/1998 | |
| WO | WO9854571 A1 | 12/1998 | |
| WO | WO9854751 A1 | 12/1998 | |
| WO | WO9905319 A2 | 2/1999 | |
| WO | WO9912040 A2 | 3/1999 | |
| WO | WO9913104 A1 | 3/1999 | |
| WO | WO9914375 A2 | 3/1999 | |
| WO | WO9929898 A2 | 6/1999 | |
| WO | WO9931278 A1 | 6/1999 | |
| WO | WO9957318 A2 | 11/1999 | |
| WO | WO9958713 A2 | 11/1999 | |
| WO | WO9960183 A1 | 11/1999 | |
| WO | WO0032750 A1 | 6/2000 | |
| WO | WO0038636 A1 | 7/2000 | |
| WO | WO0063362 A1 | 10/2000 | |
| WO | WO0066789 A2 | 11/2000 | |
| WO | WO0077260 A1 | 12/2000 | |
| WO | WO0100828 A2 | 1/2001 | |
| WO | WO0107648 A1 | 2/2001 | |
| WO | WO0112853 A1 | 2/2001 | |
| WO | WO0123604 A2 | 4/2001 | |
| WO | WO0123608 A2 | 4/2001 | |
| WO | WO0132930 A1 | 5/2001 | |
| WO | WO0140497 A2 | 6/2001 | |
| WO | WO0146404 A1 | 6/2001 | |
| WO | WO0151661 A2 | 7/2001 | |
| WO | WO0151662 A1 | 7/2001 | |
| WO | WO0157263 A1 | 8/2001 | |
| WO | WO0157518 A2 | 8/2001 | |
| WO | WO0173119 A2 | 10/2001 | |
| WO | WO0173199 A1 | 10/2001 | |
| WO | WO0177392 A2 | 10/2001 | |
| WO | WO0196388 A2 | 12/2001 | |

| WO | WO0202811 A2 | 1/2002 |
| WO | WO0210186 A1 | 2/2002 |
| WO | WO0210444 A1 | 2/2002 |
| WO | WO0218641 A2 | 3/2002 |
| WO | WO0221108 A2 | 3/2002 |
| WO | WO0222873 A1 | 3/2002 |
| WO | WO0224876 A2 | 3/2002 |
| WO | WO0250307 A1 | 6/2002 |
| WO | WO02057491 A2 | 7/2002 |
| WO | WO02070664 A2 | 9/2002 |
| WO | WO02070728 A2 | 9/2002 |
| WO | WO02070737 A2 | 9/2002 |
| WO | WO02077278 A1 | 10/2002 |
| WO | WO02099034 A2 | 12/2002 |
| WO | WO02099095 A2 | 12/2002 |
| WO | WO02099129 A2 | 12/2002 |
| WO | WO02099130 A2 | 12/2002 |
| WO | WO03001976 A2 | 1/2003 |
| WO | WO03002750 A2 | 1/2003 |
| WO | WO03008636 A2 | 1/2003 |
| WO | WO03012058 A2 | 2/2003 |
| WO | WO03012074 A2 | 2/2003 |
| WO | WO03014382 A2 | 2/2003 |
| WO | WO03016546 A1 | 2/2003 |
| WO | WO03018636 A2 | 3/2003 |
| WO | WO03020890 A2 | 3/2003 |
| WO | WO03033732 A2 | 4/2003 |
| WO | WO03054162 A2 | 7/2003 |
| WO | WO03054755 A2 | 7/2003 |
| WO | WO03060163 A2 | 7/2003 |
| WO | WO03075955 A1 | 9/2003 |
| WO | WO03088979 A2 | 10/2003 |
| WO | WO03093506 A2 | 11/2003 |
| WO | WO03097869 A2 | 11/2003 |
| WO | WO03100035 A2 | 12/2003 |
| WO | WO03100068 A1 | 12/2003 |
| WO | WO03102191 A1 | 12/2003 |
| WO | WO03104410 A2 | 12/2003 |
| WO | WO03106635 A2 | 12/2003 |
| WO | WO2004003511 A2 | 1/2004 |
| WO | WO2004009849 A1 | 1/2004 |
| WO | WO2004011651 A1 | 2/2004 |
| WO | WO2004013357 A2 | 2/2004 |
| WO | WO2004040013 A1 | 5/2004 |
| WO | WO2004044123 A2 | 5/2004 |
| WO | WO2004044247 A2 | 5/2004 |
| WO | WO2004052175 A2 | 6/2004 |
| WO | WO2004052175 A3 | 6/2004 |
| WO | WO2004053076 A2 | 6/2004 |
| WO | WO2004053141 A2 | 6/2004 |
| WO | WO2004053164 A1 | 6/2004 |
| WO | WO2004060278 A2 | 7/2004 |
| WO | WO2004070001 A2 | 8/2004 |
| WO | WO2004072230 A2 | 8/2004 |
| WO | WO2004072231 A2 | 8/2004 |
| WO | WO2004101809 A2 | 11/2004 |
| WO | WO2005003384 A1 | 1/2005 |
| WO | WO2005009202 A2 | 2/2005 |
| WO | WO2005012572 A1 | 2/2005 |
| WO | WO2005024046 A2 | 3/2005 |
| WO | WO2005036369 A2 | 4/2005 |
| WO | WO2005053141 A1 | 6/2005 |
| WO | WO2005054454 A1 | 6/2005 |
| WO | WO2005075686 A1 | 8/2005 |
| WO | WO2005086634 A2 | 9/2005 |
| WO | WO2005091971 A2 | 10/2005 |
| WO | WO2005098047 A2 | 10/2005 |
| WO | WO2005116263 A2 | 12/2005 |
| WO | WO2006089762 A1 | 8/2006 |
| WO | WO2006094238 A2 | 9/2006 |
| WO | WO2006116127 A2 | 11/2006 |
| WO | WO2006135400 A2 | 12/2006 |
| WO | WO2007014045 A2 | 2/2007 |
| WO | WO2007086904 A2 | 8/2007 |
| WO | WO2008104002 A2 | 8/2008 |
| WO | WO2008118809 A1 | 10/2008 |
| ZA | 306810 A | 9/2004 |

OTHER PUBLICATIONS

Smirnov et al. Application of DNA-binding polymers for preparation of DNA for analysis by matrix-assisted laser desorption/ionization mass spectrometry. Rapid Comm in Mass Spectrometry, vol. 15, p. 1427-1432, 2001.*

Jiang et al. A highly efficient and automated method for purifying and desalting PCR products for analysis by electrospray ionization mass spectrometry, Analytical Biochemistry, vol. 316, p. 50-57, May 1, 2003.*

U.S. Appl. No. 10/326,047, filed Dec. 18, 2002, Ecker et al.
U.S. Appl. No. 10/660,997, filed Sep. 12, 2003, Ecker et al.
U.S. Appl. No. 10/660,122, filed Sep. 11, 2003, Ecker et al.
U.S. Appl. No. 10/660,996, filed Sep. 12, 2003, Ecker et al.

Aaserud at al., "DNA Sequencing With Blackbody Infrared Radiative Dissociation Of Electrosprayed Ions," *Int J. Mass Spectrom. Ion Processes*, 1997, vol. 167-168, pp. 705-712.

Muddiman et al., "Length and base composition of PCR-amplified nucleic acids using mass measurements from electrospray ionization mass spectrometry," *Anal Chem*. Apr. 15, 1997;69(8):1543-9.

Krahmer et al., "Electrospray quadrupole mass spectrometry analysis of model oligonucleotides and polymerase chain reaction products: determination of base substitutions, nucleotide additions/deletions, and chemical modifications," *Anal Chem.*, Jul. 15, 1999;71(14):2893-900.

T. Tsuneyoshi et al., "Mass spectrometric gene diagnosis of one-base substitution from polymerase chain reaction amplified human DNA," *Rapid Commun Mass Spectrom*. 1997;11(7):719-22.

Muddiman et al., "Characterization of PCR products from bacilli using electrospray ionization FTICR mass spectrometry," *Anal Chem*. Nov. 1, 1996;68(21):3705-12.

Hahner at al., "Analysis of short tandem repeat polymorphisms by electrospray ion trap mass spectrometry," *Nucleic Acids Res.*, Sep. 15, 2000;28(18):E82.

Null et al., "Evaluation of sample preparation techniques for mass measurements of PCR products using ESI-FT-ICR mass spectrometry," *J Am Soc Mass Spectrom*. Apr. 2002;13(4):338-44.

Huber et al., "On-line cation exchange for suppression of adduct formation in negative-ion electrospray mass spectrometry of nucleic acids," *Anal Chem.*, Dec. 15, 1998;70(24):5288-95.

Oberacher et al., "Analysis of polymerase chain reaction products by on-line liquid chromatography-mass spectrometry for genotyping of polymorphic short tandem repeat loci," *Anal Chem.*, Nov. 1, 2001;73(21):5109-15.

Sciacchitano, "Analysis Of Polymerase Chain Reaction-Amplified DNA Fragments Of Clostridium Botulinum Type E Neurotoxin Gene By High Performance Capillary Electrophoresis," *J. Liq. Chromatogr. Relat. Technol*., 1996, vol. 19, pp. 2165-2178.

Jiang et al., "A highly efficient and automated method of purifying and desalting PCR products for analysis by electrospray ionization mass spectrometry," 6*Anal Biochem*., May 1, 2003;316(1):50-7.

Aaserud, D.J. et al., "Accurate base composition of double-strand DNA by mass spectrometry," Am. Soc. Mass Spec, 1996, pp. 1266-1269, vol. 7 (12).

Adam, E. et al., "Intertype Specific Epitope Structure of Adenovirus Hexon," Acta Microbiol. Immunol. Hung., 1998, pp. 311-316, vol. 45 (3-4).

Adam, E. et al., "Molecular Structure of the Two-Dimensional Hexon Crystalline Array and of Adenovirus Capsid," Acta Microbiol. Immunol. Hung., 1998, pp. 305-310, vol. 45 (3-4).

Adam, et al., "Characterization of intertype specific epitopes on adenovirus hexons," Arch. Virol., 1998, pp. 1669-1682, vol. 143.

Adrian, T. et al., "DNA Restriction Analysis of Adenovirus Prototypes 1 to 41," Arch. Viral., 1986, pp. 277-290, vol. 91.

Adzhar et al., "Universal oligonucleotides for the detection of infectious bronchitis virus by thepolymerase chain reaction," Avian Pathology, 1996, pp. 817-836, vol. 25.

Agostini et al. "Complete genome of a JC virus genotype Type 6 from the brain of an African American with progressive multifocal leukoencephalopathy," Journal of Human Virology, 1998, pp. 267-272, vol. 1 (4).

Akalu, A. et al., "Rapid identification of subgenera of human adenovirus by serological and PCR assays," J. Virol. Methods, 1998, pp. 187-196, vol. 71 (2).

Allaouchiche et al., "Clinical Impact of Rapid Oxacillin Susceptibility Testing Using a PCR Assay in *Staphylococous aurous* Bactaeremia," J. Infect., 1999, pp. 198-204, vol. 39 (3).

Allawi, H.T. et al., "Thermodynamics and NMR of internal G.T. mismatches in DNA," Biochemistry, 1997, pp. 10581-10594, vol. 36.

Altschuel, et al., "Gapped BLAST and PSI-BLAST: a new generation of protein database search programs," Nucl. Acid Res, 1997, 25 (17), 3389-3402.

Altschuel et al., J. Mol. Biol, 1990, pp. 403-410, vol. 215.

Alves-Silva et al., "The Ancestry of Brazilian mtDNA Linages," Am. J. Hum. Genet, 2000, pp. 444-461, vol. 67.

Amano, Y. et al., "Detection of influenza virus: traditional approaches and development of biosensors," Anal. Bioanal. Chem, 2005, pp. 156-164, vol. 381.

Amexis et al., "Quantitative Mutant Analysis Of Viral Quasispecies By Chip-Based Matrix Assisted LaserDesorption Ionization Time-Of-Flight Mass Spectrometry," Proc: Natl: Acad: Sci, 2001, pp. 12097-12102, vol. 98 (21).

Anderson et al., "Mitochondrial Sequence Analysis for Forensic Identification Using Pyrosequencing Technology," BioTechniques, 2002, pp. 124-133, vol. 32.

Anderson et al., "Quantitative Filter Hybridization, in Nucleic Acid Hybridization: A Practical Approach, Hames and Higgins (eds)," 1985, pp. 73-111, IRL Press.

Anderson et al., "Sequence and organization of the human mitochondrial genome," Nature, 1981, pp. 457-465, vol. 290.

Anthony, R. M. et al., "Use of the Polymerase Chain Reaction for Rapid Detection of High-Level Mupirocin Resistance in Staphylococci," Eur. J. Clin. MicrobioL Infect. Dis., 1999, pp. 30-34, vol. 18 (1).

Application for Continuation Grant by David Mitchell Lubmann dated Jun. 4, 1996 and Jun. 14, 1996.

Application for Continuation Grant by David Mitchell Lubmann dated Jun. 10, 1994 and Jun. 24, 1994.

Application for Grant by David Mitchell Lubmann dated Sep. 1, 1994 and Sep. 27, 1994.

Application for Grant by David Mitchell Lubmann dated Oct. 25, 1995 and Oct. 29, 1992.

U.S. Appl. No. 10/326,642 Office Communication Mailed Jul. 14, 2004.

U.S. Appl. No. 10/326,642 Office Communication Mailed Nov. 21, 2003.

U.S. Appl. No. 11/331,978 Office Communication Mailed Jun. 2, 2008 (interview summary).

U.S. Appl. No. 09/798,007 Office Communication Mailed Jan. 8, 2003.

U.S. Appl. No. 09/798,007 Office Communication Mailed Jan. 31, 2003.

U.S. Appl. No. 09/798,007 Office Communication Mailed Feb. 10, 2005.

U.S. Appl. No. 09/798,007 Office Communication Mailed Feb. 27, 2003.

U.S. Appl. No. 09/798,007 Office Communication Mailed Apr. 16, 2002.

U.S. Appl. No. 09/798,007 Office Communication Mailed May 20, 2003.

U.S. Appl. No. 09/798,007 Office Communication Mailed May 28, 2003.

U.S. Appl. No. 09/798,007 Office Communication Mailed Jun. 20, 2002.

U.S. Appl. No. 09/798,007 Office Communication Mailed Jun. 30, 2004.

U.S. Appl. No. 09/798,007 Office Communication Mailed Jul. 11, 2003.

U.S. Appl. No. 09/798,007 Office Communication Mailed Aug. 10, 2004.

U.S. Appl. No. 09/798,007 Office Communication Mailed Sep. 22, 2003.

U.S. Appl. No. 09/798,007 Office Communication Mailed Nov. 6, 2002.

U.S. Appl. No. 09/798,007 Office Communication Mailed Nov. 19, 2003.

U.S. Appl. No. 09/891,793 Office Communication Mailed Mar. 8, 2005.

U.S. Appl. No. 09/891,793 Office Communication Mailed Mar. 9, 2004.

U.S. Appl. No. 09/891,793 Office Communication Mailed Mar. 16, 2006.

U.S. Appl. No. 09/891,793 Office Communication Mailed May 19, 2003 interviewsummary report.

U.S. Appl. No. 09/891,793 Office Communication Mailed May 19, 2005.

U.S. Appl. No. 09/891,793 Office Communication Mailed May 23, 2003.

U.S. Appl. No. 09/891,793 Office Communication Mailed Jun. 14, 2004.

U.S. Appl. No. 09/891,793 Office Communication Mailed Jul. 12, 2006.

U.S. Appl. No. 09/891,793 Office Communication Mailed Jul. 13, 2004.

U.S. Appl. No. 09/891,793 Office Communication Mailed Jul. 22, 2008.

U.S. Appl. No. 09/891,793 Office Communication Mailed Aug. 10, 2004.

U.S. Appl. No. 09/891,793 Office Communication Mailed Aug. 11, 2005.

U.S. Appl. No. 09/891,793 Office Communication Mailed Aug. 26, 2003.

U.S. Appl. No. 09/891,793 Office Communication Mailed Sep. 13, 2006.

U.S. Appl. No. 09/891,793 Office Communication Mailed Oct. 20, 2004.

U.S. Appl. No. 09/891,793 Office Communication Mailed Nov. 13, 2003.

U.S. Appl. No. 09/891,793 Office Communication Mailed Nov. 20, 2006.

U.S. Appl. No. 09/891,793 Office Communication Mailed Dec. 18, 2002.

U.S. Appl. No. 10/156,608 Office Communication Mailed Apr. 1, 2004.

U.S. Appl. No. 10/156,608 Office Communication Mailed May 10, 20005.

U.S. Appl. No. 10/156,608 Office Communication Mailed May 18, 2004.

U.S. Appl. No. 10/156,608 Office Communication Mailed May 23, 2005.

U.S. Appl. No. 10/156,608 Office Communication Mailed May 26, 2005.

U.S. Appl. No. 10/156,608 Office Communication Mailed Jun. 2, 2005 with associated information Disclosure Statement filed Nov. 28, 2005.

U.S. Appl. No. 10/156,608 Office Communication Mailed Jun. 2, 2006.

U.S. Appl. No. 10/156,608 Office Communication Mailed Jul. 19, 2005.

U.S. Appl. No. 10/156,608 Office Communication Mailed Jul. 20, 2005.

U.S. Appl. No. 10/156,608 Office Communication Mailed Aug. 10, 2004.

U.S. Appl. No. 10/156,608 Office Communication Mailed Sep. 15, 2005.

U.S. Appl. No. 10/156,608 Office Communication Mailed Oct. 14, 2004.

U.S. Appl. No. 10/156,608 Office Communication Mailed Nov. 19, 2004.

U.S. Appl. No. 10/156,608 Office Communication Mailed Dec. 9, 2004.

U.S. Appl. No. 10/323,438 Office Communication Mailed Jul. 26, 2004.

U.S. Appl. No. 10/323,438 Office Communication Mailed Nov. 20, 2003.

U.S. Appl. No. 10/325,527 Office Communication Mailed Mar. 11, 2005.

U.S. Appl. No. 10/325,527 Office Communication Mailed Aug. 16, 2004.
U.S. Appl. No. 10/325,527 Office Communication Mailed Dec. 3, 2003.
U.S. Appl. No. 10/418,514 Office Communication Mailed Feb. 27, 2006.
U.S. Appl. No. 10/418,514 Office Communication Mailed Mar. 23, 2009.
U.S. Appl. No. 10/418,514 Office Communication Mailed Mar. 27, 2007.
U.S. Appl. No. 10/418,514 Office Communication Mailed Apr. 15, 2008.
U.S. Appl. No. 10/418,514 Office Communication Mailed Jul. 1, 2008.
U.S. Appl. No. 10/418,514 Office Communication Mailed Sep. 29, 2005.
U.S. Appl. No. 10/418,514 Office Communication Mailed Sep. 29, 2009.
U.S. Appl. No. 10/418,514 Office Communication Mailed Dec. 6, 2007.
U.S. Appl. No. 10/660,122 Office Communication Mailed Mar. 17, 2006.
U.S. Appl. No. 10/660,122 Office Communication Mailed Mar. 21, 2008.
U.S. Appl. No. 10/660,122 Office Communication Mailed Apr. 20, 2007.
U.S. Appl. No. 10/660,122 Office Communication Mailed Jul. 6, 2006.
U.S. Appl. No. 10/660,122 Office Communication Mailed Jul. 9, 2008.
U.S. Appl. No. 10/660,122 Office Communication Mailed Sep. 17, 2008.
U.S. Appl. No. 10/660,122 Office Communication Mailed Sep. 19, 2006.
U.S. Appl. No. 10/660,122 Office Communication Mailed Sep. 19, 2007.
U.S. Appl. No. 10/660,996 Office Communication Mailed Feb. 28, 2006.
U.S. Appl. No. 10/660,996 Office Communication Mailed May 30, 2006.
U.S. Appl. No. 10/660,996 Office Communication Mailed Jul. 10, 2007 withassociated Information Disclosure Statement filed Feb. 21, 2007.
U.S. Appl. No. 10/660,996 Office Communication Mailed Jul. 12, 2006.
U.S. Appl. No. 10/660,996 Office Communication Mailed Sep. 5, 2006.
U.S. Appl. No. 10/660,996 Office Communication Mailed Nov. 22, 2006.
U.S. Appl. No. 10/660,997 Office Communication Mailed Mar. 13, 2006.
U.S. Appl. No. 10/660,997 Office Communication Mailed May 26, 2007 withassociated Information Disclosure Statement filed Feb. 20, 2007.
U.S. Appl. No. 10/660,997 Office Communication Mailed May 26, 2006.
U.S. Appl. No. 10/660,997 Office Communication Mailed Sep. 18, 2006.
U.S. Appl. No. 10/660,997 Office Communication Mailed Nov. 21, 2006.
U.S. Appl. No. 10/660,998 Office Communication Mailed Jan. 24, 2007.
U.S. Appl. No. 10/660,998 Office Communication Mailed Apr. 7, 2009.
U.S. Appl. No. 10/660,998 Office Communication Mailed May 1, 2006.
U.S. Appl. No. 10/660,998 Office Communication Mailed Aug. 3, 2006.
U.S. Appl. No. 10/660,998 Office Communication Mailed Aug. 7, 2007.
U.S. Appl. No. 10/660,998 Office Communication Mailed Sep. 18, 2008.
U.S. Appl. No. 10/660,998 Office Communication Mailed Sep. 19, 2008.
U.S. Appl. No. 10/660,998 Office Communication Mailed Dec. 11, 2007.
U.S. Appl. No. 10/728,486 Office Communication Mailed Jan. 17, 2008.
U.S. Appl. No. 10/728,486 Office Communication Mailed Jan. 23, 2008.
U.S. Appl. No. 10/728,486 Office Communication Mailed Apr. 10, 2006.
U.S. Appl. No. 10/728,486 Office Communication Mailed May 11, 2007.
U.S. Appl. No. 10/728,486 Office Communication Mailed Jul. 27, 2006.
U.S. Appl. No. 10/728,486 Office Communication Mailed Oct. 17, 2007.
U.S. Appl. No. 10/728,486 Office Communication Mailed nov. 3, 2008.
U.S. Appl. No. 10/728,486 Office Communication Mailed Dec. 20, 2006.
U.S. Appl. No. 10/754,415 Office Communication Mailed Feb. 27, 2007.
U.S. Appl. No. 10/754,415 Office Communication Mailed Mar. 13, 2006.
U.S. Appl. No. 10/754,415 Office Communication Mailed Jun. 4, 2009.
U.S. Appl. No. 10/754,415 Office Communication Mailed Jun. 12, 2008.
U.S. Appl. No. 10/754,415 Office Communication Mailed Aug. 28, 2006.
U.S. Appl. No. 10/754,415 Office Communication Mailed Aug. 30, 2007.
U.S. Appl. No. 10/754,415 Office Communication Mailed Oct. 10, 2007.
U.S. Appl. No. 10/754,415 Office Communication Mailed Nov. 17, 2006.
U.S. Appl. No. 10/829,826 Office Communication Mailed Apr. 4, 2008.
U.S. Appl. No. 10/829,826 Office Communication Mailed Jul. 6, 2007.
U.S. Appl. No. 10/829,826 Office Communication Mailed Dec. 10, 2008.
U.S. Appl. No. 10/844,938 Office Communication Mailed Jan. 30, 2009.
U.S. Appl. No. 10/844,938 Office Communication Mailed Feb. 2, 2007.
U.S. Appl. No. 10/844,938 Office Communication Mailed May 20, 2008.
U.S. Appl. No. 10/844,938 Office Communication Mailed Aug. 7, 2007.
U.S. Appl. No. 10/891,337 Office Communication Mailed Apr. 20, 2009.
U.S. Appl. No. 10/933,928 Office Communication Mailed Jun. 2, 2006.
U.S. Appl. No. 10/943,344 Office Communication Mailed Feb. 23, 2009.
U.S. Appl. No. 10/943,344 Office Communication Mailed Feb. 27, 2007.
U.S. Appl. No. 10/943,344 Office Communication Mailed May 21, 2008.
U.S. Appl. No. 10/943,344 Office Communication Mailed Oct. 14, 2009.
U.S. Appl. No. 11/059,776 Office Communication Mailed Jan. 19, 2007.
U.S. Appl. No. 11/059,776 Office Communication Mailed Jan. 23, 2008.
U.S. Appl. No. 11/059,776 Office Communication Mailed May 29, 2007.
U.S. Appl. No. 11/060,135 Office Communication Mailed Jan. 2, 2009.
U.S. Appl. No. 11/060,135 Office Communication Mailed Mar. 8, 2007.

U.S. Appl. No. 11/060,135 Office Communication Mailed Mar. 25, 2008.
U.S. Appl. No. 11/060,135 Office Communication Mailed Jul. 15, 2009.
U.S. Appl. No. 11/060,135 Office Communication Mailed Jul. 24, 2007.
U.S. Appl. No. 11/060,135 Office Communication Mailed Dec. 21, 2006.
U.S. Appl. No. 11/070,632 Office Communication Mailed Jun. 30, 2008.
U.S. Appl. No. 11/070,632 Office Communication Mailed Jul. 23, 2009.
U.S. Appl. No. 11/070,632 Office Communication Mailed Oct. 6, 2008.
U.S. Appl. No. 11/136,134 Office Communication Mailed Feb. 12, 2009.
U.S. Appl. No. 11/136,134 Office Communication Mailed Mar. 26, 2008.
U.S. Appl. No. 11/136,134 Office Communication Mailed May 21, 2009.
U.S. Appl. No. 11/136,134 Office Communication Mailed Jun. 20, 2007.
U.S. Appl. No. 11/136,134 Office Communication Mailed Oct. 31, 2008.
U.S. Appl. No. 11/210,516 Office Communication Mailed Jun. 8, 2007.
U.S. Appl. No. 11/210,516 Office Communication Mailed Oct. 19, 2007.
U.S. Appl. No. 11/233,630 Office Communication Mailed Apr. 16, 2008.
U.S. Appl. No. 11/233,630 Office Communication Mailed Jun. 8, 2007.
U.S. Appl. No. 11/233,630 Office Communication Mailed Jul. 13, 2007.
U.S. Appl. No. 11/233,630 Office Communication Mailed Oct. 2, 2008.
U.S. Appl. No. 11/331,978 Office Communication Mailed Aug. 15, 2008.
U.S. Appl. No. 11/331,978 Office Communication Mailed Oct. 17, 2008.
U.S. Appl. No. 11/331,978 Office Communication Mailed Nov. 15, 2007.
U.S. Appl. No. 11/331,987 Office Communication Mailed Jul. 9, 2008.
U.S. Appl. No. 11/331,987 Office Communication Mailed Jul. 16, 2007.
U.S. Appl. No. 11/331,987 Office Communication Mailed Oct. 22, 2007.
U.S. Appl. No. 11/331,987 Office Communication Mailed Nov. 20, 2009.
U.S. Appl. No. 11/404,561 Office Communication Mailed Feb. 4, 2009.
U.S. Appl. No. 11/404,561 Office Communication Mailed May 16, 2008.
U.S. Appl. No. 11/409,535 Office Communication Mailed Apr. 16, 2008.
U.S. Appl. No. 11/409,535 Office Communication Mailed Oct. 31, 2007.
U.S. Appl. No. 11/491,376 Office Communication Mailed Jan. 12, 2010.
U.S. Appl. No. 11/491,376 Office Communication Mailed Apr. 22, 2009.
U.S. Appl. No. 11/491,376 Office Communication Mailed Oct. 31, 2008.
U.S. Appl. No. 11/582,859 Office Communication Mailed Oct. 21, 2008.
U.S. Appl. No. 11/582,863 Office Communication Mailed Feb. 26, 2009.
U.S. Appl. No. 11/582,863 Office Communication Mailed Jun. 17, 2008.
U.S. Appl. No. 11/582,863 Office Communication Mailed Aug. 20, 2007.
U.S. Appl. No. 11/582,930 Office Communication Mailed Jan. 16, 2009.
U.S. Appl. No. 11/582,930 Office Communication Mailed May 2, 2008.
U.S. Appl. No. 11/582,930 Office Communication Mailed Jul. 2, 2009.
U.S. Appl. No. 11/582,930 Office Communication Mailed Sep. 14, 2007.
U.S. Appl. No. 11/582,930 Office Communication Mailed Oct. 24, 2008.
U.S. Appl. No. 11/685,598 Office Communication Mailed Aug. 18, 2009.
U.S. Appl. No. 11/754,163 Office Communication Mailed Jul. 28, 2009.
U.S. Appl. No. 11/754,169 Office Communication Mailed Aug. 25, 2009.
U.S. Appl. No. 11/754,174 Office Communication Mailed Aug. 3, 2009.
U.S. Appl. No. 11/754,182 Office Communication Mailed Jul. 2, 2009.
U.S. Appl. No. 11/929,707 Office Communication Mailed Jul. 17, 2009.
U.S. Appl. No. 11/929,707 Office Communication Mailed Aug. 16, 2010.
U.S. Appl. No. 11/929,707 Office Communication Mailed Oct. 2, 2009.
U.S. Appl. No. 11/930,002 Office Communication Mailed Sep. 29, 2009.
U.S. Appl. No. 12/211,641 Office Communication Mailed Apr. 17, 2009.
U.S. Appl. No. 12/326,800 Office Communication Mailed Oct. 21, 2009.
U.S. Appl. No. 90/010,209 Office Communication Mailed Jun. 27, 2008.
U.S. Appl. No. 90/010,209 Office Communication Mailed Jul. 22, 2008.
U.S. Appl. No. 90/010,210 Office Communication Mailed Jun. 27, 2008.
U.S. Appl. No. 90/010,210 Office Communication Mailed Jul. 22, 2008.
U.S. Appl. No. 90/010,447 Office Communication Mailed Mar. 12, 2009.
U.S. Appl. No. 90/010,447 Office Communication Mailed Apr. 24, 2009.
U.S. Appl. No. 90/010,447 Office Communication Mailed Sep. 20, 2010.
U.S. Appl. No. 90/010,447 Office Communication Mailed Oct. 29, 2009.
U.S. Appl. No. 90/010,448 Office Communication Mailed Mar. 12, 2009.
U.S. Appl. No. 90/010,448 Office Communication Mailed Apr. 24, 2009.
U.S. Appl. No. 90/010,448 Office Communication Mailed Sep. 20, 2010.
U.S. Appl. No. 90/010,448 Office Communication Mailed Oct. 29, 2009.
Arbique et al., "Comparison of the Velogene Rapid MRSA Identification Assay, Denka MRSAScreen Assay, and BBL Crystal MRSA ID System for rapid identification of methicillin-resistant *Staphylococcus aureus*," Diagn. Microbiol. Infect. Dis., 2001, pp. 5-10, vol. 40(1-2).
Archer, G. L. et al., "Detection of Methicillin Resistance in Staphylococci by Using a DNA Probe," Antimicrob. Agents Chemother., 1990, pp. 1720-1724, vol. 34 (9).
Armstrong, P. et al., "Sensitive and Specific Colorimetric Dot Assay to Detect Eastern Equine Encephalomyelitis Viral RNA in Mosquitoes After PCR Amplification," J. Med, Entomol., 1995, pp. 42-52, vol. 32 (1).
Arnal et al., "Quantification of Hepatitis A virus in shellfish by competitive reverse transcription PCR with coextraction of standard RNA," Applied and Environmental Microbiology, American Society forMicrobiology, 1999, pp. 322-326, vol. 65 (1).

Aronsson et al., "Persistence of the influenza A/WSN/33 virus RNA at midbrain levels of immunodefective mice, Online Publication," Journal of the NeuroVirology, 2001, pp. 117-124, vol. 7.
Australian Search Report for AU 2003297687 dated Sep. 4, 2008.
Australian Search Report for AU 2003302236 dated Sep. 10, 2008.
Australian Search Report for AU 2004248107 dated Jul. 30, 2008.
Ausubel et al., "Short Protocols in Molecular Biology, 2nd Ed. A Compendium of Methods from Current Protocols in Molecular Biology(Relevant portions of the book)," 1992.
Ausubel F. M., et al., "Current Protocols in Molecular Biology," John Wiley & Sons, 2004, Table of Contents.
Avellon, A. et al., "Rapid and sensitive diagnosis of human adenovirus infections by a generic polymerase chain reaction," J. Viral. Methods, 2001, pp. 113-120, vol. 92 (2).
Azevedo, A. M. et al., "Detection of influenza, parainfluenza, adenovirus and respiratory syncytial virus during asthma attacks in children older than 2 years old," Allergol. Immunopathol., 2003, pp. 311-317, vol. 31 (6).
Baba T. et al., "genome and virulence determinants of high virulence community—acquired MRSA," The Lancet, 2002, pp. 1819-1827, vol. 359.
Bahrmahd. et al., "Polymerise chain reaction of bacterial genomes with single universal primer: app.lication to distinguishing Mycobacteria species," Mol. Cell. Probes, 1996, pp. 117-122, vol. 10 (2).
Bahrmahd. et al., "Use of restriction enzyme analysis of amplified DNA coding for the hsp65 gene and polymerase chain reaction with universal primer for rapid differtiation of Mycobacterium species in the clinical laboratory," Scand. J. Infect. Dis, 1998, pp. 477-480, vol. 30 (5).
Bai, J, T.H. Liu et al. "Matrix-Assisted Laser Desorption/Ionization Mass Spectrometry of Restriction Enzyme-Digested Plasmid DNA Using an Active Nafion Substrate," Rapid Commun. Mass Spectrom, 1994, pp. 687-691, vol. 8.
Baker, et al., "Review and re-analysis of domain-specific 16S primers," J. Microbiol. Methods, 2003, pp. 541-555, vol. 55.
Banik, U. et al., "Multiplex PCR Assay for Rapid Identification of Oculopathogenic Adenoviruses by Amplification of the Fiber and Hexon Genes," J. Clin. Microbiol., 2005, pp. 1064-1068, vol. 43 (3).
Barbour et al., "Identification of an uncultivatable Borrelia species in the hard tick *Amblyomma americanum*: Possible agent of a Lyme disease-like illness", The Journal of Infectious Diseases, 1996, pp. 403-409, vol. 173.
Barns et al., "Detection of diverse new Francisella-like bacteria in environmental samples", Applied and Environmental Microbiology, 2005, pp. 5494-5500, vol. 71.
Baron, E. J., "Genetic Aspects of Methicillin Resistance in *Staphylococcus aureus* and MethodsUsed for its Detection in Clinical Laboratories in the United States," J. Chemother., 1995, pp. 87-92, vol. 7 (Suppl.3).
Barr, I. G. et al., "An Influenza A(H3) Reassortant Was Epidemic in Australia and New Zealand in 2003," J. Med. Virol., 2005, pp. 391-397, vol. 76.
Barski, P. et al., "Rapid assay for detection of methicillin-resistant *Staphylococcus aureus* usingmultiplex PCR," Mol. Cell Probes, 1996, pp. 471-475, vol. 10.
Bastia, et al., "Organelle DNA analysis of Solanum and Brassica somatic hybrids by PCR with universal primers," Theor. App.l. Genet, 2001, pp. 1265-1272, vol. 102 (8).
Batey et al., "Preparation of Isotopically Labeled Ribonucleotides for Multidimensional NMR Spectroscopy of RNA," Nucleic Acids Research, 1992, pp. 4515-4523, vol. 20 (17).
Baumer et al., "Age-related Human mtDNA Deletions: A Heterogeneous Set of Deletions Arising at aSingle Pair of Directly Repeated Sequences," Am. J. Hum. Genet., 1994, pp. 618-630, vol. 54.
Beall, B., et al., "Survey of emm Gene Sequences and T-Antigen Types fromSystemic *Streptococcus pyogenes* Infection Isolates Collected in San Francisco, California; Atlanta, Georgia; and Connecticut in 1994 and 1995," J. Clin. Micro., 1997, pp. 1231-1235.
Beall et al., "Sequencing emm-Specific PCR Products for Routine andAccurate Typing of Group A Streptococci," J. Clin. Micro, 1996, pp. 953-958, vol. 34.

Benko, M. et al., "Family Adenoviridae," Virus taxonomy. VIIIth report of the International Committee on Taxonomy of Viruses, 2004, pp. 213-228, Academic Press, New York.
Benson, et al., "Advantages of *Thermococcus kodakaraenis* (KOD) DNA polymerase for PCR-mass spectrometry based analyses," J. Am. Soc. Mass Spectrom, 2003, pp. 601-604, vol. 14.
Berencsi, G. et al., "Molecular Biological Characterization of Adenovirus DNA," Acta Microbiol. Immunol. Hung, 1998, pp. 297-304, vol. 45 (3-4).
Bishop et al., "Chapter 4 Molecular sequence databases In Nucleic acid and protein sequence analysis: a practical approach", 1987, IRL Press, Oxford England, Ed. M.J. Bishop and C.J. Rawlings, pp. 83-113.
Bisno, A.L., "Streptococcus Pyogenes," Infectious Diseases and Their Etiologic Agents in "Principles and Practice of Infectious Diseases," 1995, pp. 1786-1799, vol. 2.
Black. et al., "Detection of trace levels of tricothecene mycotoxins in human urineby gas chromatography-mass spectrometry," J. Chromatog., 1986, pp. 103-115, vol. 367.
Blaiotta, G. et al., "PCR detection of staphylococcal enterotoxin genes in *Staphyiococcus* spp. strains isolated from meat and dairy products. Evidence for new variants of seG and sel in S. aureus AB-8802," J. Appl. Microbiol., 2004, pp. 719-730, vol. 97.
BLAST Search results (Mar. 2006).
Bonk Thomas et al., "Matrix-assisted laser desorption/ionization time-of-flight mass spectrometry-based detection of microsatellite instabilities in coding DNA sequences: a novel approach to identify DnA-mismatch repair-deficient cancer cells," Clinical C.
Bronzoni, R. V. M. et al., "Duplex Reverse Transcription-PCR Followed by Nested PCR. Assat for Detection and Identification of Brazilan Alphaviruses and Flaviviruses," J. Clin. Microbiol., 2005, pp. 696-702, vol. 43 (2).
Bronzoni, R. V. M. et al., "Multiplex nested PCR for Brazilian Alphavirus diagnosis," Trans. R. Soc. Trop. Med. Hyg, 2004, pp. 456-461, vol. 98 (8).
Brown, I. H., "Advances in Molecular Diagnostics for Avian Influenza," Dev. Biol., 2006, pp. 93-97, vol. 124.
Brownstein, M. J. et al., "Modulation of Non-Templated Nucleotide Addition by Taq DNA Polymerase: Primer Modifications that Facilitate Genotyping," BioTechniques, 1996, pp. 1004-1010, vol. 20.
Brunaud V. et al., "T-DNA integration into the Arabidopsis genome depends on sequence of pre-insertion sites," EMBO Rep, 2002, pp. 1152-1157, vol. 3 (12).
Buck et al., "Design Strategies and Performance of Custom DNA Sequencing Primers.," BioTechniques, 1999, pp. 528-536, vol. 27.
Butel, J. S. et al., "Cell and Molecular Biology of Simian Virus 40: Implications for Human Infections and Disease," Natl. Cancer Institute, 1999, pp. 119-134, vol. 91 (2).
Butler et al., "DNA profiling and quantitation of human DNA," CCQM BAWG, Apr. 12, 2005.
Campbell and Huang, "Detection of California serogroup Bunyavirus in tissue culture and mosquito pools by PCR," J. Virol. Methods, 1996, pp. 175-179, vol. 57 (2).
Canadian patent office communication for Application No. 2,525,498 dated Feb. 5, 2009.
Canadian patent office communication for Application No. 2,525,498 dated Jul. 4, 2009.
Canadian patent office communication for Application No. 2,567,839 dated Apr. 7, 2009.
Carracedo et al., "DNA commission of the international society for forensic genetics: guidelines formitochondrial DNA typing," Forensic Science International, 2000, pp. 79-85, vol. 110.
Carroll, K. C. et al., "Rapid Detection of the Staphylococcal mecA Gene from BACTEC BloodCulture Bottles by the Polymerase Chain Reaction," Am. J. Clin. Pathol., 1996, pp. 600-605, vol. 106.
Case et al., "Maternal inheritance of mitochondria! DNA polymorphisms in cultured human fibroblasts," Somatic Cell Genetics, 1981, pp. 103-108, vol. 7.
Cattoli, G. et al., "Comparison of three rapid detection systems for type A influenza virus on tracheal swabs of experimentally and naturally infected birds," Avian Pathology, 2004, pp. 432-437, vol. 33 (4).
Cavassin I, M. et al., "Evaluation of MRSA-Screen, a Simple Anti-PBP 2a Slide Latex AgglutinationKit, for Rapid Detection of Methicillin Resistance in *Staphylococcus aureus*," J. Clin. Microbial., 1999, pp. 1591-1594, vol. 37 (5).

Cespedes, et al., "Polymerase chain reaction-restriction fragment length polymorphism analysis of a short fragment of the cytochrome b gene for identification of flatfish species," J. Food Protection, 1998, pp. 1684-1685, vol. 61 (12).

Chamberlin et al., "New RNA polymerase from *Escerichia coli* infected with bacteriophage T7," Nature, 1970, pp. 227-231, vol. 228.

Chandra, S. et al., "Virus reduction in the preparation and intravenous globulin: in vitro experiments," Transfusion, 1999, pp. 249-257, vol. 39 (3).

Chang, P.K. et al., "aflT, a MFS transporter-encoding gene located in the aflatoxin gene cluster, does not have a significant role in aflatoxin secretion," Fungal Genet. Biol., 2004, pp. 911-920, vol. 41.

Chaves, F. et al., "Molecular Characterization of Resistance to Mupirocin in Methicillin-Susceptible and -Resistant Isolates of *Staphylococcus aureus* from Nasal Samples," J. Clin. Microbiol., 2004, pp. 822-824, vol. 42 (2).

Chelly et al., "Transcription of the dystrophin gene in human muscle and non-muscle tissue," Nature, 1988, pp. 858-860, vol. 333 (6176).

Chen and Yu, "Universal primers for amplification of mitochondria! small subunit ribosomal RNA-encoding gene in scleractinian corals," Mar. Biotechnol, 2000, pp. 146-153, vol. 2.

Chen, Ch et al., "Laser Desorption Mass Spectrometry for FastDNA Sequencing," http://www.ornl.gove/sci/techresources/Human_Genome/publicat/94SANTA/sequencing/seqtoc.shtml ('787 reexamination), 1994.

Chen, et al., "A universal PCR primer to detect members of the Potyviridae and its use to examine the taxonomic status of several members of the family," Arch. Virol, 2001, pp. 757-766, vol. 146.

Chen N et al., "The genomic sequence of ectromelia virus, the causative agent of mousepox," Virology, 2003, pp. 165-186, vol. 317 (1), Academic Press,Orlando, US.

Chen R., et al., "Trapping, Detection, and Charge and Mass Measurement of Large Individual Ions (up to 1.1 X 108 Daltons) by Electrospray Ionization FYICR MS", 42nd ASMA Conference on Mass Spectrometry, 1994.

Chen, Y. Z. et al., "A BAC-Based STS-Content Map Spanning a 35-Mb Region of Human Chromosome 1p35-36," Genomics, 2001, pp. 55-70, vol. 74 (1).

Chen, Z. et al., "Genetic mapping of the cold-adapted phenotype of B/Ann Arbor/1/66, the master donor virus for live attenuated influenza vaccines (FluMist)," Virology, 2006, pp. 416-423, vol. 345.

Chinese Office Communication for CN200480016187.9 dated Jun. 12, 2009.

Chmielewicz, B. et al., "Development of a PCR-Based Assay for Detection, Quantification, and Genotyping of Human Adenoviruses," Clin. Chem, 2005, pp. 1365- 1373, vol. 51 (8).

Cho et al., "App.lication of the ribonuclease P (RNaseP) RNA gene sequence for phylogenetic analysis of the genus *Saccharomonospora*," Inn J. Systematic Biol, 1998, pp. 1223-1230, vol. 48.

Choi, S. et al., "Real-Time PCR Quantification of Human Adenoviruses in Urban Rivers Indicates Genome Prevalence but Low Infectivity," Appl. Environ. Microbiol., 2005, pp. 7426-7433, vol. 71 (11).

Choi, Y.K. et al., "Detection and subtying of swine influenza H1N1, H1 N2 and H3N2 viruses in clinical samples using two multiplex RT-PCR assays," J. Viral. Methods, 2002, pp. 53-59, vol. 102.

Christel, La et al., "Rapid, Automated Nucleic Acid Probe Assays Using Silicon Microstructures forNucleic Acid Concentration," J. Biomech. Eng, 1999, pp. 22-27, vol. 121.

Claas, E.C.J. et al., "Internally Controlled Real-Time PCT Monitoring of Adenovirus DNA Load inSerum or Plasma of Transplant Recipients," J. Clin. Microbiol., 2005, pp. 1738- 1744, vol. 43 (4).

Cloney, L. et al., "Rapid detection of mecA in methicillin resistant *Staphylococcus aureus* using cycling probe technology," MoL Cell Probes, 1999, pp. 191-197, vol. 13.

Conrads. et al., "16S-23S rDNA internal transcribed spacer sequences for analysis of the phylogenetic relationships among species of the genus Fusobacterium," Intl. J. System. Evol. Micrbiol, 2002, pp. 493-499, vol. 52 (2).

Contreras-Salazar et al., "up regulation of the Epstein-Barr virus (EBV)-encoded membrane protein LMP in the Burkitt's lymphoma line Daudi after exposure to n-Butyrate and after EBV superinfection," J. Virol., 1990, pp. 5441-5447, vol. 64 (11).

Cornel, et al., "Polymerase chain reaction species diagnostic assay for *Anopheles quadrimaculatus* cryptic species (Diptera:Culicidae) based on ribosomal DNA ITS2 sequences," J. Med. Entomol, 1996, pp. 109-116, vol. 33 (1).

Couto, I. et al., "Development of Methicillin Resistance in Clinical Isolates of *Staphylococcus sciuri* by Transcriptional Activation of the mecA Homologue Native to the Species," J. Bacterial., 2003, pp. 645-653, vol. 185 (2).

Crain and McCloskey, "App.lications of mass spectrometry to the characterization of oligonucleotides and nucleic acids," Anal. Biotechnol, 1998, pp. 25-34, vol. 9 (1).

Crawford-Miksza, L. K. et al., "Analysis of 15 Adenovirus Hexon Proteins Reveals the Location and Structure of Seven Hypervariable Regions Containing Serotype-Specific Residues," J. Viral., 1996, pp. 1836-1844, vol. 70 (3).

Crawford-Miksza, L. K. et al., "Strain variation in adenovirus serotypes 4 and 7a causing acute respiratory disease," J. Clin. Micro, 1999, pp. 1107-1112, vol. 37 (4).

Crawford-Miksza, L.K. et al., "Adenovirus Serotype Evolution is Driven by Illegitimate Recombination in the Hypervariable Regions of the Hexon Protein," Virol, 1996, pp. 357- 367, vol. 224.

Crespillo et al., "Mitochondrial DNA sequences for 118 individuals from northeastern Spain," Int. J. Legal Med, 2000, pp. 130-132, vol. 114.

Cui, L. et al., "Contribution of a Thickened Cell Wall and Its Glutamine Nonamidated Component to the Vancomycin Resistance Expressed by *Staphylococcus aureus* Mu50," Antimicrob. Agents Chemother, 2000, pp. 2276-2285, vol. 44 (9).

Dasen. et al., "Classification and identification of Propiolbacteria based on ribosomal RNA genes and PCR," System. App.l. Microbiol, 1998, pp. 251-259, vol. 21 (2).

Database EMBL [Online] Nov. 26, 1993, {deletion 6} [human, muscle, Mitochondrial Mutant, 22 nt, segment 2 of 2].

De Jong, J.C. et al., "Adenoviruses from Human Immunodeficiency Virus-Infected Individuals,Including Two Strains That Represent New Candidate Serotypes Ad50 and Ad51 of Species B1 and D, Respectively," 1999, pp. 3940-3945, vol. 37 (12).

De La Puente-Redondo et al., "Comparison of different PCR approaches for typing of *Francisella tularensis* strains", Journal of Clinical Microbiology, 2000, pp. 1016-1022, vol. 38.

De Sousa, M. A. et al., "Bridges from hospitals to the laboratory: genetic portraits of methicillin-resistant *Staphylococcus aureus* clones," FEMS Immunol. Med. Microbiol, 2004, pp. 101-111, vol. 40.

Deforce and Van den Eeckhout, "Analysis of Oligonucleotides by ESI-MS," Advances in Chromatography (New York), 2000, pp. 539-566, vol. 40.

Deforce. et al., "Characterization of DNA oligonudeotides by coupling of capillary zone electrophoresis to electrospray ionization Q-TOF mass spectrometry," Anal. Chem, 1998, pp. 3060-3068, vol. 70 (14).

Del Blanco et al., "Genotyping of *Francisella tularensis* strains by pulsed-field gel electrophoresis, amplified fragment length polymorphism fingerprinting, and 16S rRNA gene sequencing", Journal of Clinical Microbiology, 2002, pp. 2964-2972, vol. 40.

Del Vecchio, V. G. et al., "Molecular Genotyping of Methicillin-Resistant *Staphylococcus aureus* via Fluorophore-Enhanced Repetitive-Sequence PCR," J. Clin. MicrobioL, 1995, pp. 2141-2144, vol. 33 (8).

Demesure. et al., "A set of universal primers for amplification of polymorphic non-coding regions of mitochondrial and chioroplast DNA in plants," Molecular Ecology, 1995, pp. 129-131, vol. 4.

Denis et al., "Development of a semiquantitative PCR assay using internal standard and colorimetricdetection on microwell plate for pseudorabies virus," Mol. Cell. Probes, 1997, pp. 439-448, vol. 11 (6).

Deurenberg et al., "The prevalence of the *Staphylococcus aureus* tst gene among community- and hospital-acquired strains and isolates from Wegener's Granulomatosis patients," FEMS Microbiol. Lett., 2005, pp. 185-189, vol. 245.

Deurenberg, R. H. et al., "Rapid detection of Panton-Valentine leukocidin from clinical isolates of *Staphylococcus aureus* strains by real-time PCR," FEMS Microbiol. Lett., 2004, pp. 225-228, vol. 240 (2).

Di Guilmi, A.M. et al., "Human adenovirus serotype 3 (Ad3) and the Ad3 fiber pprotein bind to a 130-kDa membrane protein on HLa cells," Virus Res., 1995, pp. 71-81, vol. 38.

Dias Neto, E. et al., "Shotgun sequencing of the human transcriptome with ORF expressed sequence tags," PNAS, 2000, pp. 3491-3496, vol. 97 (7).

Diep, B. A. et al., "Complete genome sequence of USA300, an epidemic clone of communityacquired meticillin-resistant *Staphylococcus aureus*," Lancet, 2006, pp. 731-739, vol. 367.

Dinauer. et al., "Sequence-based typing of HLA class II DQB1," Tissue Antigens, 2000, pp. 364-368, vol. 55 (4).

Ding and Cantor, "A high-throughput gene expression analysis technique using compettiive PCR and matrixassisted laser desorption ionization time-of-flight MS," Proc. Natl. Acad. Sci, 2003, pp. 3059-3064, vol. 100 (6).

Donehower, et al., "The use of primers from highly conserved pol regions to identifyuncharacterized retroviruses by the polymerase chain reaction," J. Vir. Methods, 1990, pp. 33-46, vol. 28.

Donofrio et al., "Detection of influenza A and B in respiratory secretions with the polymerase chain reaction" PCR methods and applications, Cold Spring Harbor Lab, 1992, pp. 263268, vol. 1 (4).

Doty et al., "Strand separation and specific recombination in deoxyribonucleic acids: physical chemical studies", Proc. Natl. Acad. Sci. USA, 1960, pp. 461-476, vol. 46.

Drosten et al., "Identification ofa Novel Coronavirus in Patients with Severe Acute Respiratory Syndrome", New England Journal of Medicine, 2003, pp. 1967-1976, vol. 348.

Dubernet, et al., "A PCR-based method for Identification of lactobacilli at to genus level," FEMS Microbiol. Lett, 2002, pp. 271-275, vol. 214 (2).

EBI Accession No. AEM14131 (Jan. 11, 2007)—Bacterial DNA PCR Primer SEQ ID No:874.

Ebner, K. et al., "Molecular Detection and Quantitative Analysis of the Entire Spectrum of HumanAdenoviruses by a Two-Reaction Real-Time PCR Assay," J. Clin. Microbiol, 2005, pp. 3049-3053, vol. 43 (7).

Ebner, K. et al., "Typing of Human Adenoviruses in Specimens from Immunosuppressed Patients by PCR-Fragment Length Analysis and Real-Time Quantitative PCR," Journal of Clinical Microbiology, 2006, pp. 2808-2815, vol. 44 (8).

Echavarria, M. et al., "Detection of Adenoviruses (AdV) in Culture-Negative EnvironmentalSamples by PCR During an AdV-Associated Respiratory Disease Outbreak," J. Clin. Microbiol, 2000, pp. 2982-2984, vol. 38 (8).

Echavarria, M. et al., "PCR Method for Detection of Adenovirus in Urine of Healthy and HumanImmunodeficiency Virus-Infected Individuals," J. Clin. Microbiol, 1998, pp. 3323-3326, vol. 36 (11).

Echavarria, M. et al., "Prediction of severe disseminated adenovirus infection by serum PCR," Lancet, 2001, pp. 384-385, vol. 358.

Echavarria, M. et al., "Rapid Detection of Adenovirus in Throat Swab Specimens by PCR DuringRespiratory Disease Outbreaks among Military Recruits," J. Clin. Microbiol, 2003, pp. 810-812, vol. 41 (2).

Echavarria, M. et al., "Use of PCR to Demonstrate Presence of Adenovirus Species B, C, or F as Well as Coinfection with Two Adenovirus Species in Children with Flu-Like Symptoms," J. Clin. Microbiol, 2006, pp. 625-627, vol. 44 (2).

Ecker D, J. et al., "Ibis T5000: a universal biosensor approach for microbiology," Nat Rev Microbiol, 2008, pp. 553-558, vol. 6 (7).

Ecker, D. J. et al., "Rapid identification and strain-typing of respiratory pathogens for epidemic surveillance," Proc. Natl. Acad. Sci. USA, 2005, pp. 8012-8017, vol. 102 (22).

Ecker, D. J. et al., "The Ibis T5000 Universal Biosensor. An Automated Platform for Pathogen Identification and Strain Typing," JALA, 2006, pp. 341-351, vol. 11.

Edwards, K.M. et al., "Adenovirus Infections in Young Children," Pediatrics, 1985, pp. 420-424, vol. 76 (3).

Ellis et al., "Multiplex Reverse Transcription-PCR for Surveillance of Influenza A and B Viruses in England and Wales in 1995 and 1996," Journal of Clinical Microbiology, vol. 35(8), pp. 2076-2082, 1997.

Ellis, J. S. et al., "Molecular diagnosis of influenza," Rev. Med. Virol., 2002, pp. 375-389, vol. 12 (6).

Elnifro et al., "PCR and Restriction Endonuclease Analysis for Rapid Identification of AdenovirusSubgenera," Journal of Clinical Microbiology, 2000, pp. 2055-2061, vol. 38 (6).

Elsayed, S. et al., "Development and Validation of a Molecular Beacon Probe-Based Real-Time Polymerase Chain Reaction Assay for Rapid Detection of Methicillin Resistance in *Staphylococcus aureus*," Arch. Pathol. Lab. Med., 2003, pp. 845-849, vol. 127.

EMBL Accession AB068711 (May 21, 2003).

EMBL Accession AJ552897 (Mar. 29, 2003).

EMBL Accession AR321656 (Aug. 12, 2003).

EMBL Accession L15697 (Mar. 4, 2000).

EMBL Accession No. S90302, Human, Muscle, Mitochondrial Mutant, 22 nt, segment 2 of 2 (XP002436791) Nov. 26, 1993.

EMBL Accession Z48571 (Jun. 9 1995).

Enright, M. C. et al., "Multilocus Sequence Typing for Characterization of Methicillin-Resistant and Methicillin-Susceptible Clones of *Staphylococcus aureus*," J. Clin. Microbiol., 2000, pp. 1008-1015, vol. 38 (3).

Enright, M. C. et al., "Multilocus Sequence Typing of *Streptococcus pyogenes* and theRelationships between emm Type and Clone," 2001, pp. 2416-2427, vol. 69.

Enright, M. C. et al., "The evolution of a resistant pathogen—the case of MRSA," Curr. Opin.Pharmacol., 2003, pp. 474-479, vol. 3.

Enright, M. C. et al., "The evolutionary history of methicillin-resistant *Staphylococcus aureus*(MRSA)," PNAS, 2002, pp. 7687-7692, vol. 99 (11).

Enright, M.C. et al, "A multilocus sequence typing scheme for *Streptococcus pneumoniae*: identification of clones associated with serious invasive disease," Microbiology, vol. 144 (Pt 11), pp. 3049-3060, 1998.

Eremeeva et al., "Evaluation of a PCR Assay for Quantitation of Rickettsia rickettsii and Closely Related Spotted Fever Group Rickettsiae," J. Clin. Microbiol., 2003, pp. 5466-5472, vol. 41 (12).

Erlich et al., PCR Technology, 1989, Stockton Press.

Esmens et al., "Liquid Chromatography-Mass Spectrometry in Nucleoside, nucleotide and modified nucleotide characterization," J. of Chromatography A, 1998, pp. 109-127, vol. 794.

Eugene-Ruellan, et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization", Journal of Clinical Microbiology, 1998, 36 (3), 796-801.

European Application No. EP 02709785.2 filed Sep. 12, 2002, Isis Pharma.

European Patent Office Communication 94(3) EPC for 02709785.6 dated Nov. 4, 2009.

European Patent Office Communication 96(2) EPC for 02709785.6 dated Nov. 20, 2006.

European Patent Office Communication for 03814656.9 dated Sep. 5, 2006.

European Patent Office Communication for 03814656.9 dated Nov. 15, 2007.

European Patent Office Communication for 03814656.9 dated Feb. 18, 2010.

European Patent Office Communication for 03814656.9 dated Jul. 25, 2005.

European Patent Office Communication for 06849755.1 dated Mar. 12, 2008.

European Patent Office Communication for 07760292.8 dated Apr. 7, 2009.

European Patent Office Communication for EP 02709785.6 dated Aug. 5, 2010.

European Patent Office Communication for EP 03796752.8 dated Jun. 2, 2010.

European Patent Office Communication for EP 03810055.8 dated Jul. 2, 2010.
European Patent Office Communication for EP 06800205.4 dated Jun. 7, 2010.
European Patent Office Communication for EP 08730682.5 dated Feb. 6, 2010.
European Search Report for 02709785.6 dated Oct. 10, 2005.
European Supplemental Search Report for 02709785.6-2405 (PCT/US02/06763) dated Oct. 12, 2005.
European Supplemental Search Report for 03796752.8 dated Aug. 14, 2007, 3 Pages.
European Supplemental Search Report for 03810055.8 dated Jul. 9, 2007.
European Supplemental Search Report for 04752257.8 dated Feb. 15, 2006.
European Supplemental Search Report for 04775904.8 dated Jul. 25, 2008.
European Supplemental Search Report for 05751872.2 dated Jan. 28, 2008.
European Supplemental Search Report for 05753037 dated Aug. 28, 2009.
European Supplemental Search Report for 05856582.1 dated Nov. 10, 2008.
Evans et al., "Practical Algorithms for Universal DNA Primer Design: An Exercise in Algorithm Engineering, In N. El-Mabrouk, T. Lengauer, and D. Sankoff (eds.)", Currents in Computational Molecular Biology, 2001, pp. 25-26.
Facklam, R., et al., "emm Typing and Validation of Provisional M Types for Group A Streptococci," j Clin. Microbiol, 1999, pp. 247-253, vol. 5.
Fang, H. et al., "Rapid Screening and Identification of Methicillin-Resistant *Staphylococcus aureus* from Clinical Samples by Selective-Broth and Real-Time PCR Assay," journal of clinical microbiology, 2003, pp. 2894-2899, vol. 41 (7).
Farlow et al., "*Francisella tularensis* Strain Typing Using Multiple-Locus, Variable-Number Tandem Repeat Analysis", Journal of Critical Microbiology, 2001, pp. 3186-3192, vol. 39 (9).
Farrell, D. J., "The Reliability of Microscan Conventional and Rapid Panels to Identify *Staphylococcus aureus* and Detect Methicillin Resistance: an Evaluation Using the Tube Coagulase Test and mecA PCR," Pathology, 1997, pp. 406-410, vol. 29.
Fedele C G et al., "Multiplex polymerase chain reaction for the simultaneous detection and typing of polyomavirus JC, BK and SV40 DNA in clinical samples," Journal of Virological Methods, 1999, pp. 137-144, vol. 82 (2).
Fedele C G et al., "Quantitation of polyomavirus DNA by a competitive nested polymerase chair reaction," Journal of Virological Methods, 2000, pp. 51-61, vol. 88 (1).
Feng, P., "Impact of molecular biology on the detection of food pathogens," Mol. Biotechnol, 1997, pp. 267-278, vol. 7.
Figueiredo, et al., "Identification of Brazilian Flavivirus by a simplified reverse transcription-polymerase chain reaction method using Flavivirus universal primers," Am. J. Trop. Med. Hyg, 1998, pp. 357-362, vol. 59 (3).
Final Office Action for U.S. Appl. No. 10/943,344, mailed Sep. 8, 2010.
Final Office Action mailed Feb. 18, 2010, for U.S. Appl. No. 10/754,415 filed Jan. 9, 2004.
Final Office Action mailed May 12, 2010, for U.S. Appl. No. 11/674,538 filed Feb. 13, 2007.
Final Office Action mailed Jul. 8, 2010, for U.S. Appl. No. 12/326,800 filed Dec. 2, 2008.
Final Office Action mailed Nov. 3, 2008, for U.S. Appl. No. 10/728,486 filed Dec. 5, 2003.
Final Office Action mailed Nov. 17, 2009, for U.S. Appl. No. 11/582,875 filed Oct. 17, 2006.
Final Office Action mailed Jul. 13, 2010, for U.S. Appl. No. 11/929,930, filed Oct. 30, 2010.
Final Office Action mailed Jun. 23, 2010, for U.S. Appl. No. 11/930,017, filed Oct. 30, 2007.

Flora. et al., "Dual-micro-ESI source for precise mass determination on a quadrupole time-of-flight mass spectrometer for genomic and proteomic app.lications," Anal. Bioanal. Chem, 2002, pp. 538-546, vol. 373 (7).
Fong, W. K., et al., "Rapid Solid-Phase Immunoassay for Detection of Methicillin-ResistantStaphylococcus aureus Using Cycling Probe Technology," J. Clin. Microbiol., 2000, pp. 2525-2529, vol. 38 (7).
Fox, A. et al., "Identification and detection of bacteria: electrospray MS-MS versus derivatization/GC-MS," Proceedings of the ERDEC Scientific Conference on Chemical and Biological Defense Research (1996) Aberdeen Proving Ground, Md, 1994, pp. 39-44.
Fox et al., "Identification of Brucella by ribosomal-spacer-region PCR and differentiation of Brucell canis from other Brucella spp.. pathogenic for humans by carbohydrate profiles," J. Clin. Microbiol, 1998, pp. 3217-3222, vol. 36 (11).
Fox et al., "Report of the Bioterrorism Workshop," J. Microbol. Methods, 2002, pp. 247- 254, vol. 51 (3).
Fox, J.P. et al., "The Virus Watch Program: A Continuing Surveillance of Viral Infections in Metropolitan New York Families," Am. J. Epidemiol, 1969, pp. 25-50, vol. 89 (1).
Francois et al., "Sequence-specific recognition and cleavage of duplex DNA via triple-helix formation by oligonucleotides covalently linked to a phenanthroline-copper chelate," Proc. Natl. Acad. Sci. USA, 1989, pp. 9702-9706, vol. 86.
Francois, P. et al., "Rapid Detection of Methicillin-Resistant *Staphylococcus aureus* Directly from Sterile or Nonsterile Clinical Samples by a New Molecular Assay," J. Clin. Microbiol., 2003, pp. 254-260, vol. 41 (1).
Fraser et al., "The mimimal gene complement of *mycoplasma genitalium*," Science, 1995, pp. 397-403, vol. 270.
Freiberg et al., "Genome-wide mRNA profiling: impact on compound evaluation and target identification in anti-bacterial research," Targets, 2002, pp. 20-29, vol. 1 (1).
Freymuth, F. et al., "Comparison of Multiplex PCR Assays and Conventional Techniques for the Diagnostic of Respiratory Virus Infections in Children Admitted to Hospital With an Acute Respiratory Illness" J. Med. Virol., 2006, pp. 1498-1504, vol. 78 (11).
Freymuth, F. et al., "Detection of respiratory syncytial virus, parainfluenzavirus 3, adenovirus andrhinovirus sequences in respiratory tract of infants by polymerase chain reaction and hybridization," Clin. Dian. Virol, 1997, pp. 31-40, vol. 8.
Fuerstenau et al.,, "Molecular Weight Determination of Megadalton DNA Electrospray Ions UsingCharge Detection Time-of-flight Mass Spectrometry," Rapid Comm. Mass Spec., 1995, pp. 1528-1538, vol. 9.
Fujimoto, T. et al., "Single-Tube Multiplex. PCR for Rapid and Sensitive Diagnosis of Subgenus B and Other Subgenera Adenoviruses in Clinical Samples," Microbial. Immunol, 2000, pp. 821-826, vol. 44 (10).
Fujimura, S. et al., "Characterization of the mupA Gene in Strains of Methicillin-Resistant *Staphylococcus aureus* with a Low Level of Resistance to Mupirocin," Antimicrob. Agents Chemother, 2001, pp. 641-642, vol. 45 (2).
Fujimura, S. et al., "Isoleucyl-tRNA Synthetase Mutations in *Staphylococcus aureus* ClinicalIsolates and In Vitro Selection of Low-Level Mupirocin-Resistant Strains," Antimicrob. Agents Chemother, 2003, pp. 3373-3374, vol. 47 (10).
Fujioka et al., "Analysis of enterovirus genotypes using single-strand conformation polymorphismsof polymerase chain reaction product," J. Virol. Meth., 1995, pp. 253-258, vol. 51.
Gabriel Matthew N et al., "Improved mtDNA sequence analysis of forensic remains using a "mini-primer set" amplification strategy," Journal of Forensic Sciences, 2001, pp. 247-253, vol. 46 (2).
Gall, J. G. D. et al., ,"Construction and Characterization of Hexon-Chimeric Adenoviruses: Specification of Adenovirus Serotype," J. Viral, 1998, pp. 10260-10264, vol. 72 (12).
Gammelin et al., "Two Subtypes of Nucleoproteins (NP) of Influenza A Viruses," Virology, 1989, pp. 71-80, vol. 170 (1).
Garcia et al., "Quantitative Real-Time PCR Detection of Rift Valley Fever Virus and Its Application toEvaluation of Antiviral Compounds," J. Clin. Microbiol, 2001, pp. 4456-4461, vol. 39 (12).

Garcia-Martinez et al., "Use of the 16s-23s ribosomal genes spacer region in studies of prokaryotic diversity", Journal of Microbiological Methods, 1999, pp. 55-64, vol. 36.

Gatiermann, N. et al., "Heteroplasmic Point Mutations of Mitochondria! DNA Affecting Subunit I of Cytochrome c Oxidise in Two Patients with Acquired Idiopathic Siderblastic Anemia," Blood, 1997, pp. 4961-4972, vol. 90 (12).

Gaydos, C.A. et al., "Adenovirus Vaccines in the U.S. Military," Military Med, 1995, pp. 300-304, vol. 160 (6).

Geha et al., "Multiplex PCR for Identification of Methicillin-Resistant Staphylococci in the Clinical Laboratory," J. Clin. Microbiol, 1994, pp. 1768-1777, vol. 32.

GenBank Accession AF304460 (Jul. 11, 2001).

GenBank Accession No. AE009948.1 (gi:22535226, Aug. 8, 2002).

GenBank Accession No. AE009949.1 (gi:19913450; Apr. 3, 2002).

GenBank Accession No. AE015927.1 (gi:28204652; Feb. 4, 2003).

GenBank accession No. AE015929.1 (qi:27316888; Jan. 2, 2003).

GenBank Accession No. AF274728 (gi:11612419; Dec. 11, 2000).

GenBank accession No. AF276257.1 (gi:1457889; Jul. 1, 2001).

GenBank Accession No. AF375051.1 (Jun. 26, 2001).

GenBank Accession No. BX571857.1 (gi:49243355; Jun. 25, 2004).

GenBank Accession No. M21150 Apr. 26, 1993.

GenBank Accession No. M21150 Apr. 29, 1993.

GenBank Accession No. NC_000913; *Escherichia coli* str. K-12 substr. MG1655, complete genome. (Oct. 15, 2001).

Genbank accession No. X84646 [online], publicly available Jul. 2, 1995 [retrieved on Apr. 15, 2009], retrieved from: http://www.ncbi.nlm.nih.gov/nuccore/886486?report=genbank (4 pages total).

Genbank accession No. Z48571 [online], publicly available Jun. 9 1995 [retrieved on May 11, 2008], retrieved from: http://www. ncbi.nlm.nih.gov/entrez/viewer.fcgi?861019:OLDI D:1560364.

GenBank GI:147581 [online] Sep. 14, 1992 [retrieved on Jul. 20, 2009] from http://www.ncbi.nlm.nih.gov/sviewer/viewerfcgi?147581:OLDID:114614.

GenBank GI:15922990 [online] Oct. 4, 2001 [retrieved on Jun. 22, 2008] retrieved from: http://www.ncbi.nlm.nih.gov/entrez/viewer.fcgi?15922990:OLD08:50885 (pp. 1, 12, 15, 148, 216, 476, 722, 723, 725, 881, 958, 1251).

GenBank GI:174375 [online] Aug. 11, 1995 [retrieved on Jul. 20, 2009] retrieved from http://www.ncbi.nlm.nih.gov/nuccore/174375.

GenBank Gi:18542231 [online] Sep. 16, 2003 [retrieved on Jun. 23, 2008] retrieved fromhttp://www.ncbi.nlm.nih.gov/entrez/viewer.fcgi?db=nuccore&id=18542231 (2 pages).

Genbank GI:21281729 [online], publicly available at least as of May 31, 2002 retrieved on Apr. 11,20081, retrieved from: http://www.ncbi.nlm.nih.gov/entrez/viewer.fcgi?21281729:0LD11:599579 (pp. 1, 723 and 1137).

GenBank GI:42813 [online] Feb. 28, 1992 [retrieved on Jul. 20, 2009] retrieved from the Internet at http://www.ncbi.nlm.nih.gov/sviewer/viewer.fcgi?42813:OLDID:25896.

GenBank GI:49243355 [online] Jun. 24, 2004 [retrieved on Jul. 27, 2009] retrieved from http://www. ncbi.nlm.n i h.govlsviewer/viewerfi?49243355:OLD04:1481434, 4 Pages.

GenBank GI:73916349 [online] Sep. 30, 2005 [retrieved on Jul. 25, 2009] retrieved from http://www. ncbi.nlm.n i h.gov/nuccore/73916349.

GenBank GI:78099429 [online] Mar. 11, 2006 [retrieved on Jul. 22, 2009] retrieved from http://www.ncbtnlm .nih.gov/sviewer/viewerfi?78099429:NCBI:12971731.

Gendel et al., "Computational analysis of the specificity of 16S rRNA-derived signature sequencesfor identifying food-related microbes," Food Microbiology, 1996, pp. 1-15, vol. 13.

Gibb et al., "Development and evaluation of a 5' fluorogenic nuclease assay to detect and differentiate between Ebola Virus subtypes Zaire and Sudan," Journal of Clinical Microbiology, 2001, pp. 4125-4130, vol. 39 (11).

Gilbert et al., "Comparison of commercial assays for the quantitation of HBV DNA load in healthcare workers: calibration differences," J. Virol. Methods, 2002, pp. 100(1-2), vol. 37-47.

Giles et al., "Maternal inheritance of human mitochondrial DNA," PNAS, 1980, pp. 6715-6719, vol. 77.

Gill, S. R. et al., "Insights on Evolution of Virulence and Resistance from the Complete GenomeAnalysis of an Early Methicillin-Resistant *Staphylococcus aureus* Strain and a Biofilm-ProducingMethicillin-Resistant *Staphylococcus epidemidis* Strain," J. Bacte.

Gilliland et al., "Analysis of cytokine mRNA and DNA: detection and quantitation by competitive polymerase chain reaction," PNAS, 1990, pp. 2725-2729, vol. 87 (7).

Ginther et al., "Identifying individuals by sequencing mitochondrial DNA from teeth," Nature Genetics, 1992, pp. 135-138, vol. 2.

Gjoen et al., "Specific detection of coxsackie viruses A by the polymerase chain reaction," Clinicaland Diagnostic Virology, 1997, pp. 183-188, vol. 8.

Golden, M. R. et al., "Pilot Study of COBAS PCR and Ligase Chain Reaction for Detection of Rectal Infections Due to *Chlamydia trachomatis*," J. Clin. Microbial., 2003, pp. 2174-2175, vol. 41 (5).

Goto et al., "Applications of the partial 16S rDNA sequence as an index for rapid identification of species in the genus Bacillus," J. Gen. Appl. Microbiol., 2000, pp. 1-8, vol. 46.

Gravet, A. et al., "Characterization of a novel structural member, LukE-LukD, of the bi-component *staphylococcal leucotoxins* family," FEBS Lett, 1998, pp. 202-208, vol. 436 (2).

Gray, G. C. et al., "Adult Adenovirus Infections: Loss of Orphaned Vaccines Precipitates Military Respiratory Disease Epidemics," Clin. Infect. Diseases, 2000, pp. 663-670, vol. 31.

Greenberg et al., "Intraspecific nucleotide sequence variability surrounding the origin of replicationin human mitochondria! DNA," Gene, 1983, pp. 33-49, vol. 21.

Griffey R.H. et al., "Detection of base pair mismatches in duplex DNA and RNA oligonudeotides using electrospray mass spectrometry," Proceedings of SPIE—The International Society for Optical Engineering (Ultrasensitive Biochemical Diagnostics II), 1997, pp. 82-86, vol. 2985.

Griffin. et al., "Direct genetic analysis by matrix-assisted laseer desorption/ionization mass spectrometry," proc. Nall. Acad. Sci. USA, 1999, pp. 6301-6306, vol. 96 (11).

Griffin, T. J. et al., "Single-nucleotide polymorphism analysis by MALDI-TOF mass spectrometry," Trends in Biotechnology, 2000, pp. 77-84, vol. 18 (2).

Grondahl, B. et al., "Rapid Identification of Nine Microorganisms Causing Acute Respiratory TractInfections by Single-Tube Multiplex Reverse Transcription-PCR: Feasibility Study," J. Clin. Microbiol, 1999, pp. 1-7, vol. 37 (1).

Grundmann, H. et al., "Emergence and resurgence of meticillin-resistant *Staphylococcus aureus* as a public-health threat," Lancet, 2006, pp. 874-885, vol. 368.

Grzybowski Tomasz et al., "Extremely high levels of human mitochondrial DNA heteroplasmy in single hair roots," Electrophoresis, 2000, pp. 548-553, vol. 21 (3).

Gu, Z et al., "Multiplexed, Real-Time PCR for Quantitative Detection of Human Adenovirus," J. Clin. Microbiol, 2003, pp. 4636-4641, vol. 41 (10).

Guatelli et al., "Nucleic Acid Amplification In Vitro: Detection of Sequences with Low Copy Numbers and Application to Diagnosis of Human Immunodeficiency Virus Type 1 Infection," Clin. Microbiol. Rev, 1989, pp. 217-226, vol. 2 (2).

Haff L A et al., "Multiplex Genotyping of PCR Products With Mass Tag-Labeled Primers," Nucleic Acids Research, Oxford University Press, Surrey, GB,, 1997, pp. 3749-3750, vol. 25 (18).

Haines, J.D., et al., "Medical response to bioterrorism: Are we prepared," J. Okla. State Med. Assoc, 2000, pp. 187-196, vol. 93.

Hall et al., "Base composition analysis of human mitochondrial DNA using electrospray ionization mass spectrometry: a novel tool for the identification and differentiation of humans," Analytical Biochemistry, 2005, pp. 53-69, vol. 344.

Hamdad, F. et al., "Detection of Methicillin/Oxacillin Resistance and Typing in Aminoglycoside-Susceptible Methicillin-Resistant and Kanamycin-Tobramycin-Resistant Methicillin-Susceptible," Microbial Drug Resistance, 2006, pp. 177-185, vol. 12 (3).

Hamels, S. et al., "Consensus PCR and Microarray for Diagnosis of the Genus *Staphylococcus*, Species, and Methicillin Resistance.," Biotechniques, Informa Life Sciences Publishing, Westborough, MA, US, 2001, pp. 1364-1366,1368, vol. 31 (6).

Hammerle et al., "A sensitive PCR assay system for the quantitation of viral genome equivalents:hepatitis C virus (HCV)," Arch. Virol, 1996, pp. 2103-2114, vol. 141.

Hannis and Muddiman, "Accurate characterization fo the tyrosine hydroxylase forensic allele 9.3 through development of electrospray ionization Fourier transform ion cyclotron resonance mass spectrometry," Rapid. Comm. Mass Spectrom, 1999, pp. 954-962, vol. 13 (10).

Hannis and Muddiman, "Detection of double-stranded PCR amplicons at the attomole level electrosprayed from low nanomolar solutions using FT-ICR mass spectrometry," Fresenius J. Anal Chem, 2001, pp. 246-251, vol. 369 (3-4).

Hannis and Muddiman, "Genotyping short tandem repeats using flow injection and electrospray ionization , Fourier transform ion cyclotron resonance mass spectrometry," Rapid. Comm. Mass Spectrom, 2001, pp. 348-350, vol. 15 (5).

Hannis, et al., "Genotyping complex short tandem repeats using electrospray ionzation Fourier transform ion cyclotron resonance multi-stage mass spectrometry," SPIE, 2000, pp. 36-47,vol. 3926.

Hannis et al., "Nanoelectrospray Mass Spectrometry Using Non-Metalized, Tapered (50-10 .mu.m) Fused-silica Capillaries," Mass Spectrom., 1998, pp. 443-448, vol. 12.

Hanssen, a. M. et al., "SCCmecin staphylococci: genes on the move," FEMS Immuol. Med Microbiol, 2006, pp. 8-20, vol. 46.

Hasebe, F. et al. , "Combined Detection and Genotyping of Chikungunya Virus by a Specific Reverse Transcription-Polymerase Chain Reaction," J. Med. Virol, 2002, pp. 370-374, vol. 67 (3).

Hassan et al., "Inter- and Intraspecies Variations of the 16S-23S rDNA Intergenic Spacer Region ofVarious Streptococcal Species," Systematic and Applied Microbiology, 2003, pp. 97-103, vol. 26 (1).

Haugland et al., "Identification of putative sequence specific PCR primers for detection of the toxygenic fungal species *Stachybotrys chartarum*," Mol. Cell. Probes, 1998, pp. 387-396, vol. 12.

Hayashi. et al., "Phylogenetic analysis of the human gut microbiota using 16S rDNA clone libraries and strictly anaerobic culture-based methods," Microbiol. Immunol., 2002, pp. 535-548, vol. 46 (8).

Heim, A. et al., "Rapid and Quantitative Detection of Human Adenovirus DNA by Real-Time PCR," J. Med. Viral, 2003, pp. 228-239, vol. 70.

Henchal, et al., "Sensitivity and specificity of a universal primer set for the rapid diagnosis of dengue virus infections by polymerase chain reaction and nucleic acid hybridization," Am. J. Trop. Med. Hyg, 1991, pp. 418-428, vol. 45 (4).

Herrmann, B. et al., "Differentiation of Chiamydia spp. by Sequence Determination and Restriction Endonuclease Cleavage of RNase P RNA Genes," J. CM. Microbiol, 1996, pp. 1897-1902, vol. 34 (8).

Higgins, et al., "Competitive oligonucleotide single-base extension combined with mass spectrometric detection for mutation Screening," Biotechniques, 1997, pp. 710-714, vol. 23 (4).

Higgins, J.A., et al., Ann. NY Acad. Sci., 1999, vol. 894, pp. 130-148.

Higgins, J.A., et al., "Sensitive and Rapid Identification of Biological Threat Agents", Ann. NY Acad. Sci., 1999, pp. 130-148, vol. 894.

Hill, F., et al., "Polymerase recognition of synthetic oligodeoxyribonucleotides incorporating degenerate pyrimidine and purine bases," Proc. Natl. Acad. Sci. USA, 1998, pp. 4258-4263, vol. 95.

Hiramatsu, K. et al., "The emergence and evolution of methicillin-resistant *Staphylococcusaureus*," Trends Microbiol, 2001, pp. 486-493, vol. 9 (10).

Hodgson et al., "Molecular Characterization of the Gene Encoding High-Level Mupirocin Resistancein *Staphylococcus aureus* J2870.," Antimicrobial Agents and Chemotherapy, 1994, pp. 1205-1208, vol. 38 (5).

Hoffman et al., "Rescue of influenza B virus from eight plasmids," PNAS, 2002, pp. 11411-11416, vol. 99 (17).

Hoffmann. et al., "Universal primer set for the full-length amplification of all influenza A viruses," Arch. Virol, 2001, pp. 2275-2289, vol. 146 (12).

Hofstadler et al., "Tiger: the universal biosensor," Inter. J. Mass Spectrom., 2005, pp. 23-41, vol. 242.

Holden, M. T. G. et al., "Complete genomes of two clinical *Staphylocuccus aureus* strain: Evidencefor the rapid evolution of virulence and drug resistance," PNAS, 2004, pp. 9786-9791, vol. 101 (26).

Holland et al., "Mitochondria! DNA Sequence Analysis of Human Skeletal Remains: Identification of Remains from the Vietnam War," Journal of Forensic Sciences, 1993, pp. 542-553, vol. 38.

Holland, M.M. et al., "Mitochondrial DNA analsysis_Validation and use for forensic casework," Forensic Science Review, 1999, pp. 25-51, vol. 11.

Holm et al., "Removing near-neighbour redundancy from large protein sequence collections," Bioinformatics, 1998, pp. 423-429, vol. 14.

Holmes, E. C. et al., "Whole-Genome Analysis of Human Influenza A Virus Reveals Multiple Persistent Lineages and Reassortment among Recent H3N2 Viruses," PLoS Biol, 2005, pp. 1579-1589, vol. 3 (9).

Honda. et al., "Universal method of hypersensitive nested PCR toward forensic DNA typing," International Congress Series, 1998, pp. 28-30, vol. 7.

Hongoh, et al., "Evaluation of primers and PCR conditions for the analysis of 16s rRNA genes from a naturalenvironment," FEMS Microbiol. Lett, 2003, pp. 299-304, vol. 221.

Hood, E. et al, "Chemical and biological weapons: New questions, new answers," Environ. HealthPerspect., 1999, pp. 931-932, vol. 107.

Houng, H.-S. H. et al., "Rapid type-specific diagnosis of adenovirus type 4 infection using a hexon- based quantitative fluorogenic PCR," Diagn. Microbiol. Infect. Dis., 2002, pp. 227-236, vol. 42.

Howell N et al., "Persistent heteroplasmy of a mutation in the human mtDNA control region: Hypermutation as an apparent consequence of simple-repeat expansion/contraction.," Am J Hum Genet., 2000, pp. 1589-1598, vol. 66.

Huletsky, A. et al., "New real-time PCR assay for rapid detection of methicillin-resistantStaphylococcus aureus directly from specimens containing a mixture of staphylococci.," J. Clin.Microbial., 2004, pp. 1875-1884, vol. 42 (5).

Hunag, C. et al., "Detection of arboviral RNA directly from mosquito homogenates by reverse transcription-polymerase chain reaction," J. Virol. Methods, 2001, pp. 121-128, vol. 94 (1-2).

Hung, "Detection of SARS coronavirus RNA in the cerebrospinal fluid of a patient with severe acute respiratory syndrome," Clin. Chem., 2003, pp. 2108-2109, vol. 49.

Hurdle, J. G. et al., "Analysis of Mupirocin Resistance and Fitness in *Staphylococcus aureus* by Molecular Genetic and Structural Modeling Techniques," Antimicrob. Agents Chemother, 2004, pp. 4366-4376, vol. 48 (11).

Hurst et al., "MALDI-TOF of Analysis of Polymerase Chain Reaction Products from Methanotrophic Bacteria," Anal. Chem, 1998, pp. 2693-2698, vol. 70 (13).

Hurst, G.B., et al., "Detection of bacterial DNA polymerase chain reaction products by matrix-assisted laser desorptionfionization mass spectrometry," Rapid Commun. Mass Spec, 1996, pp. 377-382, vol. 10.

Hutchison et al., "Maternal inheritance of mammalian mitochondrial DNA," Nature, 1974, pp. 536-538, vol. 251.

Hyde-Deruyscher, R. et al., "Polyomavirus early-late switch is not regulated at the level of transcription initiation and is associated with changes in RNA processing," Proc. Natl. Acad. Sci. USA, 1988, pp. 8993-8997, vol. 85.

Ieven, M. et al., "Rapid Detection of Methicillin Resistance in Coagulase-Negative Staphylococci by Commercially Available Fluorescence Test," J. Clin. Microbiol., 1995, pp. 2183-2185, vol. 33 (8).

Ihle et al., "Efficient purification of DNA fragments using a protein binding membrane," Nucleic AcidsResearch, 2000, pp. e76, vol. 28.

Inglis, T. J. et al., "Rapid Genotypic Confirmation of Methicillin Resistance," Pathology, 1996, pp. 259-261, vol. 28 (3).

Ingman et al., "Mitochondrial genome variation and the origin of modern humans," Nature, 2000, pp. 708-713, vol. 408.

International Prelim. Exam. Report for PCT/US2005/033707 dated Mar. 20, 2007.

International Preliminary Examination Report for PCT/US02/20336 dated May 12, 2004.

International Search Report for application No. PCT/US02/06763, Mailed on Oct. 23, 2002, 4 pages.

International Search Report for application No. PCT/US02/20336, Mailed on Mar. 2, 2003, 3 pages.

International Search Report for application No. PCT/US03/22835, Mailed on Dec. 12, 2003, 1 pages.

International Search Report for application No. PCT/US03/38505, Mailed on Dec. 4, 2005, 2 pages.
International Search Report for application No. PCT/US03/38757, Mailed on Jun. 6, 2004, 2 pages.
International Search Report for application No. PCT/US03/38795, Mailed on Apr. 19, 2004, 2 pages.
International Search Report for application No. PCT/US03/38830, Mailed on Aug. 8, 2004, 3 pages.
International Search Report for application No. PCT/US04/033742, Mailed on May 5, 2006, 2 pages.
International Search Report for application No. PCT/US05/018031, Mailed on Jul. 28, 2006, 5 pages.
International Search Report for application No. PCT/US06/015160, Mailed on Oct. 10, 2006, 4 pages.
International Search Report for PCT/US02/20336 dated Feb. 3, 2003.
International Search Report for PCT/US02/20336 dated May 12, 2004.
International Search Report for PCT/US03/009802 dated Aug. 20, 2004.
International Search Report for PCT/US03/38505 dated Apr. 12, 2005.
International Search Report for PCT/US03/38757 dated Jun. 24, 2004.
International Search Report for PCT/US03/38761 dated Dec. 30, 2005, 5 pages.
International Search Report for PCT/US03/38795 dated Apr. 19, 2004.
International Search Report for PCT/US03/38830 dated Aug. 25, 2004.
International Search Report for PCT/US05/005356 dated Aug. 7, 2007.
International Search Report for PCT/US05/007022 dated Oct. 20, 2006.
International Search Report for PCT/US05/018337 dated Oct. 10, 2006.
International Search Report for PCT/US05/024799 dated Dec. 28, 2006.
International Search Report for PCT/US05/030058 dated Aug. 20, 2007.
International Search Report for PCT/US05/033707 dated Feb. 6, 2006.
International Search Report for PCT/US05/06133 dated Jul. 26, 2007.
International Search Report for PCT/US05/09557 dated Sep. 19, 2005.
International Search Report for PCT/US2004/011877 dated Apr. 20, 2006.
International Search Report for PCT/US2004/028869 dated Jul. 17, 2006.
International Search Report for PCT/US2005/000386 dated May 9, 2006, 3 Pages.
International Search Report for PCT/US2005/018031 dated Jun. 28, 2006.
International Search Report for PCT/US2006/040747 dated Mar. 17, 2009.
International Search Report for PCT/US2007/020045 dated Mar. 26, 2009.
International Search Report for PCT/US2008/057717 dated Jan. 13, 2009.
International Search Report for PCT/US2008/057901 dated Jun. 29, 2009.
International Search Report for PCT/US2008/064891 dated Aug. 28, 2008.
International Search Report for PCT/US2008/065332 dated Nov. 28, 2008.
International Search Report for PCT/US04/007236 dated Feb. 24, 2006.
International Search Report for PCT/US04/012671 dated Sep. 28, 2007.
International Search Report for PCT/US04/015123 dated Oct. 3, 2005.
International Search Report for PCT/US04/015196 dated Jul. 1, 2005.
International Search Report for PCT/US04/033742 dated May 15, 2006.
Inyaku, K. et al., "Rapid Detection and Identification of Mycobacteria in Sputum Samples by NestedPolymerase Chain Reaction and Restriction Fragment Length Polymorphisms of dnaJ Heat ShockProtein Gene," J. Med. Sci., 1993, pp. 21-31, vol. 42.
Iqbal et al., "A review of molecular recognition technologies for detection of biological threat agents," Biosensors & Bioelectronics, 2000, pp. 549-578, vol. 15.
Isola. et al., "MALDI-TOF mass spectrometric method for detection of hybridized DNA oligomers," Anal. Chem, 2001, pp. 2126-2131, vol. 73 (9).
Ito, T. et al., "Insights on antibiotic resistance of *Staphylococcus aureus* from its whole genome: genomic island SCC," Drug Resist. Updat., 2003, pp. 41-52, vol. 6 (1).
Ito, T. et al., "Structural Comparison of Three Types of Staphylococcal Cassette Chromosome mecIntegrated in the Chromosome in Methicillin-Resistant *Staphylococcus aureus*," Antimicrob. AgentsChemother, 2001, pp. 1323-1336, vol. 45 (5).
Jackson et al., "Mass spectrometry for genotyping: an emerging tool for molecular medicine," Molecular Medicine Today, 2000, pp. 271-276, vol. 6.
Jambrina et al., "GenBank: AF005737.1 influenza B virus B/Panama/45/90 polymerase (PB2)mRNA, complete cds," 1997, pp. 1-3.
James et al., "Borelia lonestari infection after a bite by an *Amblyomma americanum* tick", The Journal of Infectious Diseases, 2001, pp. 1810-1814, vol. 183.
Jankowski, K. et al., "Mass spectrometry of DNA. Part 2 Quantitative estimation of base composition," European Journal of Mass Spectrometry in Biochemistry, Medicine, and Environmental Research, 1980, pp. 45-52, vol. 1 (1).
Jansen et al., "Genotype-by-environment Interaction in Genetic Mapping of Multiple Quantitative Trait Loci," Theor. Appl. Genet, 1995, pp. 33-37, vol. 91.
Japanese Patent office communication for Application No. JP2005508560 dated Nov. 16, 2009.
Japanese Patent office communication for Application No. JP2006533082 dated Nov. 25, 2009.
Jaulhac, B. et al., "Specific detection of the toxic shock syndrome toxin-1 gene using the polymerase chain reaction," Mol. Cel. Probes, 1991, pp. 281-284, vol. 5.
Jaulhac, B. et al., "Synthetic DNA probes for detection of genes for enterotoxins A, B, C, D, E andfor TSST-1 in staphylococcal strains," J. Appl. Bacterial., 1992, pp. 386-392, vol. 72 (5).
Jensen, M. A. et al., "Rapid Identification of Bacteria on the Basis of Polymcrase Chain Reaction-Amplified Ribosomal DNA Spacer Polymorphisms," Appl. Environ. Microbiol., 1993, pp. 945-952, vol. 59 (4).
Jeong, J. et al., "Early Screening of Oxacillin-Resistant *Staphylococcus aureus* and *Staphylococcus epidermidis* from Blood Culture," J. Korean Med. Sci, 2002, pp. 168-172, vol. 17.
Jiang et al., "Multiple Trait Analysis of Genetic Mapping for Quantitative Trait Loci Genetics," Genetics, 1995, pp. 1111-1127, vol. 140.
Johansson et al., "Evaluation of PCR-based methods for discrimination of *Francisella* species and subspecies and development of a specific PCR that distinguishes the two major subspecies of *Francisella tularensis*", Journal of Clinical Microbiology, 2000, 38, 4180-4185.
Johnson et al., "Detection of genes for enterotoxins, exfoliative toxins, and toxic shock Syndrome toxin 1 in *Staphylococcus aureus* by the polymerase chain reaction," J. Clin. Microbiol., 1991, pp. 426-430, vol. 29.
Johnson, Y.A et al., "Precise molecular weight determination of PCR products of the rRNA intergenic spacer region using electrospray quadrupole mass spectrometry for differentiation of *B. subtilis* and *B. atrophaeus*, closely related species of bacilli," JO.
Jonas, D. et al., "Rapid PCR-Based Identification of Methicillin-Resistant *Staphylococcus aureusfrom* Screening Swabs," J. Clin. Microbiol, 2002, pp. 1821-1823, vol. 40 (5).
Jurinke C et al., "Application of nested PCR and mass specctrometry for DNA based virus detection: HBV-DNA detected in the majority of isolated anti-Hbc positive sera," Genetic Analysis: Biomolecular Engineering, Elsevier Science Publishing, US, 1998, pp.

Jurinke et al., "Detection Of Hepatitis B: Virus DNA in Serum Samples Via Nested PCR And MALDI-TOF MassSpectrometry," Genetic Analysis: Biomolecular Engineering, 1996, pp. 67-71, vol. 13.

Jurinke et al., "MALDI-TOF Mass Spectrometry. A Versatile Tool for High- Performance DNA Analysis," Molecular Biotechnology, 2004, pp. 147-163, vol. 26 (2).

Kacian et al., "A Replicating RNA Molecule Suitable for a Detailed Analysis of Extracellular Evolution and Replication," Proc. Natl. Acad. Sci. USA, 1972, pp. 3038-3042, vol. 69.

Kageyama and Benno, "Rapid detection of human fecal Eubacterium species and related genera by tested PCR method," Microbiol. Immunol, 2001, pp. 315-318, vol. 45 (4).

Kajon, A.E. et al., "Genome Type Analysis of Brazilian Adenovirus Strains of Serotypes 1, 2, 3, 5,and 7 Collected Between 1976 and 1995," J. Med. Virol, 1999, pp. 408-412, vol. 58.

Katano H et al., "Identification of Adeno-Associated Virus Contamination in Cell and Virus Stocks by PCR," Biotechniques, Informa Life Sciences Publishing, Westborough, MA, US, 2004, pp. 676-680, vol. 36 (4).

Katayama, Y. et al., Genetic Organization of the Chromosome Region Surrounding mecA inClinical Staphylococcal Strains: Role of IS431-Mediated mecl Deletion in Expression of Resistance inmed-Canying, Low-Level Methicillin-Resistant *Staphylococcus haemoly*.

Ke et al., "Development of a PCR Assay for Rapid Detection of Enterococci," Journal of Clinical Microbiology, 1999, pp. 3497-3503, vol. 37.

Kearns, A. M. et al., "Rapid detection of methicillin-resistant staphylococci by multiplex PCR," J.Hosp. Infect, 1999, pp. 33-37, vol. 43.

Keller et al., "Empirical Statistical Model to Estimate the Accuracy of Peptide Identifications Made by MS/MS and Database Search," Anal. Chem, 2002, pp. 5383-5392, vol. 74.

Khan, A.S., et al., "An outbreak of Crimean-Congo haemorrhagic fever in the United Arab Emirates, 1994-1995," Am. J. Trop. Med. Hyg, 1997, pp. 519-525, vol. 57.

Khan, S. A. et al., "Simultaneous detection of erythromycin-resistant methylase genes ermA andermC from Staphylococcus spp. By multiplex-PCR," Mol. Cell Probes, 1999, pp. 381-387, vol. 13.

Kidd, A. H. et al., "Rapid Subgenus Identification of Human Adenovirus Isolates by a General PCR," J. Clin. Microbiol., 1996, pp. 622-627, vol. 34 (3).

Kidd-Ljunggren, et al., "The hepatitis B virus X gene: analysis of functional domain variation and gene phylogeny using multiple sequences", Journal of General Virology, 1995, 76, 2119-2130.

Kilbourne, E. D., "Influenza Pandemics of the 20th Century," Emerg. Infect. Dis., 2006, pp. 9-14, vol. 12 (1).

Kilbourne, E. D., "influenza Pandemics: Can We Prepare for the Unpredictable," Viral Immunol., 2004, pp. 350-357, vol. 17 (3).

Kilpatrick et al., "Group-Specific Identification of Polioviruses by PCR Using Primer Containing Mixed- Base or Deoxyinosine Residues at Positions of Codon Degeneracy," J. Clin. Microbiol., 1996, pp. 2990-996, vol. 34.

Kim et al., "Identification of Mycobacterial species by comparative sequence analysis of the RNA polymerase gene (rpoB)," Journal of Clinical Microbiology, 1999, pp. 1714-1720, vol. 37 (6).

Kinney et al., American J. Trop. Med. Hyg., 1998, pp. 952-954, vol. 59 (6).

Kitagawa et al., "Rapid diagnosis of methicillin-resistant *Staphylococcus aureus* bacteremia by nested polymerase chain reaction," Ann. Surgery, 1996, pp. 665-671, vol. 224.

Kolbert et al., "Branched-DNA Assay for Detection of the mecA Gene in Oxacillin-Resistant and Oxacillin-Sensitive Staphylococci," J. Clin. Microbiol, 1998, pp. 2640-2644, vol. 36.

Kowalak J.A., "A Novel Method for the Determination of Post-Transcriptional Modification in RNA by Mass Spectrometry", 21 Nucleic Acids Res., 4577-4585, 1993.

Krafft, A.E. et al., "Evaluation of PCR Testing of Ethanol-Fixed Nasal Swab Specimens as an Augmented Surveillance Strategy for Influenza Virus and Adenovirus Identification," J. Clin. Microbiol, 2005, pp. 1768-1775, vol. 43 (4).

Krahmer, et al., "MS for identification of single nucleotide polymorphisms and MS/MS for discrimination of isomeric PCR products," Anal. Chem, 2000, pp. 4033-4040, vol. 72 (17).

Kramer, L. D. et al., "Dection of Encephalitis Viruses in Mosquitoes (Diptera: Culicidea) and Avian Tissues," J. Med. Entomol, 2002, pp. 312-323, vol. 39 (2).

Kramer, L. D. et al., "Dection of St. Louis Encephalitis and Western Equine Encephalomyelitis RNAin Mosquitoes Tested Without Maintainance of a Cold Chain," J. Am. Mosq. Control Assoc, 2001, pp. 213-215, vol. 17 (4).

Kresken, M. et al., "Prevalence of mupirocin resistance in clinical isolates of *Staphylococcccus aureus* and *Staphylococcus epidermidis*: results of the Antimicrobial Resistance Surveillance Study of the Paul-Ehrlich-Society for Chemotherapy, 2001," Int. J.

Krishnan, P.U. et al., "Detection of methicillin and mupirocin resistance in *Staphylococcus aureusisolates* using conventional and molecular methods: a descriptive study from a burns unit with highprevalence of MRSA," J. Clin. Pathol., 2002, pp. 745-748.

Kroes et al., "Bacterial diversity within the human subgingival crevice," Proc. Natl. Acad. Sci. USA, 1999, pp. 14547-14552, vol. 96.

Krossoy et al., "The Putative Polymerase Sequence of Infectious Salmon Anemia Virus Suggests a New Genus within the Orthomyxoviridae," Journal of Virology, 1999, pp. 2136-2142, vol. 73 (3).

Ksiaxek, Thomas G., et al., "A novel coronavirus associated with severe acute respiratory syndrome," New England Journal of Medicine, 2003, pp. 1953-1966, vol. 348 (20).

Kupke et al., "Molecular Characterization of Lantibiotic-synthesizing Enzyme EpiD Reveals a Function for Bacterial Dfp Proteins i Coenzyme A Biosynthesis," Journal of Biological Chemistry, 2000, pp. 31838-31846, vol. 275 (41).

Kuroda, M., et al., "Whole genome Sequencing of meticillin-resistant *Staphylococcus aureus*," The Lancet, 2001, pp. 1225-1240, vol. 357 (9264).

Kwok, S et al., "Avoiding false positives with PCR," Nature, 1989, pp. 237-238, vol. 339.

Labandeira-Rey, M. et al., "*Staphylococcus aureus* Panton Valentine Leukocidin CausesNecrotizing Pneumonia," Sciencexpress, 2007.

Lacroix et al., "PCR-based technique for the detection of bacteria in semen and urine," Journal of Microbiological Methods, 1996, pp. 61-71, vol. 26.

Lacroix, L. et al., "Triplex Formation by Oligonucleotides Containing 5-(1-Propynyl)-2'-deoxyuridine: Decreased Magnesium Dependence and Improved Intracellular Gene Targeting," Biochem, 1999, pp. 1893-1901, vol. 38 (6).

Lamb et al., "Sequence of Interrupted and Uninterrupted mRNAs and Cloned DNA Coding for the Two Overlapping Nonstructural Proteins of Influenza Virus," Cell, 1980, pp. 475-485, vol. 21.

Lambert, A.J. et al., "Detection of North American Eastern and Western Equine EncephalitisViruses by Nucleic Acid Amplification Assays," J. Clin. Microbiol, 2003, pp. 379-385, vol. 41 (1).

Lau, et al., "A real-time PCR for SARS-coronavirus incorporating target gene pre-amplification," Biochem. Biophys. Res. Comm, 2003, pp. 1290-1296, vol. 312.

Lau et al., "Nucleic acid sequence-based amplification methods to detect avian influenza virus," Biophys. Res. Commun, 2004, pp. 336-342, vol. 313.

Le Cann et al., "Quantification of human astroviruses in sewage using real-time RT-PCR," Res.Microbiol, 2004, pp. 11-15, vol. 155 (1).

Lebedev, Y. et al., "Oligonucleotides containing 2-aminoadenine and 5-methycytosine are more effective s primers for PCR amplification than their nonmodified counterparts," Genetic Analysis: Biomolecular Engineering, 1996, pp. 15-21, vol. 13.

Lednicky, J. A. et al., "Polyomaviruses and Human Tumors: A Brief Review of Current Concenpts and Interpretations," Front. Biosci, 1999, pp. d153-164, vol. 4.

Lee, J. A. et al., "Rapid Identification of Human Adenovirus Types 3 and 7 from Respiratory Specimens via Multiplex Type-Specific PCR," J. Clin. Microbial, 2005, pp. 5509-5514, vol. 43 (11).

Lee, J.H. et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," J. Am. Mosq. Control Assoc., 2002, pp.

Leif et al., "Isolation and characterization of the proton-translocat ng NADH: ubiqu none oxidoreductase from *Escherichia coli*," Eur. J. Biochem, 1995, pp. 538-548, vol. 230 (2).

Lengyel, A. et al., "Characterization of the Main Protein Components of Adenovirus Virion and its Possible Use in Laboratory Diagnostics," Acta Microbiol. Immunol. Hung, 1998, pp. 281-283, vol. 43 (3-4).

Leroy et al., "Diagnosis of *Ebola haemorrhagic* fever by RT-PCR in an epidemic setting," Journal of Medical Virology, 2000, pp. 463-467, vol. 60.

Levi, K. et al., "Evaluation of an Isothermal Signal Amplification Method for Rapid Detection of Methicillin-Resistant *Staphylococcus aureus* from Patient-Screening Swabs," J. Clin. MicrobioL, 2003, pp. 3187-3191, vol. 41 (7).

Levine S M et al., "PCR-based detection of *Bacillus anthracis* in formalin-fixed tissue from a patient receiving ciprofloxacin," Journal of Clinical Microbiology 20021101 US, 2002, pp. 4360-4362, vol. 40 (11).

Levison et al., "Recent developments of magnetic beads for use in nucleic acid purification," Journal of Chromatography, 1998, pp. 107-111, vol. A816.

Lewers et al., "Detection of Linked QTL for Soybean Brown Stem Rot Resistance in 'Bsr 101' asExpressed in a Growth Chamber Environment," Molecular Breeding, 1999, pp. 33-42, vol. 5.

Li, C. et al., "Evolution of H9N2 influenza viruses from domestic poultry in Mainland China," Virology, 2005, pp. 70-83, vol. 340.

Li et al., "Screening of the high yield influenza B virus on MDCK c14d cloning of its whole genome," International Congress Series 1263, 2004, pp. 610-614.

Li, et al., "Single nucleotide polymorphism determination using primer extension and time-of-flight mass spectrometry," Electrophoresis, 1999, pp. 1258-1265, vol. 20 (6).

Li, Q.-G. et al., "Analysis of 15 Different Genome Types of Adenovirus Type 7 Isolated on FiveContinents," J. Virol., 1986, pp. 331-335, vol. 60 (1).

Li, Q.-G. et al., "Comparison of 17 Genome Types of Adenovirus Type 3 Identified among Strains Recovered from Six Continents," J. Clin. Microbiol, 1988, pp. 1009-1015, vol. 26 (5).

Li, Q.-G. et al., "Genetic variability of hexon loops 1 and 2 between seven genome types of adenovirus serotype 7," Arch. Virol, 1999, pp. 1739-1749, vol. 144 (9).

Liebermann, H. et al., "Mapping of Epitopes on the Fiber Knobs of Human Adenovirus Serotypes 8 and 15," Intervirology, 2002, pp. 59-66, vol. 45.

Liebermann, H. et al., "Mapping of linear epitopes on fibre knob of human adenovirus serotype 5", Virus Res., 2001, pp. 145-151, vol. 73 (2).

Lim et al., "The microRNAs of Caenorhabditis elegans," Genes and Development, 2003, pp. 991-1008, vol. 17.

Limbach, P.A., et al., "Enzymatic Sequencing of Oligonucleotides with Electrospray Mass Spectrometry," 42nd ASMA Conference on Mass Spectrometry, 1994.

Limoncu, M. H. et al., "Emergence of phenotypic resistance to ciprofloxacin and levofloxacin in methicillin-resistant and methicillin-sensitive *Staphylococcus aureus* strains," Int. J. Antimicrob. Agents, 2003, pp. 420-424, vol. 21.

Lin, B. et al., "Use of Oligonucleotide Microarrays for Rapid Detection and Serotyping of Acute Respiratory Disease-Associated Adenoviruses," J. Clin. Microbiol, 2004, pp. 3232-3239, vol. 42 (7).

Lin et al., "Oxidative Damage to Mitochondrial Dna In Atrial Muscle Of Patients with Atrial Fibrillation. ," Free Radical Biology and Medicine, 2003, pp. 1310-1318, vol. 35 (10).

Lina, G. et al., "Bacterial Competition for Human Nasal Cavity Colonization: Role of Staphylococcalagr Alleles," Appl. Environ. Microbiol, 2003, pp. 18-23, vol. 69 (1).

Lina, G. et al., "Involvement of Panton-Valentine Leukocidin-Producing *Staphylococcus aureus* in Primary Skin Infections and Pneumonia," Clin. Infect. Dis., 1999, pp. 1128-1132, vol. 29 (5).

Ling He et al., "Development of a Capillary High-performance Liquid Chromatography Tandem Mass Spectrometry System Using SWIFT Technology in an Ion Trap/Reflectron Time-of-flight Mass Spetrometer," Rapid Comm. Mass Spectrom, 1997, pp. 1739-1748, vol. 11.

Linssen, B. et al., "Development of Reverse Transcription-PCR Assays Specific for Detection of Equine Encephalitis Viruses," J. Clin. Microbiol, 2000, pp. 1527-1535, vol. 38 (4).

Little et al. "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, pp. 4540-4546, vol. 69.

Little, et al., "Rapid sequencling of oligonucleotides by high-resolution mass spectrometry," J. Am. Chem. Soc, 1994, pp. 4893-4897, vol. 116 (11).

Liu et al., "An unusual gene arrangement for the putative chromosome replication origin and circadianexpression of dnaN in Synechococcus sp.," Strain PCC 7942 0 Gene, 1996, pp. 105-109, vol. 172 (1).

Liu, et al., "Improving the microdialysis procedure for electrospray ionization mass spectrometry of biological samples," J. Mass Spectrom, 1997, pp. 425-431, vol. 32 (4).

Liu et al., "Interregional Transmission of the Internal Protein Genes of H2 Influenza Virus in Migratory Ducks from North America to Eurasia," Virus Genes, 2004, pp. 81-86, vol. 29 (1).

Livermore, D. M. et al., "The threat from the pink corner," Ann. Med, 2003, pp. 226-234, vol. 35 (4).

Loakes, D., et al., "Nitroindoles as universal bases," Nucleosides and Nucleotides, 1995, pp. 1001-1003, vol. 14.

Loo, J. A et al., "Applying Charge Discrimination with Electrospray Ionization-Mass Spectrometry to Protein Analysis," J. Am. Soc. Mass. Spectrom, 1995, pp. 1098-1104, vol. 6.

Lott et al., "Nucleotide Sequence Analysis of the 5-8s rDNA and Adjacent ITS2 Region of Candidaalbicans and Related Species," Yeast, 1999, pp. 1199-1206, vol. 9.

Louie, L. et al., "Evaluation of Three Rapid Methods for Detection of Methicillin Resistance in *Staphylococcus aureus*," J. Clin. Microbiol, 2000, pp. 2170-2173, vol. 38 (6).

Love, B. C. et al., "Cloning and sequence of the groESL heat-shock operon of *Pasteurella multocida*," Gene, 1995, pp. 179-180, vol. 166 (1).

Lovseth, A. et al., "Modified Multiplex PCR Method for Detection of Pyrogenic Exotoxin Genes in Staphylococcal Isolates," J. Clin. MicrobioL, 2004, pp. 3869-3872, vol. 42 (8).

Lowe et al., "A computer program for selection of oligonucleotide primers for polymerase chain reactions," Nucleic Acids Research, 1990, pp. 1757-1761, vol. 18 (7).

Lu, X. et al., "Molecular typing of human adenoviruses by PCR and sequencing of a partial region of the hexon gene," Arch. Virol, 2006, pp. 1587-1602, vol. 151 (8).

Ludwig, S. L. et al., "Prevalence of Antibodies to Adenovirus Serotypes 4 and 7 among Unimmunized US Army Trainees: Results of a Retrospective Nationwide Seroprevalence Survey," Infect. Dis., 1998, pp. 1776-1778, vol. 178 (6).

Ludwig W. et al., "Bacterial phylogeny based on 16S and 23S rRNA sequence analysis," FEMS Microbiol Rev, 1994, pp. 155-73, vol. 15 (2-3).

Lukashov, V. V. et al., "Evolutionary Relationships among Parvoviruses: Virus-Host Coevolution among Autonomous Primate Parvoviruses and Links between Adeno-Associated and Avian Parvoviruses," J. Virol, 2001, pp. 2729-2740, vol. 75 (6).

Ma, X. X. et al., "Novel Type of Staphylococcal Cassette Chromosome mec Identified in Community-Acquired Methicillin-Resistant *Staphylococcus aureus* Strains," Antimicrob. Agents Chemother, 2002, pp. 1147-1152, vol. 46 (4).

Mack et al. , "A sensitive method for the identification of uncharacterized viruses related to known virus groups: Hepadnavirus model system," Proc. Natl. Acad. Sci. USA , 1988, pp. 6977-6981, vol. 85.

Magnuson et al., "Substrate Nucleotide-Determined Non-Templated Addition of Adenine by TagDNA Polymerase: Implications for PCR-Based Genotyping and Cloning," BioTechniques, 1996, pp. 700-709, vol. 21.

Maiwald, et al., "Characterization of contaminating DNA in Taq polymerase which occurs during amplification with a primer set for Legionella 5S ribosomal RNA," Molecular and Cellular Probes, 1994, pp. 11-14, vol. 8 (1).

Malasig, M.D. et al., "Simplified Microneutralization Test for Serotyping Adenovirus Isolates," J. Clin.Microbiol., 2001, pp. 2984-2986, vol. 39 (8).

Mangrum, et al., "Solution composition and thermal denaturation for the production of single-stranded PCR amplicons: piperidine-induced destabilization of the DNA duplex," J. Am. Soc. Mass Spectrom, 2002, pp. 232- 240, vol. 13 (3).

Manian, F.A et al., "Asymptomatic Nasal Carriage of Mupirocin-Resistant, Methicillin-Resistant *Staphylococcus aureus* (MRSA) in a Pet Dog Associated with MRSA Infection in Household Contacts," Clin. Infect. Dis., 2003, pp. e26-e28, vol. 36.

Marmur et al., "Strand Separation and Specific Recombination in Deoxyribonucleic Acids: Biological Studies," Proc. Natl. Acad. Sci. USA, 1960, pp. 453-461, vol. 46.

Martemyanov, K. A. et al., "Extremely Thermostable Elongation Factor (3 from Aquifer aeolicus: Cloning, Expression, Purification, and Characterization in a Heterologous Translation System," Protein Expr. Purif., 2000, pp. 257-261, vol. 18 (3).

Martineau, F. et al., "Development of a PCR Assay for Identification of *Staphylococci* at Genus andSpecies Levels," J. Clin. Microbial, 2001, pp. 2541-2547, vol. 39 (7).

Martineau, F. et al., "Species-Specific and Ubiquitous-DNA-Based Assays for Rapid Identification of *Staphylococcus aureus*," J. Clin, Microbiol, 1998, pp. 618-623, vol. 36 (3).

Martin-Lopez, J.V. et al., "Simultaneous PCR detection of ica cluster and methicillin and mupirocinresistance genes in catheter-isolated Staphylococcus," Int. Microbial., 2004, pp. 63-66, vol. 7.

Mason et al., "Diversity and linkage of replication and mobilisation genes in Bacillus rolling irclereplicating plasmids from diverse geographical origins," FEMS Microbiol. Ecol., 2002, pp. 235-241, vol. 42.

Matray et al., "Synthesis and properties of RNA analogs-oligoribonucleotide N3'->p5' phosphoramidates," Nucleic Acids Res, 1999, pp. 3976-3985, vol. 27 (20).

Matsuoka, M. et al., "Characteristic expression of three genes, msr(A), mph(C) and erm(Y), thatconfer resistance to macrolide antibiotics on *Staphylococcus aureus*," FEMS Microbiol. Lett, 2003, pp. 287-293, vol. 220.

May Alex C.W et al., "Percent sequence identity: The need to be explicit," Structure (Cambridge), 2004, pp. 737-738, vol. 12 (5).

McCabe, et al., "Bacterial species identification after DNA amplification with a universal primer pair," Mol. Genet. Metab, 1999, pp. 205-211, vol. 66 (3).

McLafferty et al., "Comparison of Algorithms and Databases for Matching Unknown Mass Spectra," J. Am. Soc. Mass Spectrom, 1998, pp. 92-95, vol. 9.

McLuckey, S.A., et al., "Ion Trap Tandem Mass Spectrometry Applied to Small Multiply Charged Oligonucleotides with a Modified Base,'787 reexamination," J. Am. Soc. Mass. Spectrom, 1994, pp. 740-747.

Mehrotra M et al., "Multiplex PCR for detection of genes for *Staphylococcus aureus* enterotoxins, exfoliative toxins, toxic shock syndrome toxin 1, and methicillin resistance ," Journal of Clinical Microbiology, Washington, DC, US, 2000, pp. 1032-1035, 38 (3).

Meiyu, et al., "Detection of flaviviruses by reverse transcriptase-polymerase chain reaction with the universal primer set," Microbiol. Immunol, 1997, pp. 209-213, vol. 41 (3).

Mellor et al., "Genotype Dependence of Hepatitis C Virus Load Measurement in Commercially Available Quantitative Assays," J. Clin. Microbiol, 1999, pp. 2525-2532, vol. 37 (8).

Merlino, J. et al., "New Chromogenic Identification and Detection of *Staphylococcus aureus* andMethicillin-Resistant *S. aureus*," J. Clin. Microbiol, 2000, pp. 2378-2380, vol. 38 (6).

Merlino, J. et al., "Rapid Detection of Non-Multidrug-Resistant and Multidrug-Resistant Methicillin-Resistant *Staphylococcus aureus* Using Cycling Probe Technology for the mecA Gene," Elm J. Clin. MicrobioL Infect. Dis, 2003, pp. 322-323, vol. 22.

Messmer, et al., "Discrimination of *Streptococcus pneumoniae* from other upp.er respiratory tract Streptococci by arbitrary primed PCR," Clin. Biochem, 1995, pp. 567-572, vol. 28 (6).

Metzgar, D. et al., "PCR Analysis of Egyptian Respiratory Adenovirus Isolates, Including Identification of Species, Serotypes and Coinfections," J. Clin. Microbiol, 2005, pp. 5743-5752, vol. 43 (11).

Miller et al., "A compendium of human mitochondria! DNA control region: development of an international standard forensic database," Croat Med. J., 2001, pp. 315-327, vol. 42.

Miragaia, M. et al., "Genetic Diversity among Methicillin-Resistant *Staphylococcus epidemidis*(MRSE," Microbial Drug Resistance, 2005, pp. 83-93, vol. 11 (2).

Miura-Ochiai, R. et al., "Quantitative detection and rapid identification of human adenoviruses," J Clin. Microbiol, 2007, pp. 958-967, vol. 45 (3).

Mollet et al., "rpoB sequence analysis as a novel basis for bacterial identification," Molecular Microbiology, 1997, pp. 1005-1011, vol. 26 (5).

Monroy, A.M. et al., "Exvaluation of Reverse Transcriptase Polymerase Chain Reaction for theDetection of Eastern Equine Encephalumyelitis Virus during Vector Surveillance," J. Med. Entomol, 1996, pp. 449-457, vol. 33 (3).

Moore, C. et al., "Development and Evaluation of a Real-Time Nucleic Acid Sequence Based Amplification Assay for Rapid Detection of Influenza A," J. Med. Virol., 2004, pp. 619-628, vol. 74 (4).

Moricca S. et al., "Detection of *Fusarium oxysporum* f.sp. vasinfectum in cotton tissue by polymerase chain reaction," Plant Pathology, 1998, pp. 486-494, vol. 47 (4).

Morinaga, N. et al., "Purification, Cloning and Charactarizarion of Variant LukE-LukD with Strong Leukocidal Activity of Staphylococcal Bi-Component Leukotoxin Family," Microbiol. Immunol, 2003, pp. 81-90, vol. 47 (1).

Morse et al., "Nucleotide Sequence of Part of the ropC Gene Encoding the B Subunit of DNADependentRNA Polymerase from some Gram-Positive Bacteria and Comparative Amino AcidSequence Analysis," System Appl. Microbiol, 1996, pp. 150-157, vol. 19.

Muddiman, D.C., et al., "Precise mass measurement of a double-stranded 500 base-pair (309 kDa) polymerase chain reaction product by negative ion electrospray ionization fourier transform ion cyclotron resonance mass spectrometry," Rapid Commun. Mass Spec, 1999, pp. 1201-1204, vol. 13 (2).

Muddiman, et al., "App.lication of secondary ion and matrix-assisted laser desorption-ionization time-of-flight mass spectrometry for the quantitative analysis of biological molecules," Mass Spectrom. Rev, 1996, pp. 383-429, vol. 14 (6).

Muddiman, et al., "Important aspects concerning the quantification of biomolecules by time-of-flight secondaryion mass spectrometry," App.l. Spectrometry, 1996, pp. 161-166, vol. 50 (2).

Muddiman et al., "Sequencing and characterization of larger oligonucleotides by electrospray ionization fourier transform ion cyclotron resonance mass spectrometry," Rev. Anal. Chem, 1998, pp. 1-68, vol. 17 (1).

Muhammed, et al., "Electrospray ionization quadrupole time-of-flight mass spectrometry and quadrupole mass spectrometry for genotyping single nucleotide substitutions in intact polymerase chain reaction products in K-ras and p53," Rapid Commun. Mass Spectrom., 2002, pp. 2278-2285, vol. 16 (24).

Murakami, K. et al., "Identification of Methicillin-Resistant Strains of Staphylococci by PolymeraseChain Reaction," J. Clin. Microbiol, 1991, pp. 2240-2244, vol. 29 (10).

Mushegian, A.R., et al., "A minimal gene set for cellular life derived by comparison of complete bacterial genomes," Proc. Natl. Acad. Sci. USA, 1996, pp. 10268-10273, vol. 93 (19).

Na, B.-K. et al., "Detection and Typing of Respiratory Adenoviruses in a Single-Tube Multiplex Polymerase Chain Reaction," J. Med. Viral, 2002, pp. 512-517, vol. 66 (4).

Nagpal, et al., "Utility of 16S-23S rRNA spacer region methodology: how similar are interspace regions within a genome and between strains for closely related organisms?," J. Microbiol. Methods, 1998, pp. 211-219, vol. 33.

Nagy, M. et al., "Sequence Analysis of Porcine Adenovirus Serotype 5 Fibre Gene: Evidence for Recombination," Virus Genes, 2002, pp. 181-185, vol. 24 (2).

Nakagawa, S. et al., "Gene sequences and specific detection for Panton-Valentine leukocidin," Biochem. Biophys. Res. Commun, 2005, pp. 995-1002, vol. 328.

Nakao, H. et al., "Development of a Direct PCR Assay for Detection of the Diphtheria Toxin Gene," J. Clin. Microbiol., 1997, pp. 1651-1655, vol. 35 (7).

Narita, S. et al., "Phage conversion of Panton-Valentine leukocidin in *Staphylococcus aureus*: molecular analysis of a PVL-converting phage, phiSLT," Gene, 2001, pp. 195-206, vol. 268 (1-2).

Naumov, G.I. et al., "Discrimination between the soil yeast species *Williopsis saturnus* and *Williopsis suaveolens* by the polymerase chain reaction with the universal primer N21," Microbiology (Moscow)(Translation of Mikrobiologiya), 2000, pp. 229-233, vol. 69.

Neumann, G. et al., "Host Range Restriction and Pathogenicity in the Context of Influenza Pandemic," Emerg. Infect. Dis, 2006, pp. 881-886, vol. 12 (6).

New England Biolabs (NEB) Catalog (1998-1999) pp. 1, 79, 121, 284.

Newcombe et al., "PCR of Peripheral Blood for Diagnosis of Meningococcal Disease," Journal of Clinical Microbiology, 1996, pp. 1637-1640, vol. 34 (7).

NG, et al., "Quantitative analysis an prognostic implication of SARS coronavirus RNA in the plasma and serum of patients with severe acute respiratory syndrome," Clin. Chem., 2003, pp. 1976-1980, vol. 49.

NG, et al., "Serial analysis of the plasma concentration of SARS coronavirus RNA in pediatric patients with severe acute respiratory syndrome," Clin. Chem., 2003, pp. 2085-2088, vol. 49.

Ni et al., "Interpretation of Oligonucleotide Mass Spectra for Determinationof Sequence Using Electrospray Ionization and Tandem Mass Spectrometry," Anal. Chem., 1996, pp. 1989-1999, vol. 68.

Nilsson et al., "Evaluation of mitochondrial DNA coding region assays for ncreased discrimination in forensic analysis," Forensic Science International: Genetics, 2008, pp. 1-8, vol. 2.

Nishikawa, T. et al., "Reconstitution of active recombinant Ship toxin (Stc)1 from recombinant Stx1 -A and Sbt1 -B subunits independently produced by *E. coli* clones," FEMS Microbiol Lett., 1999, pp. 13-18, vol. 178.

Non-final office action for the U.S. Appl. No. 12/616,422, mailed Sep. 14, 2010.

Non-Final Office Action mailed Feb. 23, 2009, for U.S. Appl. No. 10/660,122 filed Sep. 11, 2003.

Non-Final Office Action mailed Mar. 31, 2010, for U.S. Appl. No. 12/049,949 filed Mar. 17, 2008.

Non-Final Office Action mailed Apr. 6, 2009, for U.S. Appl. No. 11/331,987 filed Jan. 13, 2006.

Non-Final Office Action mailed Apr. 7, 2009, for U.S. Appl. No. 12/211,641 filed Sep. 16, 2008.

Non-Final Office Action mailed Apr. 30, 2010, for U.S. Appl. No. 11/930,108 filed Oct. 31, 2007.

Non-Final Office Action mailed Apr. 7, 2006, for U.S. Appl. No. 10/964,571 filed Oct. 12, 2004.

Non-Final Office Action mailed May 26, 2005, for U.S. Appl. No. 10/156,608 filed May 24, 2002.

Non-Final Office Action mailed May 26, 2006, for U.S. Appl. No. 10/660,997 filed Sep. 12, 2003.

Non-Final Office Action mailed May 26, 2010, for U.S. Appl. No. 11/869,449 filed Oct. 9, 2007.

Non-Final Office Action mailed Jul. 13, 2010, for U.S. Appl. No. 11/929,930 filed Oct. 30, 2007.

Non-Final Office Action mailed Jul. 27, 2006, for U.S. Appl. No. 11/209,439 filed Aug. 23, 2005.

Non-Final Office Action mailed Sep. 5, 2006, for U.S. Appl. No. 10/660,996 filed Sep. 12, 2003.

Non-Final Office Action mailed Sep. 16, 2009, for U.S. Appl. No. 11/233,630 filed Sep. 21, 2005.

Non-Final Office Action mailed Sep. 28, 2009, for U.S. Appl. No. 11/930,017 filed Oct. 30, 2007.

Non-Final Office Action mailed Oct. 2, 2009, for U.S. Appl. No. 11/929,707 filed Oct. 30, 2007.

Non-Final Office Action mailed Nov. 15, 2007, for U.S. Appl. No. 11/331,978 filed Jan. 13, 2006.

Non-Final Office Action mailed Nov. 19, 2003, for U.S. Appl. No. 09/798,007 filed Mar. 2, 2001.

Non-Final Office Action mailed Jun. 28, 2010, for U.S. Appl. No. 11/930,002 filed Oct. 30, 2007.

Norder et al., "Typing of Hepatitis B Virus Genomes by a Simplified Polymerase Chain Reaction," J.Med. Virol, 1990, pp. 215-221, vol. 31.

Nordhoff, E., et al., "Matrix Assisted Laser Desorption/Ionization Mass Spectrometry of Nucleic Acids with Wavelengths in the Ultraviolet and Infrared,'787 reexamination," Rapid Commun. Mass Spectrom, 1992, pp. 771-776.

Notice of intent to issue a reexamination certificate.

Nubel et al., "PCR primers to amplify 16S rRNA genes from Cyanobacteria," Applied andEnvironmental Microbiology, 1997, pp. 3327-3332, vol. 63 (8).

Null Allison P. et al., "Enzymatic strategies for the characterization of nucleic acids by electrospray ionization mass spectrometry." Rapid Communications in Mass Spectrometry, 2003, pp. 2699-2706, vol. 17 (24).

Null and Muddiman, "Determination of a correction to improve mass measurement accuracy of isotopically unresolved polymerase chain reaction amplicons by electrospray ionization Fourier transform ion cyclotron resonance mass spectrometry," Rapid Comm. Mass.

Null and Muddiman, "Perspectives on the use of electrospray ionization Fourier transform ion cyclotron resonance mass spectrometry for short tandem repeat genotyping in the post genome era," J. Mass Spectrom, 2001, pp. 589-606, vol. 36 (6).

Null, et al., "Genotyping of simple and compound short tandem repeat loci using electrospray ionization Fourier transform ion cyclotron resonance mass spectrometry," Anal. Chem, 2001, pp. 4514-4521, vol. 73 (18).

Null, et al., "Implications of hydrophobicity and free energy of solvation for characterization of nucleic acids by electrospray ionization mass spectrometry," Anal. Chem., 2003, pp. 1331-1339, vol. 75.

Null, et al., "Preparation of single-stranded PCR products for electrospray Ionization mass spectrometry using the DNA repair enzyme lambda exonuclease," Analyst, 2000, pp. 619-626, vol. 125.

Nunes, E. L. et al., "Detection of ileS-2 Gene Encoding Mupirocin Resistance in Methicillin-ResistantStaphylococcus aureus by Multiplex PCR," Diagn. Microbiol. Infect. Dis., 1999, pp. 77-81, vol. 34 (2).

Nygren et al., "Quantification of HIV-1 Using Multiple Quantitative Polymerase Chain ReactionStandards and Bioluminometric Detection," Anal. Biochem, 2001, pp. 28-38, vol. 288 (1).

Oberacher H et al., "Increased foresnic efficiency of DNA fingerprints through simultaneous resolution of length and nucleotide variability by high-performance mass spectrometry," Human Mutation, 2008, pp. 427-432, vol. 29 (3).

Oberste, et al., "Improved molecular identification of enteroviruses by RT-PCR and amplicon sequencing," J. Clin. Virol, 2003, pp. 375-377, vol. 26.

Oberste, et al., "Molecular epidemiology and type-specific detection of echovirus 11 isolates fromthe Americas, Europe, Africa, Australia, southern Asia and the Middle East," Virus Res, 2003, pp. 241-248, vol. 91.

Oberste, et al., "Molecular phylogeny and proposed classification of the Simian picornaviruses," J. Virol., 2002, pp. 1244-1251, vol. 76.

O'Guinn, M.L. et al., "Field Detection of Eastern Equine Encephalitis Virus in the Amazon BasinRegion of Peru Using Reverse Transcription-Polymerase Chain Reaction Adapted for FieldIdentification of Arthropod-Borne Pathogens," Am. J. Trop. Med. Hyg, 2004.

Oizumi, N, et al., "Relationship between mutations in the DNA gyrase and topoisomerase IV genes and nadifloxacin resistance in clinically isolated quinolone-resistant *Staphylococcus aureus*," Journal of Infection and Chemotherapy: Official Journal of the Japan Society of Chemotherapy, 2001, 7 (3), 191-194.

Okada, M. et al., "Detection and sequence-based typing of human adenoviruses using sensitiveuniversal primer sets for the hexon gene," Arch. Virol, 2007, pp. 1-9, vol. 152 (1).

Okuma, K. et al., "Dissemination of New Methicillin-Resistant *Staphylococcus aureus* Clones in the Community," J. Clin. Mcrobiol, 2002, pp. 4289-4294, vol. 40 (11).

Oliveira, D. C. et al., "Genetic Organization of the Downstream Region of the mecA Element in Methicillin-Resistant *Staphylococcus aureus* Isolates Carrying Different Polymorphisms of ThisRegion," Antimicrob. dients Chemother, 2000, pp. 1906-1910, vol. 44.

Oliveira, D. C. et al., "Multiplex PCR Strategy for Rapid Identification of Structural Types and Variants of the mec Element in Methicillin-Resistant *Staphylococcus aureus*," Antimicrob. Agents Chemother, 2002, pp. 2155-2161, vol. 46 (7).

Olsen et al., "Transhemispheric exchange of Lyme disease spyrochetes by seabirds", Journal of Clinical Microbiology, 1995, pp. 3270-3274, vol. 33.

Osiowy, C et al., "Direct Detection of Respiratory Syncytial Virus, Parainfluenza Virus, and Adenovirus in Clinical Respiratory Specimens by a Multiplex Reverse Transcription- PCR Assay," J. Clin. Microbial, 1998, pp. 3149-3154, vol. 36 (11).

Ostrander, E. A. et al., "Identification and Characterization of Dinucleotide Repeat (CA)n. Markers for Genetic Mapping in Dog," Genomics, 1993, pp. 207-213, vol. 16 (1).

Ounissi, H. et al., "Gene Homogeneity for Aminoglycoside-Modifying Enzymes in Gram-PositiveCocci," Antimicrob. Agents Chemother, 1990, pp. 2164-2168, vol. 34 (11).

Pan, Z.-Q et al., "Oligonucleotide-targeted degradation of U1 and U2 snRNAs reveals differential interactions of simian virus 40 pre-mRNAs with snRNPs," Nucleic Acids Res, 1989, pp. 6553-6568, vol. 17 (16).

Pannetier et al., "Quantitative titration of nucleic acids by enzymatic amplification reactions run to saturation", Nucleic Acids Research, 1993, pp. 577-583, vol. 21 (3).

Parson et al., "Population data for 101 Austrian Caucasian mitochondrial DNA d-loop sequences: Application of mtDNA sequence analysis to a forensic case," Mt. J. Legal Med, 1998, pp. 124-132, vol. 111.

Pastorino, B. et al., "Development of a TaqMan PCR assay without RNA extraction step for the detection and quantification of African Chikungunya viruses," J. Virol. Methods, 2005, pp. 65-71, vol. 124 (1-2).

Paterson et al., "Fine Mapping of Quantitative Trait Loci Using Selected Overlapping RecombinantChromosomes, in an Interspecies Cross of Tomato," Genetics, 1990, pp. 735-742, vol. 124.

Pawa, A. et al., "Co-transfer of plasmids in association with conjugative transfer of mupirocin or mupirocin and penicillin resistance in methicillin-resistant *Staphylococcus aureus*," J. Med. Microbiol, 2000, pp. 1103-1107, vol. 49.

PCT International Preliminary Examination Report dated Feb. 2, 2007, in International Application No. PCT/US2003/38757, filed Dec. 5, 2003.

PCT International Preliminary Examination Report dated Jun. 11, 2003, in International Application No. PCT/US2002/06763, filed Mar. 4, 2002.

PCT International Preliminary Examination Report dated Jun. 27, 2006, in International Application No. PCT/US2003/38761, filed Dec. 5, 2003.

PCT International Preliminary Examination Report dated Mar. 3, 2006, in International Application No. PCT/US2003/38505, filed Dec. 5, 2003.

PCT International Preliminary Examination Report with Written Opinion of the International Searching Authority mailed on May 9, 2006, in International Application No. PCT/US2005/00386, filed Jan. 7, 2005.

PCT International Search Report and the Written Opinion of the International Searching Authority, or the Declaration, mailed on Jan. 8, 2009 for PCT Application No. PCT/US2007/20045, filed Sep. 14, 2007, 18 pages.

PCT International Search Report and the Written Opinion of the International Searching Authority, or the Declaration, mailed on May 15, 2006 for PCT Application No. PCT/US2004/33742, filed Dec. 9, 2004, 5 pages.

PCT International Search Report and the Written Opinion of the International Searching Authority, or the Declaration, mailed on Oct. 10, 2010 for PCT Application No. PCT/US2009/045635, filed Mar. 29, 2009, 23 pages.

PCT International Search Report for PCT/US06/007747 dated Sep. 5, 2006.

PCT International Search Report for PCT/US2006/061307 dated Jan. 9, 2008.

PCT International Search Report for PCT/US2007/020045 dated Jan. 8, 2009.

PCT International Search Report for PCT/US2007/066194 dated Jan. 15, 2008.

PCT International Search Report for PCT/US2008/054926 dated Jan. 26, 2009.

PCT International Search Report for PCT/US2009/045635 dated Oct. 7, 2009.

PCT Notification of Transmittal of the International Search Report and the Written Opinion of the International Searching Authority, or the Declaration, mailed on May 3, 2007 for PCT Application No. PCT/US06/028397, filed Jul. 21, 2006, 14 pages.

PCT Notification of Transmittal of the International Search Report and the Written Opinion of the International Searching Authority, or the Declaration, mailed on Sep. 1, 2008, for PCT Application No. PCT/US2006/061307, filed Nov. 28, 2006, 21 pages.

PCT Notification of Transmittal of the International Search Report and the Written Opinion of the International Searching Authority, or the Declaration, mailed on Aug. 28, 2008, for PCT Application No. PCT/US08/057901, 14 pages.

PCT Notification of Transmittal of the International Search Report and the Written Opinion of the International Searching Authority, or the Declaration, mailed on Jan. 15, 2008, for PCT Application No. PCT/US2007/066194, filed Apr. 6, 2007, 13 pages.

PCT Notification of Transmittal of the International Search Report and the Written Opinion of the International Searching Authority, or the Declaration, mailed on Jan. 26, 2009 for PCT Application No. PCT/US2008/054926, filed Feb 25, 2008, 20 pages.

PCT Notification of Transmittal of the International Search Report and the Written Opinion of the International Searching Authority, or the Declaration, mailed on Oct. 10, 2006, for PCT Application No. PCT/US06/015160, 13 pages.

PCT Notification of Transmittal of the International Search Report and the Written Opinion of the International Searching Authority, or the Declaration, mailed on Sep. 3, 2009 for PCT Application No. PCT/US2008/054926, filed Feb. 25, 2008, 9 pages.

PCT Notification of Transmittal of the International Search Report and the Written Opinion of the International Searching Authority, or the Declaration, mailed on Sep. 5, 2006, for PCT Application No. PCT/US06/007747, Mar. 3, 2006, 13 pages.

PCT Notification of Transmittal of the International Search Report, or the Declaration, mailing date Apr. 12, 2005, for PCT Application No. PCT/US2003/38505, filed Dec. 5, 2003, 4 pages.

PCT Notification of Transmittal of the International Search Report, or the Declaration, mailing date Apr. 19, 2004, for PCT/US2003/38795, filed Dec. 5, 2003, 11 pages.

PCT Notification of Transmittal of the International Search Report, or the Declaration, mailing date Aug. 8, 2004, for PCT/US2003/38830, filed Dec. 5, 2003, 6 pages.

PCT Notification of Transmittal of the International Search Report, or the Declaration, mailing date Jun. 24, 2004, for PCT Application No. PCT/US2003/38757, filed Dec. 5, 2003, 6 pages.

Peng, et al., "Rapid detection of Shigella species in environmental sewage by an immunocapture PCR with universal primers," App.. Environ. Microbiol, 2002, pp. 2580-2583, vol. 68 (5).

Perez-Roth, E. et al., "Multiplex PCR for Simultaneous Identification of *Staphylococcus aureus* andDetection of Methicillin and Mupirocin Resistance," J. Clin. Microbial, 2001, pp. 4037-4041, vol. 39 (11).

Peters et al., "Quantification of the detection of *Pneumocystis carinii* by DNA amplification," Mol. Cell. Probes, 1992, pp. 115-117, vol. 6.

Pfeffer, M. et al., "Genus-Specific Detection of Alphaviruses by a Semi-Nested ReverseTranscription-Polymerase Chain Reaction," Am. J. Trop. Med Hyg., 1997, pp. 709-718, vol. 57 (6).

Pfeffer, M. et al., "Specific Detection of Chikungunya Virus Using a RT-PCR/Nested PCR Combination," J. Vet. Med. B, 2002, pp. 49-54, vol. 49 (1).

Pieles, U, et al., "Matrix-Assisted Laser Desorption Ionization Time-of-Flight Spectrometry: APowerful Tool for the Mass and Sequence Analysis of Natural and Modified Oligonucleotides, '787 reexamination," Nucleic Acids Res, 1993, pp. 3191-3196, vol. 21 (14).

Pillai, S.D et al., "Rapid molecular detection of microbial pathogens: breakthroughs and challenges," Arch Virol, 1997, pp. 67-82, vol. 13.

Piper, J. et al., "Commercially Available Technique for Rapid Laboratory Detection of MethicillinResistance Among *Staphylococcus aureus*," Diagn. Microbial. Infect. Dis., 1988, pp. 177-180, vol. 11 (3).

Poddar, S. K. et al, "Detection of adenovirus using PCR and molecular beacon," J. Viral. Methods., pp. 19-26, vol. 82 (1).

Pomerantz. et al., "Determination of oligonucleotide composition from mass spectrometrically measured molecular weight," J. Am. Soc. Mass Spectrom, 1993, pp. 204-209, vol. 4 (3).

Pring-Akerblom, P. et al., "Multiplex Polymerase Chain Reaction for Subgenus-Specific Detection of Human Adenoviruses in Clinical Samples," J Med. Viral., 1999, pp. 87-92, vol. 58 (1).

Pring-Akerblom, P. et al., "PCR-based detection and typing of human adenoviruses in clinical samples," Res. Vim, 1997, pp. 225-231, vol. 148 (3).

Promega. T4 Polynucleotide Kinase, Promega Technical Bulletin No. 519, 2002.

Puthavathana, P. et al., "Molecular characterization of the complete genome of human influenza H5N1 virus Isolates from Thailand," J. Gen. Virol., 2005, pp. 423-433, vol. 86.

Qadri, S. M. et al., "Rapid Detection of Methicillin-Resistant *Staphylococcus aureus* by CrystalMRSA ID System," J. Clin. Microbiol., 1994, pp. 1830-1832, vol. 32 (7).

Raaum R L et al., "Catarrhine primate divergence dates estimated from complete mitochondria' genomes: concordance with fossil and nuclear DNA evidence," Journal of Human Evolution, Academic Press, London, GB 2005, pp. 237-257, vol. 48 (3).

Ram Isse V. et al., "Identification and characterization of Bacillus anthracis by multiplex PCR analysis of sequences on plasmids pX01 and pX02 and chromosomal DNA," FEMS Microbiology Letters, 1996, pp. 9-16, vol. 145 (1).

Reid, S.M. et al., "Primary diagnosis of foot-and-mouth disease by reverse transcription polymerase chain reaction," Journal of Virological Method, 2000, pp. 167-176, vol. 89 (1-2).

Reilly, et al., "Design and use of 16s ribosomal DNA-directed primers in competitive PCRs to enumerate proteolytic bacteria in the rumen," Microb. Ecol, 2002, pp. 259-270, vol. 43 (2).

Reischl et al., "Application of Molecular Biology-Based Methods to theDiagnosis of Infectious Diseases", Frontiers Biosci., 1996, pp. e72-e77, vol. 1.

Reischl, U. et al., "Rapid Identification of Methicillin-Resistant *Staphylococcus aureus* and Simultaneous Species Confirmation Using Real-Time Fluorescence PCR," J. Clin. MicrobioL, 2000, pp. 2429-2433, vol. 38 (6).

Roberts, M.M. et al., "Three-Dimensional Structure of the Adenovirus Major Coat Protein Hexon ," Science, 1986, pp. 1148-1151, vol. 232 (4754).

Robinson, D. A. et al., "Multilocus sequence typing and the evolution of methicillin-resistant*Staphylococcus aureus*," Clin. Microbiol. Infect., 2004, pp. 92-97, vol. 10.

Ross, et al., "Analysis of DNA fragments from conventional and microfabricated PCR devices using delayed extraction MALDI-TOF mass spectrometry," Anal. Chem., 1998, pp. 2067-2073, vol. 70 (10).

Ross et al., "Discrimination of Single-Nucleotide Polymorphisms in Human DNA Using Peptide Nucleic Acid Probes Detected by MALDI-TOF Mass Spectrometry," Anal. Chem, 1997, pp. 4197-4202, vol. 69 (20).

Rota et al., "Sequencing of a cDNA clone of the nucleoprotein gene of influenza B/Ann Arbor/1/86," Nucleic Acids Research, 1989, pp. 3595, vol. 17 (9).

Ruan et al., "Comparative full-length genome sequence analysis of 14 SARS coronavirus isolates and common mutations associated with the putative origins of infection," lancet, 2003, pp. 1832, vol. 361.

Ruest et al., "Comparison of the Directigen Flu A+B test, the QuickVue Influenza Test, and Clinical Case Definition to Viral Culture and Reverse Transcription-PCR for Rapid Diagnosis of Influenza Virus Infection," J. Clin. Microbiol., 2003, pp. 3487-349.

Rupf et al., "Quantitative determination of Streptococcus mutans by using competitive polymerasechain reaction," Eur. J. Oral. Sci., 1999, pp. 75-81, vol. 107 (2).

Russell, K. L. et al., "Transmission Dynamics and Prospective Environmental Sampling of Adenovirus in a Military Recruit Setting," J. Infect. Dis., 2006, pp. 877-885, vol. 194 (7).

Sabat, A. et al., "Comparison of PCR-Based Methods for Typing *Staphylococcus aureus* Isolates" J. Clin. Microbiol, 2006, pp. 3804-3807, vol. 44 (10).

Sackesen, C. et al., "Use of polymerase chain reaction for detection of adenovirus in children withor without wheezing," Turk. J. Pediatr., 2005, pp. 227-231, vol. 47 (3).

Sakai, H. et al., "Simultaneous Detection of *Staphylococcus aureus* and Coagulase- Staphylococci in Positive Blood Cultures by Real-Time PCR with Two Fluorescence Resonance Energy Transfer Probe Sets," J Clin. MicrobioL, 2004, pp. 5739-5744, vol.

Sala, M. et al., "Ambiguous base pairing of the purine analogue 1-(2-deoxy-B-D -ribofuranosyl)-imidazole-4-carboxamide during PCR," Nucl. Acids Res, 1996, pp. 3302- 3306, vol. 24 (17).

Sambrook J., et al., "Molecular Cloning-A Laboratory Manual," 1989, 2, Cold Spring Harbor Laboratory Press, Table of Contents.

Sampath, Rangarajan et al., "Global surveillance of emerging influenza virus genotypes by mass spectrometry", Plos One, 2007 p. e489, vol. 5.

Sampath, Rangarajan et al., "Rapid identification of emerging infectious agents using PCR and electrospray ionization mass spectrometry," Ann. N.Y. Acad. Of Sci, 2007, pp. 109-120, vol. 1102.

Sampath Rangarajan et al., "Rapid identification of emerging pathogens: coronavirus," Emerging Infectious Diseases, 2005, pp. 373-379, vol. 11 (3).

Sanchez et al., "Detection and molecularcharacterization of Ebola viruses causing disease in human and nonhuman primates," The Journal of Infectious Diseases, 1999, pp. S164-S169, vol. 179 (1).

Sanchez, J. L. et al., "Epidemic of Adenovirus-Induced Respiratory Illness Among US Military Recruits: Epidemiologic and Immunologic Risk Factors in Healthy, Young adults," J. Med. Virol, 2001, pp. 710-718, vol. 65 (4).

Sanchez-Seco, M. P. et al., "A generic nested-RT-PCR followed by sequencing for detection andidentification of members of the alphavirus genus," J. Virol. Methods, 2001, pp. 153-161, vol. 95 (1-2).

Santos et al., "Identification and phylogenetic sorting of bacterial lineages with universally conserved genes and proteins," Environmental Microbiology, 2004, pp. 754-759, vol. 6 (7).

Sarantis, H. et al., "Comprehensive Detection and Serotyping of Human Adenoviruses by PCR and Sequencing," J. Clin. Microbial., 2004, pp. 3963-3969, vol. 42 (9).

Sauer, S. et al., "A novel procedure for efficient genotyping of single nucleotide polymorphisms," Nucleic Acids Res, 2000, pp. E13.1-E13.8, vol. 28 (5).

Scaramozzino, et al., "Comparison of Flavivirus universal primer pairs and development of a rapid, highly sensitive heminested reverse transcription-PCR assay for detection of flaviviruses targeted to a conserved region of the NS5 gene sequences," J. Clin. Microbiol., 2001,pp. 1922-1927, vol. 39 (5).

Schabereiter-Gurtner et al., "Application of broad-range 16s rRNA PCR amplification and DGGE fingerprinting for detection of tick-infecting bacteria", The Journal of Microbiological Methods, 2003, pp. 251-260, vol. 52.

Scheffner, M. et al., "The E6 Oncoprotein Encoded by Human Papillomavirus Types 16 and 18 Promotes the Degradation of p53," Cell, 1990, pp. 1129-1136, vol. 63.

Schena M et al., "Genome analysis with gene expression microarrays," Bioessays, 1996, pp. 427-431, vol. 18.

Scheuermann et al., "Polymerase chain-reaction-based mRNA quantification Using an internal standard: analysis of oncogene expression", Methods in Enzymology, 1993, pp. 446-473, vol. 218.

Schlecht, N. F. et al., "Viral Load as a Predictor of the Risk of Cervical Intraepithelial Neoplasia," Mt. J. Cancer, 2003, pp. 519-524, vol. 103.

Schmidt et al., "Analysis of a marine pikoplankton community by 16s rRNA gene cloning and sequencing," J. Bacteriol., 1991, pp. 4371-4378, vol. 173.

Schmitz, F. J. et al., "Development of a multiplex-PCR for direct detection of the genes for enterotoxin B and C, and toxic shock syndrome toxin-1 in *Staphylococcus aureus* isolates," J. Med. Microbiol., 1998, pp. 335-340, vol. 47 (4).

Schmitz, F. J. et al., "Development of Resistance to Ciprofloxacin, Rifampin, and Mupirocin inMethicillin-Susceptible and -Resistant *Staphylococcus aureus* Isolates," Antimicrob. AgentsChemother, 2000, pp. 3229-3231, vol. 44 (11).

Schmitz, F. J. et al., "Specific information concerning taxonomy, pathogenicity and methicillin esistance of staphylococci obtained by a multiplex PCR," J. Med. MicrobioL, 1997, pp. 773-778, vol. 46.

Schram et al., "Mass Spectrometry of Nucleic Acid Components," in Biomedical Applications of Mass Spectrometyr, 1990, pp. 203-280, vol. 34.

Schultz, et al., "Polymerise chain reaction products analyzed by charge detection mass spectrometry," Rapid Comm. Mass Spectrom, 1999, pp. 15-20, vol. 13 (1).

Schwartz, M, et al., Prenatal diagnosis of alpha-1-antitrypsin deficiency using polymerase chainreaction (PCR). Comparison of conventional RFLP methods with PCR used in combination with allelespecific oligonucleotides or RFLP analysis, '787 reexamination.

Schweiger, B. et al., "Application of a Fluorogenic PCR Assay for Typing and Subtyping of Influenza Viruses in Respiratory Samples," J. Clin. Microbiol., 2000, pp. 1552-1558, vol. 38 (4).

Scott-Taylor, T. H. et al., "Conserved Sequences of the Adenovirus Genome for Detection of all Human Adenovirus Types by Hybridization," J. Clin. Microbiol., 1992, pp. 1703-1710, vol. 30 (7).

Seifarth, et al., "Rapid identification of all known retroviral reverse transcriptase sequences with a novel versatile detection assay," AIDS Res. Human Retrovir., 2000, pp. 721-729, vol. 16.

Sellner, L et al., "A Single-Tube Nested RT-PCR for the Detection of Ross River Virus," Methods Mol. Biol., 1998, pp. 145-152, vol. 92.

Sellner, L. N. et al., "Sensitive detection of Ross River virus—a one-tube nested RT-PCR," J. Virol.Methods, 1994, pp. 47-58, vol. 49 (1).

Senko et al., "Determination of Monoisotopic Masses and Ion Populations for Large Biomoleculesfrom Resolved Isotopic Distributions," J. Am. Soc. Mass Spectrom., 1995, pp. 229, vol. 6.

Seshadri et al., "Differential Expression of Translational Elements by Life Cycle Variants of *Coxiella burnetii*," Infect. Immun, 1999, pp. 6026-6033, vol. 67 (11).

Shadan, F. F. et al., "n-Butyrate, a Cell Cycle Blocker, Inhibits the Replication of Polyomaviruses and Papillomaviruses but Not That of Adenoviruses and Herpesviruses," J. Virol., 1994, pp. 4785-4796, vol. 68 (8).

Shaver, et al., "Restriction fragment length polymorphism of rRNA operons for discrimination and intergenic spacer sequences for cataloging of Bacilus subtilis sub-groups," J. Microbiol. Methods, 2002, pp. 215-223, vol. 50 (2).

Shaver, et al., "Variation in 16s-23s rRNA intergenic spacer regions among *Bacilus subtilis* 168 isolates" Mol. Microbiol, 2001, pp. 101-109, vol. 42 (1).

Shi Rong, et al., "Design and application of 60mer oligonucleotide microarray in SARS coronavirus detection," Chinese Sci. Bull., 2003, pp. 1165-1169, vol. 48.

Shimaoka, M. et al., "Detection of the gene for toxic shock syndrome toxin 1 in *Siaphylococcusaureus* by enzyme-labelled oligonucleotideprobes ," J. Med. Microbiol., 1996, pp. 215-218, vol. 44.

Shimaoka, M. et al., "Development of Enzyme-Labeled Oligonucleotide Probe for Detection of mecA gene in Methicillin-Resistant *Staphylococcus aureus*," J. Clin. MicrobioL, 1994, pp. 1866-1869, vol. 32 (8).

Shrestha, N. K. et al., "Rapid Identification of *Staphylococcus aureus* and the mecA Gene fromBacT/ALERT Blood Culture Bottles by Using the Lightcycler System ," J. Clin. Microbiol., 2002, pp. 2659-2661, vol. 40 (7).

Simonsen et al., "The Impact of Influenza Epidemics on Hospitalizations," J. Infect. Dis., 2000, pp. 831-837, vol. 181.

Skov, R L. et al., "Evaluation of a new 3-h hybridization method for detecting the mecA gene in *Staphylococcus aureus* and comparison with existing genotypic and phenotypic susceptibility testing methods ," J. Antimicrob. Chemother., 1999, pp. 467-475, Vo.

Smith, et al.,"Comparison of Biosequences", Adv. Appl. Math, 1981, 2, 482-489.

Song, et al., "Identification of cry11-type genes from *Bacilus thuringiensis* strains and characterization of a novel cry11-type gene," App.. Environ. Microbiol., 2003, pp. 5207-5211, vol. 69.

Spackman et al., "Development of a real-time reverse transcriptase PCR assay for type A influenzavirus and the avian H5 and H7 hemagglutinin subtypes," Journal of Clinical Microbiology, 2002, pp. 3256-3260, vol. 40.

Spiess, et al., "Trehalose is a potent PCR enhancer: Lowering of DNA melting temperature and thermal stabilization of Taq polymerase by the disaccharide trehalose," in: Clinical Chemistry, 2004, pp. 1256-1259, vol. 50 (7).

Srinivasan, et al., "Matrix-assisted laser desorption/ionization time-of-flight mass spectrometry as a rapid screening method to detect mutations causing Tay-Sachs disease," Rapid Comm. Mass Spectrom, 1997, pp. 1144-1150, vol. 11 (10).

Steffens and Roy, "Sequence analysis of mitochondrial DNA hypervariable regions using infrared fluorescence detection," Bio/ Techniques, 1998, pp. 1044-1046, vol. 24 (6).

Stephensen, et al., "Phylogenetic analysis of a highly conserved region of the poymerase gene from 11 coronaviruses and development of a consensus poymerase chain reaction assay," Virus Res., 1999, pp. 181-189, vol. 60.

Stone Belinda et al., "Rapid detection and simultaneous subtype differentiation of influenza a viruses by real time PCR," Journal of Virological Methods, Elsevier BV, NL, 2004, pp. 103-112, vol. 117 (2).

Stoneking et al., "Population variation of human mtDNA control region sequences detected by enzymatic amplification and sequence-specific oligonucleotide probes," American Journal of Human Genetics, 1991, pp. 370-382, vol. 48.

Stratagene 1988 Catalog, p. 39.

Strommenger, B. et al., "Multiplex PCR Assay for Simultaneous Detection of Nine Clinically Relevant Antibiotic Resistance Genes in *Staphylococcus aureus* ," J. Clin. Microbiol., 2003, pp. 4089-4094, vol. 41 (9).

Studdert, M. J. et al., "Polymerase chain reaction tests for the identification of Ross River, Kunjinand Murray Valley encephalitis virus infections in horses," Aust. Vet. J., 2003, pp. 76-80, vol. 81 (1-2).

Stuhlmeier, R et al., "Fast, simultaneous, and sensitive detection of staphylococci.," J. Clin. Pathol, 2003, pp. 782-785, vol. 56.

Sumner et al., "PCR Amplification and Comparison of Nucleotide Sequences from the groESL Heat Shock Operon of *Ehrlichia* Species", Journal of Critical Microbiology, 1997, pp. 2087-2092, vol. 35.

Sundsfjord, A. et al., "Genetic methods for detection of antimicrobial resistance ," APMIS, 2004, pp. 815-837, vol. 112.

Supplementary European Search Report of EP Patent Application No. EP 02709785, dated Sep. 1, 2005, 5 pages total.

Supplementary European Search Report of EP Patent Application No. EP03796752 dated Aug. 7, 2007, 3 pages total.

Supplementary European Search Report of EP Patent Application No. EP03810055 dated Jun. 8, 2007, 4 pages total.

Supplementary European Search Report of EP Patent Application No. EP03814656 dated Oct. 16, 2007, 2 pages total.

Swaminathan, B., et al., "Emerging Infectious Diseases ," 2001, pp. 382-389, vol. 7.

Swanborg, R.H. et al, "Human herpesvirus 6 and *Chlamydia pneumoniae* as etiologic agents in multiplesclerosis—a critical review," Microbes and Infection, 2002, pp. 1327-1333, vol. 4.

Swenson, J. M. et al., "Performance of Eight Methods, Including Two New Rapid Methods, for Detection of Oxacillin Resistance in a Challenge Set of *Staphylococcus aureus* Organisms," J. Clin. Microbiol., 2001, pp. 3785-3788, vol. 39 (10).

Takagaki, Y. et al., "Four factors are required for 3'-end cleavage of pre-mRNAs ," Genes Dev., 1989, pp. 1711-1724, vol. 3.

Takahashi et al., "Characterization of gryA, gryB, grlA and grIB mutations in fluoroquinolone-resistant clinical isolates of *Staphylococcus aureus*", J. Antimicrob. Chemother, 1998 pp. 49-57, vol. 41 (1).

Takahata M, et al., "Mutations in the gyrA and grlA genes of quinolone-resistant clinical isolates ofmethicillin-resistant

*Staphylococcus aureus*," The Journal of Antimicrobial Chemotherapy, 1996, pp. 543-546, vol. 38 (3).

Takayama, R. et al., "Quantification of Adenovirus Species B and C Viremia by Real-Time PCR inAdults and Children Undergoing Stem Cell Transplantation," J. Med. Virol., 2007, pp. 278-284, vol. 79 (3).

Takeuchi et al., "Serotyping of Adenoviruses on Conjunctival Scrapings by PCR and Sequence Analysis ," Journal of Clinical Microbiology, 1999, pp. 1839-1845, vol. 37 (6).

Talaat et al., "Genome-directed primers for selective labeling of bacterial transcripts for DNA microarray analysis ," Nature Biotechnology, 2000, pp. 676-682, vol. 17.

Tan, T. Y et al, "Use of molecular techniques for the detection of antibiotic resistance in bacteria," Expert. Rev. Mot. Diagn., 2003, pp. 93-103, vol. 3 (1).

Tanabe, F. et al., "The Properties and mec A Gene of the Methicillin-Resistant *Staphylococcus aureus*Isolated in Fukushima Medical College Hospital," Fukushima J. Med. Sci, 1993, pp. 35-42, vol. 39 (1).

Tang, K, et al, "Detection of 500-Nucleotide DNA by Laser Desorption Mass Spectrometry," Rapid Commun. Mass Spectrom., 1994, pp. 727-730, vol. 8.

Tang, K. et al, "Double-Stranded DNA Analysisby Matrix Assisted Laser Desorption/Ionization ,'787 reexamination," 42nd ASMS Conference on Mass Spectrometry, 1994.

Tang K., et al,. "Matrix-Assisted Laser Desorption/Ionization of Restriction Enzyme-digested DNA", 8 Rapid Commun. Mass Spectrom, 183-186, 1994.

Tang, K. et al, "Matrix-Assisted Laser Desorption/Ionization Mass Spectrometry of Oligonucleotides ,787 reexamination," Dissertation submitted to the Faculty of Vanderbilt University, 1994.

Tarassishin, L. et al., "Adenovirus core protein VII displays a linear epitope conserved in a range of human adenoviruses," J. Gen. ViroL, 1999, pp. 47-50, vol. 80.

Tarassishin, L. et al., "An epitope on the adenovirus fibre tail is common to all human subgroups ," Arch. Virol., 2000, pp. 805-811, vol. 145.

Tatuch et al., "Heteroplasmic mtDNA mutation (T-G) at 8993 can cause Leigh disease when thepercentage of abnormal mtDNA is high," Am. J. Hum. Genet, 1992, pp. 852-858, vol. 50.

Taubenberger et al., "Characterization of the 1918 influenza virus polymerase genes," Nature, 2005, pp. 889-893, vol. 437.

Taylor, L.H., et al., "Philos. Trans. R. Soc. Lond B. Biol. Sci.," 2001, pp. 983-989, vol. 356.

Tenover, F. C. et al., "Characterization of a Strain of Community-Associated Methicillin-Resistant*Slaphylococcus aureus* Widely Disseminated in the United States," J. Clin.Microbiol., 2006, pp. 108-118, vol. 44 (1).

Teramura, T. et al., "Quantitative detection of serum adenovirus in a transplant recipient," Lancet, 2002, pp. 1945, vol. 359.

Thiel, et al., "Infectious RNA transcribed in vitro from a cDNA copy of the human coronavirus genome cloned in vaccinia virus," J. Gen. Virology, 2001, pp. 1273-1281, vol. 82.

Thompson et al., "ClustalW: Improving the sensitivity of progressive multiple sequence alignmen through sequence weighting, position-specific gap penalties and weight matrix choice," Nucleic Acid Res., 1994, pp. 4673-4680, vol. 22.

Thompson et al., "Influenza-Associated Hospitalizations in the United States ," JAMA, 2004, pp. 1333-1340, vol. 292.

Tokue, Y. et al., "Comparison of a Polymerase Chain Reaction Assay and a ConventionalMicrobiologic Method for Detection of Methicillin-Resistant *Slaphylococcus aureus* ," Antimicrob.Agents Chemother., 1992, pp. 6-9, vol. 36 (1).

Tong et al., "Ligation reaction specificities of an NAD+-dependent DNA ligase from the hyperthermophile Aquifex aeolicus," Nucleic Acids Res, 2000, pp. 1447-1454, vol. 28 (6).

Top, F., Jr., "Control of Adenovirus Acute Respiratory Disease in U.S. Army Trainees," Yale J. Biol. Med., 1975, pp. 185-195, vol. 48.

Torroni, Antonio et al., "Classification of European mtDNAs from an Analysis of Three European Populations," Genetics, 1996, pp. 1835-1850, vol. 144.

Towner, K. J. et al., "Development and evaluation of a PCRr-based immunoassay for the rapiddetection of methicillin-resistant *Staphylococcus aureus*," J. Med. Microbial., 1998, pp. 607-613, vol. 47.

Tsunoda et al., "Time and Memory Efficient Algorithm for Extracting Palindromic and RepetitiveSubsequences in Nucleic Acid Sequences," Pacific Symposium on Biocomputing, 1999, pp. 202-213, vol. 4.

Udo, E. E. et al., "A chromosomal location of the mupA gene in *Staphylococcus aureus* expressing high-level mupirocin resistance," J. Antimicrob. Chemother., 2003, pp. 1283-1286, vol. 51.

Udo, E. E. et al., "Genetic analysis of methicillin-resistant *Staphylococcus aureus* expressing high-and low-level mupirocin resistanceJ," Med. Microbiol, 2001, pp. 909-915, vol. 50.

Udo, E. E. et al., "Rapid detection of methicillin resistance in staphylococci using a slide latexagglutination kit," Int. J Antimicrob. Agents, 2000, pp. 19-24, vol. 15 (1).

Unal, S. et al., "Detection of Methicillin-Resistant Staphylococci by Using the PolymeraseChain Reaction," J. Clin. Microbiol, 1992, pp. 1685-1691, vol. 30 (7).

Unpublished U.S. Appl. No. 10/318,463 filed Dec. 13, 2002.
Unpublished U.S. Appl. No. 10/323,186 filed Dec. 18, 2002.
Unpublished U.S. Appl. No. 10/323,187 filed Dec. 18, 2002.
Unpublished U.S. Appl. No. 10/324,721 flied Dec. 18, 2002.
Unpublished U.S. Appl. No. 10/728,486 filed Dec. 5, 2003.
Unpublished U.S. Appl. No. 11/209,439 flied Aug. 23, 2005.
Unpublished U.S. Appl. No. 11/233,630 filed Sep. 2, 2005.
Unpublished U.S. Appl. No. 11/233,630 flied Sep. 21, 2005.
Unpublished U.S. Appl. No. 11/682,259 flied Mar. 5, 2007.
Unpublished U.S. Appl. No. 60/604,329 filed Aug. 24, 2004.
Unpublished U.S. Appl. No. 60/632,862 flied Dec. 3, 2004.
Unpublished U.S. Appl. No. 60/639,068 filed Dec. 22, 2004..
Unpublished U.S. Appl. No. 60/648,188 flied Jan. 28, 2005.
Unpublished U.S. Appl. No. 60/658,248 filed Mar. 3, 2005.
Unpublished U.S. Appl. No. 90/010,209 flied Jun. 27, 2008.
Unpublished U.S. Appl. No. 90/010,210 filed Jun. 27, 2008.

Upton, A. et al., "Mupirocin and *Staphylococcus aureus*: a recent paradigm of emergingantibiotic resistance," J. Antimicrob. Chemother., 2003, pp. 613-617, vol. 51.

Vabret, A., et al., "Development of a PCR-and hybridization-based assay (PCR AdenovirusConsensusA) for the detection and the species identification of adenoviruses in respiratoryspecimens," J. Clin. Virol, 2004, pp. 116-122, vol. 31 (2).

Van Aerschot A. et al., "In search of acyclic analogues as universal nucleosides in degenerate probes," Nucleosides and Nucleotides, 1995, pp. 1053-1056, vol. 14 (3-5).

Van Baar et al., "Characterization of bacteria by matrix assisted laser desorption/ionisation and electrospray mass spectrometry.," FEMS Microbiol. Reviews, 2000, pp. 193-219, vol. 24 (2).

Van Camp, et al., "Amplification and sequencing of variable regions in bacterial 23s ribosomal RNA genes with conserved primer sequences," Curr. Microbiol, 1993, pp. 147-151, vol. 27 (3).

Van Der Vossen et al., "DNA based typing identification and detection systems for food spoilagemicroorganisms: development and implementation," Int. J. Food Microbiol, 1996, pp. 35-49, vol. 33.

Van Der Zee, et al., "Rapid and alternative screening methods for microbiological analysis," J. AOAC Int., 1997, pp. 934-940, vol. 80.

Van Dinten et al., "Proteolytic Processing of the Open Reading Frame lb-EncodedPart of Arterivirus Replicase Is Mediated by nsp4 Serine Protease and Is Essential for Virus Replication," J. Virology, 1999, pp. 2027-2037, vol. 73.

Van Elden et al., "Clinical diagnosis of influenza virus infection: evaluation of diagnostic tools in general practice," Br. J. Gen. Pract, 2001, pp. 630-634, vol. 51.

Van Elden, L. J. R. et al., "Simultaneous Detection of Influenza Viruses A and B Using Real-Time Quantitative PCR," J. Clin. Microbiol, 2001, pp. 196-200, vol. 39 (1).

Van Ert, M.N. et al., "Mass spectrometry provides accurate characterization of two genetic marker types in *Bacillus anthracis*," Biotechniques, 2004, pp. 642-644, 646, 648, vol. 37 (4).

Van Leeuwen, W. B. et al., "Multilocus Sequence Typing of *Staphylococcus aureus* with DNA Array Technology," J. Clin. Microbiol, 2003, pp. 3323-3326, vol. 41 (7).

Van Leeuwen, W. B. et al., "Rapid Detection of Methicillin-Resistance in *Staphylococcus aureus* Isolates by the MRSA-Screen Latex Agglutination Test," J. Clin. Microbiol., 1999, pp. 3029-3030, vol. 37 (9).

Vanchiere et al., "Detection of BK virus and Simian virus 40 in the urine of healthy children," Journal of Medical Virology, 2005, pp. 447-454, vol. 75.

Vanderhallen et al. "Identification of Encephalomyocarditis Virus in Clinical Samples by ReverseTranscription-PCR Followed by Genetic Typing Using Sequence Analysis," J. Clin. Microbiol., 1998, pp. 3463-3467, vol. 36.

Vannuffel, P. et al., "Rapid and Specific Molecular Identification of Methicillin-Resistant *Staphylococcus aureus* in Endotracheal Aspirates from Mechanically Ventilated Patients," J Clin. Microbiol, 1998, pp. 2366-2368, vol. 36 (8).

Vannuffel, P. et al., "Specific Detection of Methicillin-Resistant *Staphylococcus* Species byMultiplex PCR," J. Clin Microbiol, 1995, pp. 2864-2867, vol. 33 (11).

Videla, C. et al., "Genomic analysis of adenovirus isolated from Argentinian children with acute lower respiratory infections," J. Clin. Virol, 1999, pp. 67-71, vol. 14.

Vilchez, Regis A. et al., "Detection of polyomavirus simian virus 40 tumor antigen DNA in AIDSrelated systemic non-Hodgkin lymphoma," J. Aids Journal of Acquired Immune Deficiencysyndromes, 2002, pp. 109-116, vol. 29 (2).

Voelter C et al., "Screening human tumor samples with a broad-spectrum polymerase chain reaction method for the detection of polyomaviruses," Virology, Academic Press,Orlando, US 1997, pp. 389-396, vol. 237 (2).

Volokhov et al., "Microarray analysis of erythromycin resistance determinants.," Journal of AppliedMicrobiology, 2003, pp. 787-798, vol. 95.

Von Eiff, C. et al., "Pathogenesis of infections due to coagulase-negative staphylococci," Lancet Infect. Dis., 2002, pp. 677-685, vol. 2.

Von Wintzingerode et al., "Base-specific fragmentation of amplified 16S rRNA genes analyzed by mass spectrometry: A tool for rapid bacterial identification," PNAS, 2002, pp. 7039-7044, vol. 99 (10).

W Payne et al., "Antimicrobials: The challenge of antibiotic resistant bacterial pathogens: the medical eed, the market and prospects for new antimicrobial agents.," Current Opinion in Microbiology, 2004, pp. 435-438, vol. 7.

Walker, E. S. et al., "A Decline in Mupirocin Resistance in Methicillin-Resistant *Staphylococcus aureus* Accompanied Administrative Control of Prescriptions," J. Clin. Microbiol., 2004, pp. 2792-2795, vol. 42 (6).

Wallace, et al., "The Enigma of Endonuclease VII.," DNA Repair, 2003, pp. 441-453, vol. 2.

Wallet, F. et al., "Choice of a routine method for detecting methicillin-resistance in staphylococci," Antimicrob. Chemother., 1996, pp. 901-909, vol. 37.

Walters et al., "Genotyping single nucleotide polymorphisms using intact polymerase chain reaction products by electrospray quadrupole mass spectrometry" Rapid Communications in Mass Spectrometry, 2001, pp. 1752-1759, vol. 15.

Wang, G. et al., "Targeted Mutagenesis in Mammalian Cells Mediated by Intracellular Triple Helix Formation," Mol. Cell. Biol., 1995, pp. 1759-1768, vol. 15 (3).

Ward C L et al., "Design and performance testing of quantitative real time PCR assays for influenza A and B viral load measurement ," Journal of Clinical Virology, Elsevier, Amsterdam, NL 2004, pp. 179-188, vol. 29 (3).

Weissenbacher, M. et al., "Etiologic and Clinical Evaluation of Acute Lower Respiratory TractInfections in Young Argentinean Children: An Overview," Rev. Infect. Dis., 1990, pp. S889-898, vol. 12Suppl.8.

Welham, K. J. et al., "The Characterization of Micro-organisms by Matrix-assisted Laser Desorption/Ionization Time-of-flight Mass Spectrometry," Rapid Commun. Mass Spec., 1998, pp. 176-180, vol. 12.

Wertheim, H. F. et al.., "Effect of Mupirocin Treatment on Nasal, Pharyngeal, and Perineal Carriage of *Staphylococcus aureus* in Healthy Adults," Antimicrob. Agents Chemother, 2005, pp. 1465-1467, vol. 49 (4).

Westermann, P. et al., "Inhibition of expression of SV40 virus large T-antigen by antisense oligodeoxyribonucleotides," Biomed. Biochim. Acta, 1989, pp. 85-93, vol. 1.

Whiley, David M. et al., "Simultaneous detection and differentiation of human polyomaviruses JC and BK by a rapid and sensitive PCR-ELAHA assay and a survey of the JCV subtypes within an Australian population," Journal of Medical Virology, 2004, pp. 467-472.

Wichelhaus, T. A. et al., "Rapid Detection of Epidemic Strains of Methicillin-Resistant*Staphylococcus aureus*," J. Clin. Microbiol, 1999, pp. 690-693, vol. 37 (3).

Wickham, T.J. et al., "Targeting adenovirus," Gene Therapy, 2000, pp. 110-114, vol. 7.

Widjojoatmodjo et al., "The magnetic Immuno polymerase chain reaction assay for direct detection of Salmonellae in fecal samples," J. Clin. Microbiol, 1992, pp. 3195-3199, vol. 30 (12).

Widjojoatmodjo, M. N. et al., "Rapid Identification of Bacterial by PCR-Single-Strand Conformation Polymorphism," J. Clin. Microbiol., 1994, pp. 3002-3007, vol. 32 (12).

Winger et al., "High resolution accurate mass measurements of biomolecules using a new electrospray ionization ion cyclotron resonance mass spectrometer," J. Am. Soc. Mass Spectrom., 1993, pp. 566-577, vol. 4 (7).

Wolter, et al., "Negative ion FAB mass spectrometric analysis of non-charged key intermediates in oligonucleotide synthesis: rapid identification of partially protected dinucleoside monophosphates," Biomed. Environ. Mass Spectrom, 1987, pp. 111-116, vol.

Woo, et al., "Identification of *Leptospira inadai* by continuous monitoring of fluorescence during rapid cycle PCR," System. App.l. Microbiol, 1998, pp. 89-96, vol. 21 (1).

Wood, S.R. et al., "Rapid Detection and Serotyping of Adenovirus by Direct Immunofluorescence," J.Med. Virol, 1997, pp. 198-201, vol. 51 (3).

Wright et al., "Typing and Subtyping of Influenza Viruses in Clinical Samples by PCR," Journal of Clinical Microbiology, 1995, pp. 1180-1184, vol. 33 (5).

Wu, et al., "Establishment of a fluorescent polymerase chain reaction method for the detection of SARS-associated coronavhus and its clinical application," Chln. Med. J., 2003, pp. 988-990, vol. 116.

Wu, et al., "Genetic Organization of the mecA Region in Methicillin-Susceptible and Methicillin-Resistant Strains of *Staphylococcus sciuri*," J. Bacteriol, 1998, pp. 236-242, vol. 180 (2).

Wunschel, D.S., et al., "Heterogeneity in *bacillus cereus* PCR products detected by ESI-FTICR mass spectrometry," Anal. Chem, 1998, pp. 1203-1207, vol. 70.

Wunschel, et al., "Analysis of double-stranded polymerase chain reaction products from the *Bacilus cereus* group by electrospray Ionization Fourier transform Ion cyclotron resonance mass spectrometry," Rapid Comm. Mass Spectrom, 1996, pp. 29-35, vol. 10.

Wunschel et al., "Discrimination Among the B. Cereus Group, in Comparison to B. Subtilis, by Structural Carbohydrate Profiles and Ribosomal RNA Spacer Region PCR," System. Appl. Microbiol., 1994, pp. 625-635, vol. 17.

Wunschel et al., "Mass spectrometric characterization of DNA for molecular biological app.lications: advances using MALDI and ESL," Advances in Mass Spectrometry, 1998, pp. Chapter 15/377-Chapter 15/406, vol. 14, Elsevier.

Xu et al., "Electrospray mass tag dideoxy DNA sequencing," Anal. Chem., 1997, pp. 3595-3602, vol. 69.

Xu, W. et al., "Species-Specific Identification of Human Adenoviruses by a Multiplex PCR Assay," J. Clin. Microbiol, 2000, pp. 4114-4120, vol. 38 (11).

Xu, W. et al., "Type-Specific Identification of Human Adenovirus, 3, 7, and 21 by a Multiplex PCR Assay," J. Med. Virol, 2001, pp. 537-542, vol. 64 (4).

Xu, X. et al.., "Intercontinental Circulation of Human Influenza A(H1 N2) Reassortant Viruses During the 2001-2002 Influenza Season," J. Infect. Dis., 2002, pp. 1490-1493, vol. 186.

Yao Z.P et al., "Mass Spectrometry Based Proteolytic Mapping for Rapid Virus Identification," Analytical Chemistry, American Chemical Society. Columbus, US, 2002, pp. 2529-2534, vol. 74 (11).

Yasui et al., "A specific oligonucleotide primer for the rapid detection of *Lactobacillus lindneri* by polymerase chain reaction,"Can. J. Microbiol., 1997, pp. 157-163, vol. 43 )2).

Ye, K. et al., "Three Distinct Promoters Direct Transcription of Different 5' Untranslated Regions of the Human Interleukin 1 Type 1

Receptor. A Possible Mechanism for Control of Translation," Cytokine, 1996, pp. 421-429, vol. 8 (6).
Yun, H J et al., "Increased antibacterial activity of OW286, a novel fluoronaphthyridone antibiotic, against *Staphylococcus aureus* strains with defined mutations in DNA gyrase and toposiomerase IV," International Journal of Antimicrobial Agents, Amsterdam.
Zeng et al., "Precision Mapping of Quantitative Trait Loci," Genetics, 1994, pp. 1457-1468, vol. 136.
Zhang, K. et al., "New Quadriplex PCR Assay for Detection of Methicillin and Mupirocin Resistance and Simultaneous Discrimination of *Staphylococcus aureus* from Coagulase-Negative Staphylococci," J. Clin. Microbiol., 2004, pp. 4947-4955, vol. 42 (11).
Zhang, W. D. et al., "Detection and identification of human influenza viruses by the polymerase chain reaction," J. Virol. Methods, 1991, pp. 165-189, vol. 33 (1-2).
Zhang, Y.-Q. et al., "Genome-based analysis of virulence genes in a non-biofilmforming *Staphylococcus epidemidis* strain (ATCC 12228)," Mol. Microbiol., 2003, pp. 1577-1593, vol. 49 (6).
Alba M.M., et al., "Vida: A Virus Database System for the Organization of Animal Virus Genome Open Reading Frames," Nucleic Acids Research, vol. 29 (1), pp. 133-136, 2001.
Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.
Benson D.A., et al., "GenBank," Nucleic Acids Research, 1999, vol. 27 (1), pp. 12-17.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Certificate of Correction mailed Jan. 6, 2009 for U.S. Appl. No. 10/660,996 filed Sep. 12, 2003.
Certificate of Correction mailed Aug. 7, 2007 for U.S. Appl. No. 10/660,997 filed Sep. 12, 2003.
Certificate of Correction mailed Dec. 12, 2006 for U.S. Appl. No. 10/156,608 filed May 24, 2002.
Certificate of Correction mailed Jul. 17, 2007 for U.S. Appl. No. 09/891,793 filed Jun. 26, 2001.
Certificate of Correction mailed Mar. 31, 2008 for U.S. Appl. No. 09/891,793, filed Jun. 26, 2001.
Certificate of Correction mailed Mar. 31, 2008 for U.S. Appl. No. 10/156,608 filed May 24, 2002.
Certificate of Correction mailed Mar. 31, 2008 for U.S. Appl. No. 10/660,997 filed Sep. 12, 2003.
Chinese Application No. CN1202204 filed Dec. 16, 1998, Sequenom Inc.
Chiu N. H., et al., "Mass Spectrometry of Single-Stranded Restriction Fragments Captured by an Undigested Complementary Sequence," Nucleic Acids Research, 2000, vol. 28 (8), pp. E31.
Collins D.W., et al., "Numerical Classification of Coding Sequences," Nucleic Acids Research, 1992, vol. 20 (6), pp. 1405-1410.
Co-pending U.S. Appl. No. 10/318,681, 2002.
Co-pending U.S. Appl. No. 10/521,662, 2003.
Co-pending U.S. Appl. No. 10/754,415, 2010.
Co-pending U.S. Appl. No. 10/807,019, 2004.
Co-pending U.S. Appl. No. 10/845,052, 2004.
Co-pending Appl. No. U.S. 10/964,571, 2004.
Co-pending U.S. Appl. No. 11/674,538, 2007.
Co-pending U.S. Appl. No. 11/929,910, 2010.
Co-pending U.S. Appl. No. 11/930,108, 2007.
Co-pending U.S. Appl. No. 11/930,741, 2007.
Co-pending U.S. Appl. No. 90/010,447, mailed on Dec. 9, 2009.
Co-pending Appl. No. US90/010,448, mailed Jun. 30, 2010.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Examiner Interview Summary mailed Oct. 3, 2005 for U.S. Appl. No. 10/326,046 filed Dec. 18, 2002.
Examiner Interview Summary mailed Nov. 6, 2008 for U.S. Appl. No. 10/728,486 filed Dec. 5, 2003.
Examiner Interview Summary mailed Feb. 27, 2006 for U.S. Appl. No. 10/326,644 filed Dec. 18, 2002.
Examiner Interview Summary mailed Jan. 27, 2006 for U.S. Appl. No. 10/323,211 filed Dec. 18, 2002.
Examiner Interview Summary mailed May 28, 2008 for U.S. Appl. No. 10/660,998 filed Sep. 12, 2003.
Examiner Interview Summary mailed Oct. 28, 2008 for U.S. Appl. No. 11/331,987 filed Jan. 13, 2006.
Examiner Interview Summary mailed Oct. 29, 2008 for U.S. Appl. No. 11/331,978 filed Jan. 13, 2006.
Examiner Interview Summary mailed Jul. 31, 2006 for U.S. Appl. No. 10/326,643 filed Dec. 18, 2002.
Examiner Interview Summary Record mailed Oct. 29, 2009 for U.S. Appl. No. 10/660,122 filed Sep. 11, 2003.
Final Office Action mailed Aug. 6, 2010 for U.S. Appl. No. 11/929,910 filed Oct. 30, 2007.
GenBank, "{Deletion 6} [Human, Muscle, Mitochondrial Mutant, 22 nt, Segment 2 of 2]," Accession No. S90302.1, Jun. 10, 1992.
GenBank, "Bovine parainfluenza virus 3 strain Shipping Fever, complete genome," Accesion No. AF178655, Sep. 19, 2000.
GenBank, "*Homo Sapiens* Haplotype V Mitochondrion, Complete Genome", Accession No. AF381990.1, Dec. 28, 2001.
GenBank, "Human Isolate L34 Mitochondrion D-loop Region", Accession No. U08081.1, Aug. 16, 1994.
GenBank, "il11b08.y1 Human insulinoma *Homo sapiens* cDNA clone Image:6029534 5-similar to SW:COX3_HUMAN P00414 Cytochrome C Oxidase Polypeptide III;, mRNA sequence", Accession No. BQ581956.1, Jun. 20, 2002.
GenBank, "or72a01.s1 NCI_CGAP_Lu5 *Homo sapiens* cDNA Clone Image:1601352 3-similar to SW:COX1_Human P00395 Cytochrome C Oxidase Polypeptide I;, mRNA sequemce", Accession No. AI002209.1, Jun. 10, 1998.
International Preliminary Examination Report for Application No. PCT/US2003/09802, mailed on Apr. 8, 2005, 7 pages.
International Preliminary Examination Report for Application No. PCT/US2003/22835, mailed on Mar. 5, 2005, 4 pages.
International Preliminary Report on Patentability and Written Opinion for Application No. PCT/US2005/030058, mailed on Aug. 20, 2007, 6 pages.
International Preliminary Report on Patentability for Application No. PCT/US2004/015196, mailed on Nov. 18, 2005, 1 page.
International Preliminary Report on Patentability for Application No. PCT/US2004/033742, mailed on Jun. 20, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009, 1 page.
International Preliminary Report on Patentability, Written Opinion and International Search Report for Application No. PCT/US2004/015123, mailed on Oct. 3, 2005, 8 pages.
Iteman I., et al., "Comparison of Conserved Structural and Regulatory Domains within Divergent 16S rRNA-23S rRNA Spacer Sequences of Cyanobacteria," Microbiology, vol. 146 (Pt 6), pp. 1275-1286.
Kasai H., et al., "Construction of the gyrB Database for the Identification and Classification of Bacteria," Genome Informatics. Workshop on Genome Informatics, 1998, pp. 13-21.
Kikuchi K., et al., "Restriction Fragment Length Polymorphism Analysis of Clinical Isolates of Mycobacterium Haemophilum," Journal of Clinical Microbiology, vol. 32 (7), pp. 1763-1767.
Kirpekar F., et al., "Matrix Assisted Laser Desorption/Ionization Mass Spectrometry of Enzymatically Synthesized RNA up to 150 kDa," Nucleic Acids Research, vol. 22 (19), pp. 3866-3870.
Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.
Laken S.J., et al., "Genotyping by Mass Spectrometric Analysis of Short DNA Fragments," Nature Biotechnology, 1998, vol. 16 (13), pp. 1352-1356.
Marks F., et al., "Genotyping of Plasmodium Falciparum Pyrimethamine Resistance by Matrix-Assisted Laser Desorption- Ionization Time-of-Flight Mass Spectrometry," Antimicrobial Agents and Chemotherapy, 2004, vol. 48 (2), pp. 466-472.

Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.

Non Final Rejection mailed Jun. 8, 2010 for U.S. Appl. No. 10/943,344 filed Sep. 17, 2004.

Non Final Rejection mailed Aug. 16, 2007 for U.S. Appl. No. 10/943,344 filed Sep. 17, 2004.

Non-Final Office Action mailed Aug. 4, 2010 for U.S. Appl. No. 12/049,949 filed Mar. 17, 2008.

Non-Final Office Action mailed Jun. 10, 2009 for U.S. Appl. No. 10/844,938 filed May 12, 2004.

Non-Final Office Action mailed Oct. 13, 2010 for U.S. Appl. No. 10/754,415 filed Jan. 9, 2004.

Non-Final Office Action mailed Dec. 29, 2010 for U.S. Appl. No. 12/616,422 filed Nov. 11, 2009.

Notice of Allowance mailed Jun. 3, 2009 for U.S. Appl. No. 11/331,978 filed Jan. 13, 2006.

Notice of Allowance mailed Aug. 5, 2010 for U.S. Appl. No. 11/233,630 filed Sep. 21, 2005.

Notice of Allowance mailed Aug. 6, 2009 for U.S. Appl. No. 10/728,486 filed Dec. 5, 2003.

Notice of Allowance mailed Dec. 10, 2010 for U.S. Appl. No. 11/233,630 filed Sep. 21, 2005.

Notice of Allowance mailed Dec. 10, 2010 for U.S. Appl. No. 11/491,376 filed Jul. 21, 2006.

Notice of Allowance mailed Nov. 12, 2009 for U.S. Appl. No. 10/728,486 filed Dec. 5, 2003.

Notice of Allowance mailed Dec. 15, 2008 for U.S. Appl. No. 11/331,978 filed Jan. 13, 2006.

Notice of Allowance mailed Sep. 18, 2009 for U.S. Appl. No. 10/660,998 filed Sep. 12, 2003.

Notice of Allowance mailed Nov. 24, 2009 for U.S. Appl. No. 11/331,978 filed Jan. 13, 2006.

Notice of Allowance mailed Oct. 29, 2009 for U.S. Appl. No. 10/660,122 filed Sep. 11, 2003.

Office Action mailed Feb. 2, 2011 for U.S. Appl. No. 11/869,449 filed Oct. 9, 2007.

Office Action mailed Aug. 3, 2007 for Chinese Application No. 200480016187.9 filed May 13, 2004.

Office Action mailed Feb. 3, 2011 for U.S. Appl. No. 12/326,800 filed Dec. 2, 2008.

Office Action mailed Dec. 4, 2006 for Indian Application No. 1136KOLNP2003 filed Mar. 4, 2002.

Office Action mailed May 4, 2010 for U.S. Appl. No. 90/010,447 filed Apr. 9, 2009.

Office Action mailed May 4, 2010 for U.S. Appl. No. 90/010,448 filed Apr. 9, 2009.

Office Action mailed Mar. 6, 2009 for U.S. Appl. No. 11/233,630 filed Sep. 21, 2005.

Office Action mailed Feb. 7, 2008 for European Application No. 03796752.8 filed Dec. 5, 2003.

Office Action mailed Jun. 7, 2010 for Australian Application No. 2008205432 filed Aug. 14, 2008.

Office Action mailed Jan. 8, 2007 for U.S. Appl. No. 09/891,793 filed Jun. 26, 2001.

Office Action mailed Sep. 8, 2006 for Chinese Application No. 02809122.1 filed Mar. 4, 2002.

Office Action mailed Dec. 9, 2009 for U.S. Appl. No. 90/010,210 filed Jun. 27, 2008.

Office Action mailed Dec. 9, 2009 for U.S. Appl. No. 90/010,447 filed Apr. 9, 2009.

Office Action mailed Dec. 9, 2009 for U.S. Appl. No. 90/010,448 filed Apr. 9, 2009.

Office Action mailed Feb. 9, 2009 for Chinese Application No. 02809122.1 filed Mar. 4, 2002.

Office Action mailed Jan. 9, 2008 for Japanese Application No. 2002570692 filed Mar. 4, 2002.

Office Action mailed Nov. 9, 2010 for U.S. Appl. No. 11/331,987 filed Jan. 13, 2006.

Office Action mailed Aug. 10, 2004 for U.S. Appl. No. 10/326,642 filed Dec. 18, 2002.

Office Action mailed Aug. 10, 2010 for Japanese Application No. 2006533082 filed May 13, 2004.

Office Action mailed Dec. 10, 2009 for U.S. Appl. No. 11/929,910 filed Oct. 30, 2007.

Office Action mailed Feb. 10, 2006 for Australian Application No. 2002244250 filed Mar. 4, 2002.

Office Action mailed Jun. 10, 2009 for U.S. Appl. No. 90/010,210 filed Jun. 27, 2008.

Office Action mailed Jun. 10, 2010 for U.S. Appl. No. 90/010,447 filed Apr. 9, 2009.

Office Action mailed Jun. 10, 2010 for U.S. Appl. No. 90/010,448 filed Apr. 9, 2009.

Office Action mailed Aug. 11, 2010 for U.S. Appl. No. 90/010,447 filed Apr. 9, 2009.

Office Action mailed Aug. 11, 2010 for U.S. Appl. No. 90/010,448 filed Apr. 9, 2009.

Office Action mailed Jun. 11, 2010 for U.S. Appl. No. 90/010,210 filed Jun. 27, 2008.

Office Action mailed May 12, 2002 for U.S. Appl. No. 09/798,007 filed Mar. 2, 2001.

Office Action mailed Aug. 13, 2009 for U.S. Appl. No. 11/674,538 filed Feb 13, 2007.

Office Action mailed Dec. 15, 2008 for Israel Application No. 157661 filed Mar. 4, 2002.

Office Action mailed Jan. 15, 2008 for Israel Application No. 157661 filed Mar. 4, 2002.

Office Action mailed Mar. 15, 2010 for European Application No. 08730682.5 filed Feb. 25, 2008.

Office Action mailed Apr. 16, 2009 for U.S. Appl. No. 90/010,210 filed Jun. 27, 2008.

Office Action mailed Mar. 16, 2010 for Canadian Application No. 2616281 filed Jul. 21, 2006.

Office Action mailed Nov. 16, 2006 for Australian Application No. 2004239340 filed May 13, 2004.

Office Action mailed Nov. 16, 2009 for Japanese Application No. 2005508488 filed Dec. 5, 2003.

Office Action mailed Sep. 17, 2008 for European Application No. 03796752.8 filed Dec. 5, 2003.

Office Action mailed Jan. 18, 2011 for U.S. Appl. No. 11/930,108 filed Oct. 31, 2007.

Office Action mailed May 18, 2005 for New Zealand Application No. 527857 filed Mar. 4, 2002.

Office Action mailed Sep. 18, 2008 for Australian Application No. 2003298030 filed Dec. 5, 2003.

Office Action mailed Feb. 20, 2007 for Korean Application No. 1020057021495 filed Nov. 11, 2005.

Office Action mailed Apr. 21, 2009 for U.S. Appl. No. 90/010,209 filed Jun. 27, 2008.

Office Action mailed Aug. 21, 2007 for Australian Application No. 2004239340 filed May 13, 2004.

Office Action mailed Oct. 21, 2005 for U.S. Appl. No. 10/326,641 filed Dec. 18, 2002.

Office Action mailed Sep. 22, 2010 for Canadian Application No. 2510007 filed Dec. 5, 2003.

Office Action mailed Apr. 23, 2010 for U.S. Appl. No. 90/010,210 filed Jun. 27, 2008.

Office Action mailed Jul. 23, 2009 for U.S. Appl. No. 11/070,632 filed Mar. 2, 2005.

Office Action mailed Oct. 23, 2003 for New Zealand Application No. 527857 filed Mar. 4, 2002.

Office Action mailed Aug. 24, 2010 for U.S. Appl. No. 90/010,210 filed Jun. 27, 2008.

Office Action mailed Dec. 24, 2004 for New Zealand Application No. 527857 filed Mar. 4, 2002.

Office Action mailed Feb. 24, 2004 for U.S. Appl. No. 10/32,6642 filed Dec. 18, 2002.

Office Action mailed Jan. 24, 2005 for U.S. Appl. No. 10/326,642 filed Dec. 18, 2002.

Office Action mailed Jul. 24, 2007 for Mexican Application No. PAA2003007927 filed Sep. 2, 2003.

Office Action mailed Jun. 24, 2008 for European Application No. 06800205.4 filed Jul. 27, 2006.
Office Action mailed Nov. 24, 2009 for U.S. Appl. No. 90/010,210 filed Jun. 27, 2008.
Office Action mailed Sep. 24, 2009 for U.S. Appl. No. 90/010,210 filed Jun. 27, 2008.
Office Action mailed Jun. 25, 2009 for U.S. Appl. No. 11/869,449 filed Oct. 9, 2007.
Office Action mailed Jun. 25, 2009 for U.S. Appl. No. 90/010,210 filed Jun. 27, 2008.
Office Action mailed Aug. 26, 2010 for Canadian Application No. 2508584 filed Dec. 5, 2003.
Office Action mailed Oct. 26, 2009 for European Application No. 04752257.8 filed May 13, 2004.
Office Action mailed Apr. 27, 2010 for Chinese Application No. 200480016187.9 filed May 13, 2004.
Office Action mailed Jul. 27, 2009 for Canadian Application No. 2439655 filed Mar. 4 2002.
Office Action mailed Jul. 28, 2010 for U.S. Appl. No. 90/010,210 filed Jun. 27, 2008.
Office Action mailed Mar. 29, 2010 for Australian Application No. 2006272776 filed Jul. 21, 2006.
Office Action mailed Jul. 30, 2009 for Japanese Application No. 2002570692 filed Mar. 4, 2002.
Office Action mailed Jun. 30, 2010 for U.S. Appl. No. 90/010,210 filed Jun. 27, 2008.
Office Action mailed Jun. 30, 2010 for U.S. Appl. No. 90/010,447 filed Apr. 9, 2009.
Office Action mailed Jun. 30, 2010 for U.S. Appl. No. 90/010,448 filed Apr. 9, 2009.
Office Action mailed Nov. 30, 2009 for U.S. Appl. No. 10/660,122 filed Sep. 11, 2003.
Office Action mailed Sep. 30, 2005 for Chinese Application No. 02809122.1 filed Mar. 4, 2002.
Office Action mailed Jan. 31, 2007 for Philippines Application No. PH12003500824 filed Mar. 4, 2002.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Partial European Search Report for Application No. EP01106974, mailed on Dec. 16, 2002, 2 pages.
Roberts M.S., et al., "Recombination and Migration Rates in Natural Populations of Bacillus Subtilis and Bacillus Mojavensis," Evolution, 1995, vol. 49 (6), pp. 1081-1094.
U.S. Appl. No. 60/369,405, 2002.
U.S. Appl. No. 60/397,365, 2002.
U.S. Appl. No. 60/431,319, 2002.
U.S. Appl. No. 60/443,443, 2003.
U.S. Appl. No. 60/443,788, 2003.
U.S. Appl. No. 60/447,529, 2003.
U.S. Appl. No. 60/453,607, 2003.
U.S. Appl. No. 60/461,494, 2003.
U.S. Appl. No. 60/470,175, 2003.
U.S. Appl. No. 60/501,926, 2003.
U.S. Appl. No. 60/509,911, 2003.
U.S. Appl. No. 60/615,387, 2005.
U.S. Appl. No. 60/701,404, 2005.
U.S. Appl. No. 60/705,631, 2005.
U.S. Appl. No. 60/720,843, 2005.
U.S. Appl. No. 60/747,607, 2006.
U.S. Appl. No. 60/771,101, 2006.
U.S. Appl. No. 60/773,124, 2006.
U.S. Appl. No. 60/891,479, 2007.
U.S. Appl. No. 60/941,641, 2007.
Verma S., et al., "Modified Oligonucleotides: Synthesis and Strategy for Users," Annual Review of Biochemistry, 1998, pp. 99-134.
Watanabe K., et al., "ICB Database: the gyrB Database for Identification and Classification of Bacteria," Nucleic Acids Research, 2001, vol. 29 (1), pp. 344-345.

Written Opinion for Application No. PCT/US2004/015196, mailed on Jul. 1, 2005, 3 pages.
Zhang J., et al., "PowerBLAST: A New Network BLAST Application for Interactive or Automated Sequence Analysis and Annotation," Genome Research, 1997, vol. 7 (6), pp. 649-656.
Ex Parte Re-Examination Certificate for U.S. Appl. No. 90/010,447 mailed Feb. 15, 2011.
Office Action mailed Feb. 16, 2011 for U.S. Appl. No. 11/929,910 filed Oct. 30, 2007.
Boivin-Jahns et al., "Bacterial Diversity in a Deep-Subsurface Clay Environment," App.lied and Environmental Microbiology, 1996, pp. 3405-3412, vol. 62 (9).
Bolton et al., "A general method for the isolation of RNA complementary to DNA", Proc. Natl. Acad. Sci. U.S.A, 1962, pp. 1390-1397, vol. 48.
Bonk Thomas et al., "Matrix-assisted laser desorption/ionization time-of-flight mass spectrometry-based detection of microsatellite instabilities in coding DNA sequences: a novel approach to identify DNA-mismatch repair-deficient cancer cells," Clinical Chem, 2003.
Borrow et al., "SiaD PCR Elisa for confirmation and identification of serogroup Y and W135 meningococcal infections," FEMS Microbiological Letters, 1998, pp. 209-214, vol. 159.
Boubaker, K. et al., "Panton-Valentine Leukocidin and Staphylococcal Skin Infections in Schoolchildren," Emerg. Infect. Dis., 2004, pp. 121-124, vol. 10 (1).
Bowen, J.E., et al., "The native virulence plasmid combination affects the segregational stability of a thetareplicating shuttle vector in bacillus anthracis var, New Hampshire," J. App.l. Microbiol, 1999, pp. 270-278, vol. 87 (2).
Bowers, K. M. et al., "Screening for methicillin resistance in Staphylococars aureus and coagulasenegative staphylococci: evaluation of three selective and Mastalex-MRSA latex agglutination," Br. J. Biomed. Sci., 2003, pp. 71-74, vol. 60 (2).
Brakstad, O.G, et al., "Direct identification of Staphylococcus aureus in blood cultures bydetection of the gene, encoding the thermostable nuclease or the gene product," APMIS, 1995, pp. 209-218, vol. 103.
Brakstad, O.G, et al., "Multiplex polymerase chain reaction for detection of genes for Staphylococcus aureus themonuclease and methicillin resistance and correlation with oxacillin resistance," APMIS, 1993, pp. 681-688, vol. 101.
Brandt, C. D. et al., "Infections in 18,000 Infants and Children in a Controlled Study of Respiratory Tract Disease. I. Adenovirus Pathogenicity in Relation to Serologic Type and Illness Syndrome," Am. J. Epidemiol, 1969, pp. 484-500, vol. 90 (6).
Brayshaw, D. P, "Methicillin-resistant Staphylococcus aureus: evaluation of detection techniques on laboratory-passaged organisms," Br. J. Biomed. Sci., 1999, pp. 170-176, vol. 56.
Brightwell, G. et al., "Development of internal controls for PCR detection of Bacillus anthracis Molecular and Cellular Probes," Academic Press, London, GB, 1998, pp. 367-377, vol. 12 (6).
Brightwell, G. et al., "Genetic targets for the detection and identifiaction of Venezuelan equine encephalitis viruses," Arch. Virol, 1998, pp. 731-742, vol. 143 (4).
Bronzoni, R. V. M. et al., Duplex Reverse Transcription-PCR Followed by Nested PCR.
Katayama, Y. et al., Genetic Organization of the Chromosome Region Surrounding mecA inClinical Staphylococcal Strains: Role of IS431-Mediated mecl Deletion in Expression of Resistance inmed-Canying, Low-Level Methicillin-Resistant Staphylococcus haemoly, Antimicrob Agents Chemother., vol. 45, pp. 1955-1963, 2001.
Yun, H J et al., "Increased antibacterial activity of OW286, a novel fluoronaphthyridone antibiotic, against Staphylococcus aureus strains with defined mutations in DNA gyrase and toposiomerase IV," International Journal of Antimicrobial Agents, Amsterdam., vol. 25, 2005.
Schwartz, M, et al., Prenatal diagnosis of alpha-1-antitrypsin deficiency using polymerase chainreaction (PCR). Comparison of conventional RFLP methods with PCR used in combination with allelespecific oligonucleotides or RFLP analysis, '787 reexamination., Cain Genet., vol. 36(6), pp. 419-426, 1989.

\* cited by examiner

METHOD FOR RAPID PURIFICATION OF NUCLEIC ACIDS FOR SUBSEQUENT ANALYSIS BY MASS SPECTROMETRY BY SOLUTION CAPTURE

CROSS-REFERENCE TO RELATED APPLICATIONS

This application claims the benefit of priority to U.S. provisional application Ser. No. 60/470,547 filed May 13, 2003, which is incorporated herein by reference in its entirety.

STATEMENT OF GOVERNMENT SUPPORT

This invention was made with United States Government support under Centers for Disease Control grant RO1 CI000099-01. The United States Government may have has certain rights in the invention.

FIELD OF THE INVENTION

The present invention relates generally to the field of analysis of nucleic acids by mass spectrometry and provides methods and kits useful for this purpose.

BACKGROUND OF THE INVENTION

Electrospray ionization mass spectrometry (ESI-MS) has become an important technique for the analysis of biopolymers. The multiple charging phenomenon allows fast, accurate and precise molecular mass measurement, identification of modifications and more detailed structural studies for very high-mass biopolymers.

Amplification of specific DNA sequences utilizing the polymerase chain reaction has widespread applications in many scientific disciplines, including microbiology, medical research, forensic analysis, and clinical diagnostics. Most often, PCR products are "sized" using traditional biochemical techniques such as standard gel electrophoresis using either intercalating dyes or fluorescently labeled primers. The Taqman™ assay, which is widely used in a number of PCR-based diagnostic kits, confirms the presence (or absence) of a specific PCR product but provides no direct readout on the size of the amplicon. So-called "real-time" PCR devices, which measure the laser-induced fluorescence of the PCR product during the amplification cycles, are used to quantify the amplification of DNA from a given DNA template and primer set. These methods have limited utility for relatively small amplicons (less than 150 base pairs), owing to the proportionately high fluorescence background, and do not provide any information with respect to amplicon heterogeneity or exact length.

Compared to these more traditional methods, mass spectrometry has several potential advantages as a platform on which to characterize PCR products, including speed, sensitivity, and mass accuracy. Because the exact mass of each of the bases which comprise DNA is known with great accuracy, a high-precision mass measurement obtained via mass spectrometry can be used to derive a base composition within the experimentally obtained mass measurement uncertainty (J. Aaserud, Z. Guan, D. P. Little and F. W. McLafferty, *Int. J. Mass Spectrom. Ion Processes,* 1997, 167/168, 705-712. and D. C. Muddiman, G. A. Anderson, S. A. Hofstadler and R. D. Smith, *Anal. Chem.* 1997, 69, 1543-1549). Methods for rapid identification of unknown bioagents using a combination of nucleic acid amplification and determination of base composition of informative amplicons by molecular mass analysis are disclosed and claimed in published U.S. patent applications 20030027135, 20030082539, 20030124556, 20030175696, 20030175695, 20030175697, and 20030190605 and U.S. patent application Ser. Nos. 10/326, 047, 10/660,997, 10/660,122 and 10/660,996, all of which are commonly owned and incorporated herein by reference in entirety.

Both MALDI (matrix assisted, laser desorption ionization) and electrospray (ESI) mass spectrometry have been employed to ionize PCR products for subsequent mass spectrometric detection. While MALDI is widely used to analyze short (20-mer or smaller) oligonucleotides, applications to amplicons in excess of 100 bp are less common. ESI is one of the most widely used ionization techniques for large biological molecules owing to the inherent "softness" of the ionization process, which allows DNA in excess of 500 bp to be ionized without dissociation.

In ESI, large charged droplets are produced in the process of "pneumatic nebulization" where the analyte solution is forced through a needle at the end of which is applied a potential sufficient to disperse the emerging solution into a very fine spray of charged droplets all of which have the same polarity. The solvent evaporates, shrinking the droplet size and increasing the charge concentration at the droplet's surface. Eventually, at the Rayleigh limit, Coulombic repulsion overcomes the droplet's surface tension and the droplet explodes. This "Coulombic explosion" forms a series of smaller, lower charged droplets. The process of shrinking followed by explosion is repeated until individually charged analyte ions are formed. The charges are statistically distributed amongst the analyte's available charge sites, leading to the possible formation of multiply charged ions conditions. Increasing the rate of solvent evaporation, by introducing a drying gas flow counter current to the sprayed ions, increases the extent of multiple-charging. Decreasing the capillary diameter and lowering the analyte solution flow rate i.e. in nanospray ionization, will create ions with higher m/z ratios (i.e. it is a softer ionization technique) than those produced by "conventional" ESI and are of much more use in the field of bioanalysis.

Unfortunately, ESI requires relatively clean samples and is notoriously intolerable of cationic salts, detergents, and many buffering agents commonly used in biochemical laboratories.

The buffer system commonly employed in the polymerase chain reaction includes electrospray incompatible reagents such as 50 mM KCl, 2 mM $MgCl_2$, 10 mM Tris-HCl, and each of the four deoxynucleotide triphosphates (dNTPs) at 200 µM. Even the presence of relatively low concentrations of metal cations (less than 100 µM) can significantly reduce MS sensitivity for oligonucleotides as the signal for each molecular ion is spread out over multiple salt adducts. Thus, in addition to removing detergents and dNTPs, effective ESI-MS of PCR products requires that the salt concentration be reduced by more than a factor of 1000 prior to analysis.

Ethanol precipitation has been used to desalt PCR products for subsequent MS analysis as short oligonucleotides and salts are removed while the sample is concentrated (M. T. Krahmer, Y. A. Johnson, J. J. Walters, K. F. Fox, A. Fox and M. Nagpal, Electrospray Anal. Chem. 1999, 71, 2893-2900; T. Tsuneyoshi, K. Ishikawa, Y. Koga, Y. Naito, S. Baba, H. Terunuma, R. Arakawa and D. J. Prockop *Rapid Commun. Mass Spectrom.* 1997, 11, 719-722; and D. C. Muddiman, D. S. Wunschel, C. L. Liu, L. Pasatolic, K. F. Fox, A. Fox, G. A. Anderson and R. D. Smith *Anal. Chem.* 1996, 68, 3705-3712). In this method, the PCR product can be precipitated from concentrated ammonium acetate solutions, either overnight at 5° C. or over the course of 10-15 min with cold (−20°

C.) ethanol. Unfortunately, a precipitation step alone is generally insufficient to obtain PCR products which are adequately desalted to obtain high-quality ESI spectra; consequently, precipitation is generally followed by a dialysis step to further desalt the sample (D. C. Muddiman, D. S. Wunschel, C. L. Liu, L. Pasatolic, K. F. Fox, A. Fox, G. A. Anderson and R. D. Smith *Anal. Chem.* 1996, 68, 3705-3712). While several researchers have successfully employed these methods to characterize a number of PCR products, the route to applying these methods in a robust and fully automated high-throughput manner is not obvious.

Commercial DNA purification kits may also be used in conjunction with traditional desalting techniques such as microdialysis (S. Hahner, A. Schneider, A. Ingendoh and J. Mosner *Nucleic Acids Res.* 2000, 28, e82/i-e82/viii; and A. P. Null, L. T. George and D. C. Muddiman *J. Am. Soc. Mass Spectrom.* 2002, 13, 338-344). Other purification techniques, such as gel electrophoresis followed by high-performance liquid chromatography or drop dialysis, or cation exchange using membranes or resins have also been used to obtain high-purity, desalted DNA for MS detection (L. M. Benson, S.-S. Juliane, P. D. Rodringues, T. Andy, L. J. Maher III and S. Naylor, In: *The 47th ASMS Conference on Mass Spectrometry and Allied Topics*, Dallas, Tex. (1999); C. G. Huber and M. R. Buchmeiser *Anal. Chem.* 1998, 70, 5288-5295; H. Oberacher, W. Parson, R. Muehlmann and C. G. Huber *Anal. Chem.* 2001, 73, 5109-5115; and C. J. Sciacchitano *J. Liq. Chromatogr. Relat. Technol.* 1996, 19, 2165-2178). Unfortunately, as with the techniques described above, the path toward a rapid and fully automated high-throughput implementation is not obvious.

Jiang and Hofstadler have developed and reported a single protocol for the purification and desalting of PCR products which employs commercially available pipette tips packed with anion exchange resin (Y. Jiang and S. A. Hofstadler *Anal. Biochem.* 2003, 316, 50-57). This protocol yields an ESI-MS-compatible sample and requires only 10 µl of crude PCR product. However, the method is cost-prohibitive when applied to high volume and high throughput processes such as the methods cited above for identification of unknown bioagents. Retail costs of using the commercially-obtained ZipTip™ AX (Millipore Corp. Bedford, Mass.) are estimated at $1.77 per plate well.

There remains a need for a method of purification of nucleic acids for mass spectrometry which is rapid, efficient and non-cost prohibitive. The present invention satisfies this need.

Solution capture of nucleic acids such as those obtained from amplification reactions has enabled a rapid, cost-effective method of extracting and purifying these analytes for subsequent analysis by mass spectrometry. Since the nucleic acids and the anion exchange media are in solution, efficient capture of the nucleic acids is accomplished by vortexing, or other mixing methods. This has eliminated the need to pack the media in a column format which would require multiple passes of the nucleic acid solution over it to achieve high levels of recovery of nucleic acids. While longer columns require fewer passes, significant backpressure becomes a problem. The process of packing an anion exchange resin in a column or pipette tip format increases the cost associated with the procedure accordingly. Thus the use of solution capture for purification of PCR products for analysis by mass spectrometry has substantially reduced the cost associated with sample preparation by eliminating the need to pack, equilibrate, and test a column. The retail cost of the current procedure using a pipette tip packed with anion exchange resin exemplified by ZipTip™ AX (Millipore, Bedford, Mass.) is approximately $1.77 per pipette tip (for each sample). The estimated cost of solution capture of PCR products is $0.10 per sample and takes into account the combination of anion exchange resin and filter plate. Furthermore, the time required for solution capture purification of PCR products is approximately 10 minutes per 96 well plate in contrast to the previous method which employs the ZipTip™ AX pipette tips and requires approximately 20 minutes.

SUMMARY OF THE INVENTION

The present invention is directed to, inter alia, solution capture methods of purifying a solution comprising one or more nucleic acids for subsequent analysis by electrospray mass spectrometry, or any other analysis, by adding an anion exchange resin to the solution and mixing to yield a suspension of the anion exchange resin in the solution wherein the nucleic acid binds to the anion exchange resin, isolating the anion exchange resin from the solution, washing the anion exchange resin to remove one or more contaminants with one or more wash buffers while retaining bound nucleic acid, eluting the nucleic acid, from the ion exchange resin with an elution buffer, and optionally, analyzing the nucleic acids by electrospray mass spectrometry.

The anion exchange resin may have a strong anion exchange functional group such as a quaternary amine or a weak anion exchange functional group such as, for example, polyethyleneimine, charged aromatic amine, diethylaminomethyl, or diethylaminoethyl. Such weak anion exchange resins comprise functional groups with $pK_a$ values of 9.0 or greater.

The present invention is further directed to kits for purification of nucleic acids comprising a filter plate comprising a plurality of wells or a tube rack comprising a plurality of tubes, an anion exchange resin, at least one anion exchange wash buffer and an ESI-MS-compatible elution buffer.

DESCRIPTION OF EMBODIMENTS

Figure 1:
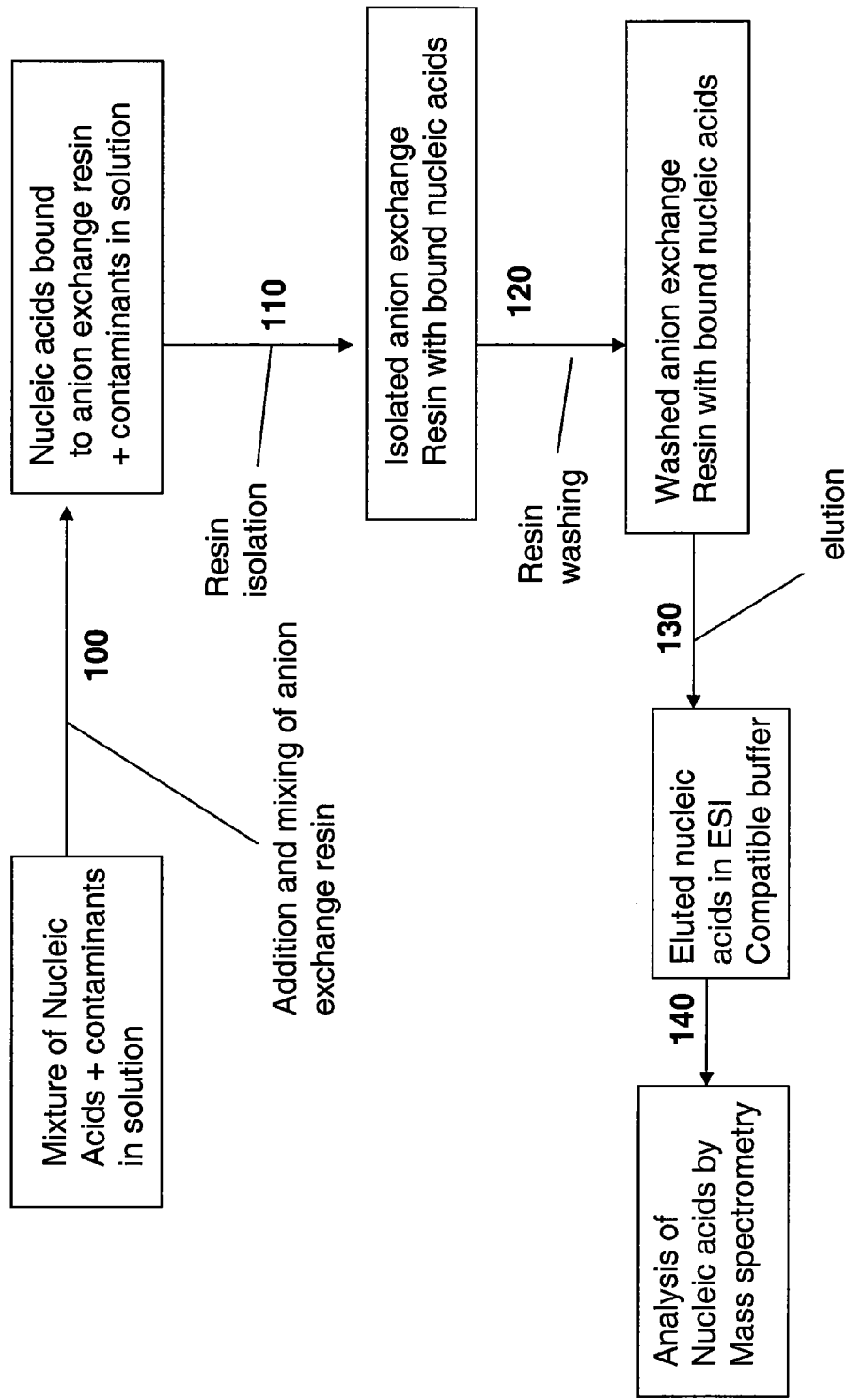
FIG. 1 is a process diagram outlining the steps of the present invention beginning with the addition and mixing of anion exchange resin into the sample of nucleic acids (100). The resin is then isolated from the solution (110) and washed with an appropriate wash buffer to remove contaminants from the resin (120) after which, the nucleic acids are eluted from the resin by an electrospray ionization (ESI)-compatible elution buffer, which makes possible the final step of analysis of the nucleic acids by ESI-mass spectrometry (140).

One embodiment of the method of solution capture purification of nucleic acids for analysis by mass spectrometry, for example, is outlined in FIG. 1. The methods described herein can be used for other types of analysis, in addition to mass spectrometry as known to those skilled in the art. The methods comprise the following steps: Addition and mixing of an anion exchange resin into a solution of nucleic acids (100), isolating the anion exchange resin from the solution (110), washing the anion exchange resin to remove contaminants (120), eluting the nucleic acids, (free of contaminants) from the anion exchange resin (130), and, optionally, analyzing the nucleic acid by ESI mass spectrometry.

In some embodiments, a strong cation exchange functional group, such as a quaternary amine for example, is employed as the functional group of the anion exchange resin. Additional strong anion exchange functional groups are known to those skilled in the art.

In other embodiments, a weak anion exchange functional group is a suitable anion exchange functional group, such as polyethyleneimine, charged aromatic amine, diethylaminomethyl, or diethylaminoethyl, for example, are employed as the functional group of the anion exchange resin. Such functional groups have $pK_a$ values of 9.0 or greater. Commercial products of weak anion-exchange resin include, but are not limited to; Baker PEI, Baker DEAM, Dionex ProPac™ WAX, Millipore PEI, Applied Biosystems Poros™ PI.

In some embodiments, the mixing of the anion exchange resin into the solution of nucleic acids is effected by repeated pipetting, vortexing, sonication, shaking, or any other method that results in suspension of the anion exchange resin in the solution containing the nucleic acids.

In some embodiments, dry anion exchange resin is added directly to the solution of nucleic acids or contained within a microtube or the well of a micro filter plate into which the solution of nucleic acids is added prior to mixing. In other embodiments, the anion exchange resin is pre-hydrated and added directly to the solution of nucleic acids or contained within a microtube or a well of a microfilter plate into which the solution of nucleic acids is added prior to mixing.

In some embodiments, the anion exchange resin which contains bound nucleic acids is isolated from the solution by filtration. Filtration can be effected, for example, using a filter plate in a 96- or 384-well format which enables high-throughput purification of multiple samples, or in any other container or plurality of containers equipped with a filter. Other well format plates can also be used. Membranes useful for filtration include but are not limited to those composed of the following materials: polytetrafluoroethylene (PTFE), polyvinyldifluoro (PVDF), polypropylene, polyethylene, glass fiber, polycarbonate and polysulfone. Filtering may be accomplished by vacuum, centrifugation, or positive pressure displacement with fluids or gases, or any other method that effects the isolation of the anion exchange resin from the solution. Methods of filtering are well known to those skilled in the art.

In some embodiments, the anion exchange resin comprises an anion exchange functional group which is linked to magnetic beads. Such an arrangement enables a simpler isolation step (110) by eliminating the need for centrifugation, vacuum or positive pressure displacement which would necessitate the removal of the plate or microtube tube from the liquid handler deck. Instead, a magnetic field can be activated to compress the magnetic bead resin so that liquid can be aspirated off by the liquid handler. Methods of using magnetic beads to effect isolation of biomolecules are well known to those skilled in the art.

In some embodiments, the anion exchange resin which contains bound nucleic acids is washed to remove one or more contaminants. Contaminants include, but are not limited to: proteins such as reverse transcriptase and restriction enzymes, polymers, salts, buffer additives, or any of the various components of an amplification reaction such as polymerases nucleotide triphosphates or any combination thereof. Depending on the composition of the contaminants in the nucleic acid solution, more than one wash buffer may be useful for removal of contaminants. Washing of the anion exchange resin can be effected with aqueous solutions of ammonium acetate in the millimolar range from about 20 mM to about 500 mM $NH_4OAc$ or with about 20 mM to about 500 mM $NH_4HCO_3$. Washing with about 10% to about 50% methanol, about 20% to about 50% methanol, or about 10% to about 30% methanol is useful as a final wash step. Methanol can be replaced by other suitable alcohols known to those skilled in the art.

In some embodiments, elution of nucleic acids from the anion exchange resin is accomplished using an ESI-compatible solution at alkaline pH of about pH 9 or greater such as an aqueous solution of about 2% to about 8% ammonium hydroxide or an aqueous solution of about 10 mM to about 50 mM, or 25 mM piperidine, about 10 mM to about 50 mM, or 25 mM imidazole and about 30% methanol or other suitable alcohol. As defined herein, an ESI-compatible solution is a solution which does not have a detrimental effect on the function of an electrospray (ESI) source.

As used herein, the term "about" means±10% of the term being modified. Thus, for example, "about" 10 mM means 9 to 11 mM.

In another embodiment, the present invention also provides kits for purification of nucleic acids by the solution capture method of the present invention. In some embodiments, the kit may comprise a sufficient quantity of anion exchange resin. In some embodiments, the anion exchange resin is a weak anion exchange resin such as one of the following commercially available weak anion exchange resins: Baker polyethyleneimine resin, Baker diethylaminomethyl resin, Dionex ProPac™ WAX, Millipore polyethyleneimine, and Applied Biosystems POROS™ PI.

In some embodiments, the kit may comprise a filter plate such as a 96- or 384-well filter plate or a microtube rack comprising a plurality of micro filter tubes.

In some embodiments, dry anion exchange resin is pre-loaded into the wells of a filter plate or microtube rack and can be either pre-hydrated or in the dry (powder) form.

The kit may also comprise a filter plate comprising a plurality of wells or a tube rack comprising a plurality of tubes, an anion exchange resin, at least one anion exchange wash buffer and an ESI-MS-compatible elution buffer.

In one embodiment, the kit may comprise a 96 or 384 well plate containing either pre-hydrated anion exchange resin or dry anion exchange resin, a second 96 or 384 well sample mixing plate, a 96 or 384 well filter plate, a resin treatment buffer, one or more wash buffers, and an ESI-compatible elution buffer.

In one embodiment, the nucleic acid solution is a PCR product prepared for identification of an unknown bioagent and contained in an individual well of a 96 well sample plate on the deck of an automated liquid handler. The liquid handler is the cornerstone for many laboratory processes associated with drug discovery and high throughput screening. The dispensing and aspiration functions of liquid handlers are used to perform solvent/reagent additions, dilutions, plate replications consolidation, redistribution and other microplate-based tasks and typically use disposable pipette tips for transferring liquids. Programming of liquid handlers to perform the various liquid handling tasks of this embodiment is well within the capabilities of one with ordinary skill in the art without undue experimentation.

The liquid handler is programmed to transfer and mix a predetermined volume of a suspension of anion exchange resin into the well containing the PCR product. The resin suspension can be contained in a resin source container such a 96 well plate and transferred to the PCR product plate by the liquid handler. Mixing is performed by the liquid handler via repeated dispensation and aspiration of the PCR-resin mixture and binding of nucleic acids to the resin occurs at this stage. Next, the liquid handler transfers the PCR product-resin mixture from the 96 well plate to a 96 or 384 well filter plate. At this stage, the filter plate can be removed from the liquid handler deck and the resin can be isolated from the solution by centrifugation or positive pressure displacement before returning the filter plate to the liquid handler deck.

The resin containing bound nucleic acids is then washed one or more times with an appropriate wash solution such as about 100 mM $NH_4HCO_3$ with the liquid handler pipetting the wash solution into the filter plate, followed by centrifugation, vacuum, or positive pressure displacement followed by one or more washes with about 20% to about 50% methanol before returning the filter plate containing the resin and bound nucleic acids to the liquid handler deck.

Finally, the nucleic acids are eluted from the resin with an ESI compatible elution buffer such as an aqueous solution of about 25 mM piperidine, about 25 mM imidazole and about 50% methanol. This ESI compatible buffer may also optionally contain an internal standard used to calibrate the ESI mass spectrometer during the subsequent ESI mass spectrometry analysis.

In order that the invention disclosed herein may be more efficiently understood, examples are provided below. It should be understood that these examples are for illustrative purposes only and are not to be construed as limiting the invention in any manner. Throughout these examples, molecular cloning reactions and other standard recombinant DNA techniques were carried out according to methods described in Maniatis et al., Molecular Cloning—A Laboratory Manual, $2^{nd}$ ed. Cold Spring Harbor Press (1989), using commercially available reagents except where otherwise noted.

EXAMPLES

Example 1

Nucleic Acid Isolation and PCR

In one embodiment, nucleic acid is isolated from the organisms and amplified by PCR using standard methods prior to BCS determination by mass spectrometry. Nucleic acid is isolated, for example, by detergent lysis of bacterial cells, centrifugation and ethanol precipitation. Nucleic acid isolation methods are described in, for example, *Current Protocols in Molecular Biology* (Ausubel et al.) and *Molecular Cloning; A Laboratory Manual* (Sambrook et al.). The nucleic acid is then amplified using standard methodology, such as PCR, with primers which bind to conserved regions of the nucleic acid which contain an intervening variable sequence as described below.

General Genomic DNA Sample Prep Protocol: Raw samples are filtered using Supor-200 0.2 μM membrane syringe filters (VWR International). Samples are transferred to 1.5 ml eppendorf tubes pre-filled with 0.45 g of 0.7 mm Zirconia beads followed by the addition of 350 μl of ATL buffer (Qiagen, Valencia, Calif.). The samples are subjected to bead beating for 10 minutes at a frequency of 19 I/s in a Retsch Vibration Mill (Retsch). After centrifugation, samples are transferred to an S-block plate (Qiagen) and DNA isolation is completed with a BioRobot 8000 nucleic acid isolation robot (Qiagen).

Swab Sample Protocol: Allegiance S/P brand culture swabs and collection/transport system are used to collect samples. After drying, swabs are placed in 17×100 mm culture tubes (VWR International) and the genomic nucleic acid isolation is carried out automatically with a Qiagen Mdx robot and the Qiagen QIAamp DNA Blood BioRobot Mdx genomic preparation kit (Qiagen, Valencia, Calif.).

Example 2

Mass Spectrometry

The mass spectrometer used is a Bruker Daltonics (Billerica, Mass.) Apex II 70e electrospray ionization Fourier transform ion cyclotron resonance mass spectrometer (ESI-FTICR-MS) that employs an actively shielded 7 Tesla superconducting magnet. All aspects of pulse sequence control and data acquisition were performed on a 1.1 GHz Pentium II data station running Bruker's Xmass software. 20 μL sample aliquots were extracted directly from 96-well microtiter plates using a CTC HTS PAL autosampler (LEAP Technologies, Carrboro, N.C.) triggered by the data station. Samples were injected directly into the ESI source at a flow rate of 75 μL/hr. Ions were formed via electrospray ionization in a modified Analytica (Branford, Conn.) source employing an off axis, grounded electrospray probe positioned ca. 1.5 cm from the metalized terminus of a glass desolvation capillary. The atmospheric pressure end of the glass capillary is biased at 6000 V relative to the ESI needle during data acquisition. A countercurrent flow of dry $N_2/O_2$ was employed to assist in the desolvation process. Ions were accumulated in an external ion reservoir comprised of an rf-only hexapole, a skimmer cone, and an auxiliary gate electrode, prior to injection into the trapped ion cell where they were mass analyzed.

Spectral acquisition was performed in the continuous duty cycle mode whereby ions were accumulated in the hexapole ion reservoir simultaneously with ion detection in the trapped ion cell. Following a 1.2 ms transfer event, in which ions were transferred to the trapped ion cell, the ions were subjected to a 1.6 ms chirp excitation corresponding to 8000-500 m/z. Data was acquired over an m/z range of 500-5000 (1M data points over a 225K Hz bandwidth). Each spectrum was the result of co-adding 32 transients. Transients were zero-filled once prior to the magnitude mode Fourier transform and post calibration using the internal mass standard. The ICR-2LS software package (G. A. Anderson, J. E. Bruce (Pacific Northwest National Laboratory, Richland, Wash., 1995) was used to deconvolute the mass spectra and calculate the mass of the monoisotopic species using an "averaging" fitting routine (M. W. Senko, S. C. Beu, F. W. McLafferty, *J. Am. Soc. Mass Spectrom.* 1995, 6, 229) modified for DNA. Using this approach, monoisotopic molecular weights were calculated.

Example 3

Procedure for Semi-Automated Purification of a PCR Mixture Using Commercially Available ZipTips™

For pre-treatment of ZipTips™ AX (Millipore Corp. Bedford, Mass.), the following steps were programmed to be performed by an Evolution™ P3 liquid handler (Perkin Elmer) with fluids being drawn from stock solutions in individual wells of a 96-well plate (Marshall Bioscience): loading of a rack of ZipTips™ AX; washing of ZipTips™ AX with 15 μl of 10% $NH_4OH$/50% methanol; washing of ZipTips™ AX with 15 μl of water 8 times; washing of ZipTips™ AX with 15 μl of 100 mM $NH_4OAc$.

For purification of a PCR mixture, 20 μl of crude PCR product was transferred to individual wells of a MJ Research plate using a BioHit™ multichannel pipette. Individual wells of a 96-well plate were filled with 300 μl of 40 mM NH₄HCO₃. Individual wells of a 96-well plate were filled with 300 μl of 20% methanol. An MJ research plate was filled with 10 μl of 4% NH₄OH. Two reservoirs were filled with deionized water. All plates and reservoirs were placed on the deck of the Evolution™ P3 (EP3) pipetting station in pre-arranged order. The following steps were programmed to be performed by an Evolution™ P3 pipetting station: aspiration of 20 μl of air into the EP3 P50 head; loading of a pre-treated rack of ZipTips™ AX into the EP3 P50 head; dispensation of the 20 μl NH₄HCO₃ from the ZipTips™ AX; loading of the PCR product into the ZipTips™ AX by aspiration/dispensation of the PCR solution 18 times; washing of the ZipTips™ AX containing bound nucleic acids with 15 μl of 40 mM NH₄HCO₃ 8 times; washing of the ZipTips™ AX containing bound nucleic acids with 15 μl of 20% methanol 24 times; elution of the purified nucleic acids from the ZipTips™ AX by aspiration/dispensation with 15 μl of 4% NH₄OH 18 times. For final preparation for analysis by ESI-MS, each sample was diluted 1:1 by volume with 70% methanol containing 50 mM piperidine and 50 mM imidazole.

Example 4

Procedure for Semi-Automated Purification of a PCR Mixture with Solution Capture For pre-treatment of ProPac™ WAX weak anion exchange resin, the following steps were performed in bulk: sequential washing three times (10:1 volume ratio of buffer to resin) with each of the following solutions: (1) 1.0 M formic acid/50% methanol (2) 20% methanol (3) 10% NH₄OH (4) 20% methanol (5) 40 mM NH₄HCO₃ (6) 100 mM NH₄OAc. The resin is stored in 20 mM NH₄OAc/50% methanol at 4° C.

Corning 384-well glass fiber filter plates were pre-treated with two rinses of 250 μl NH₄OH and two rinses of 100 μl NH₄HCO₃.

For binding of the PCR product nucleic acids to the resin, the following steps were programmed to be performed by the Evolution™ P3 liquid handler: addition of 0.05 to 10 μl of pre-treated ProPac™ WAX weak anion exchange resin (30 μl of a 1:60 dilution) to a 50 μl PCR reaction mixture (80 μl total volume) in a 96-well plate; mixing of the solution by aspiration/dispensation for 2.5 minutes; and transfer of the solution to a pre-treated Corning 384-well glass fiber filter plate. This step was followed by centrifugation to remove liquid from the resin and is performed manually, or under the control of a robotic arm.

The resin containing nucleic acids was then washed by rinsing three times with 200 μl of 100 mM NH₄OAc, 200 Ill of 40 mM NH₄HCO₃ with removal of buffer by centrifugation for about 15 seconds followed by rinsing three times with 20% methanol for about 15 seconds. The final rinse was followed by an extended centrifugation step (1-2 minutes).

Figure 2:
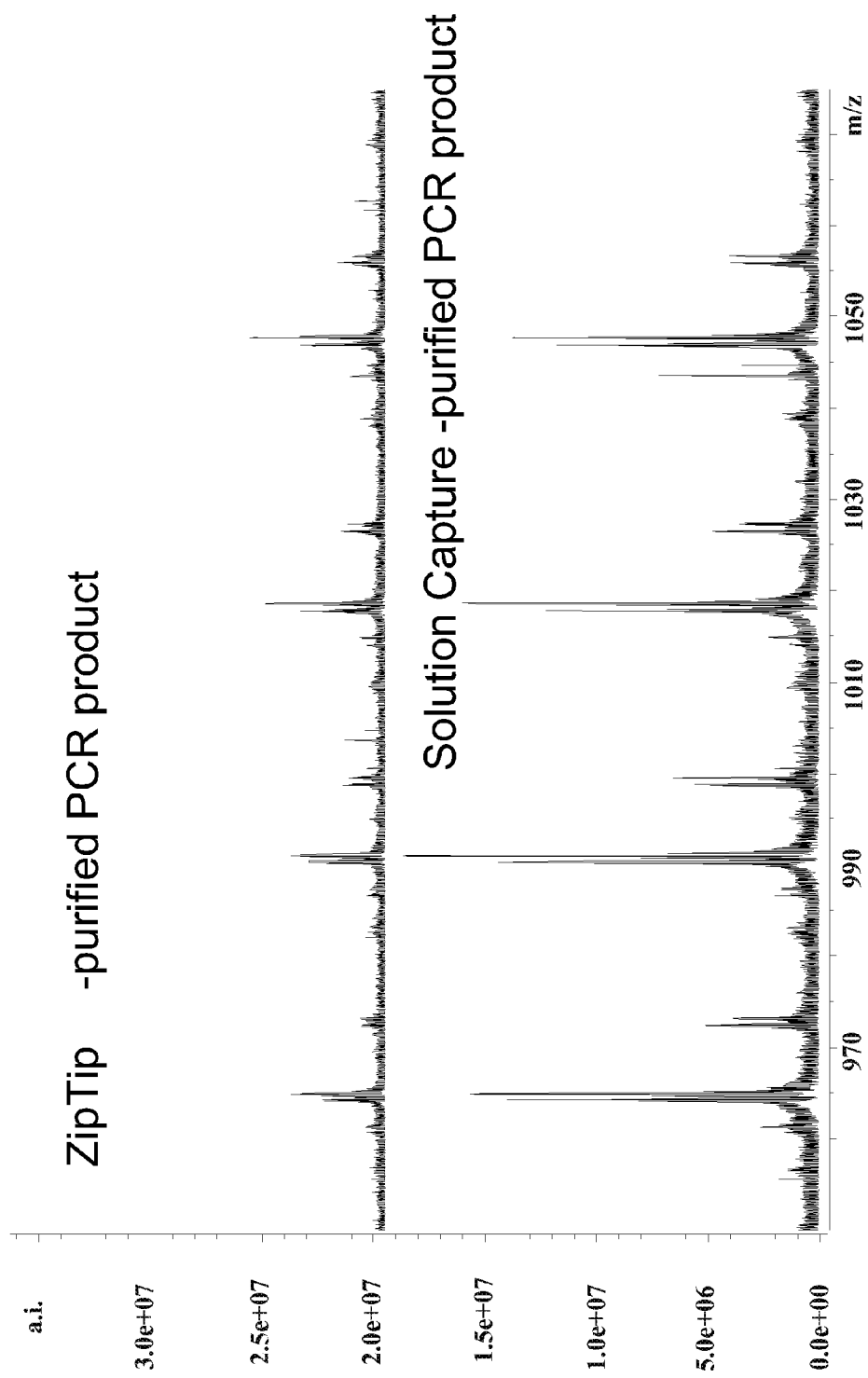
FIG. 2 is a comparison of ESI-MS spectra for purified PCR products obtained by purification with ZipTips™ (top panel) and by the solution capture purification method of the present invention. The comparison indicates that purification by the solution capture method is equally effective as the previously validated method which employs ZipTips™.

Elution of the nucleic acids from the resin was accomplished by addition of 40 μl elution/electrospray buffer (25 mM piperidine/25 mM imidazole/35% methanol and 50 nM of an internal standard oligonucleotide for calibration of mass spectrometry signals) followed by elution from the 384-well filter plate into a 384-well catch plate by centrifugation. The eluted nucleic acids in this condition were amenable to analysis by ESI-MS (See FIG. 2). The time required for purification of samples in a single 96-well plate using a liquid handler is approximately five minutes.

Example 5

Comparison of the ZipTips™ Purification method with the Solution Capture Method

To investigate the efficacy of the solution capture method of the present invention, the ESI-MS analysis results obtained for PCR products purified with the solution capture method (Example 4) were compared with the ZipTips™ method outlined in Example 3.

Bacillus anthracis DNA was isolated and amplified by PCR using a primer pair that amplifies a section of the lef gene of B. anthracis ranging from residues 756-872. Shown in FIG. 2 is a comparison of ESI-MS spectra for purified PCR products obtained by purification with ZipTips™ (top panel) and by the solution capture purification method of the present invention. The comparison indicates that purification by the solution capture method is equally effective as the previously validated method which employs ZipTips™. However, purification by solution capture represents a significant cost savings and is more efficient. As stated by Jiang and Hofstadler, purification of PCR products using ZipTips™ "yields an ESI-compatible sample (96-well plate) in less than 20 minutes." The solution capture method of the present invention yields an ESI-compatible sample in approximately five minutes. The retail cost of the current procedure using a pipette tip packed with anion exchange resin exemplified by ZipTip™ AX (Millipore, Bedford, Mass.) is approximately $1.77 per pipette tip (for each sample). The estimated cost of solution capture of PCR products is $0.10 per sample and takes into account the combination of anion exchange resin and filter plate.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety. U.S. provisional application Ser. No. 60/470,547 filed May 13, 2003 is incorporated herein by reference in its entirety.

What is claimed is:

1. A method of purifying a solution comprising nucleic acids for mass spectrometry analysis comprising:

mixing said solution comprising nucleic acids with one or more magnetic beads linked to at least one anion exchange functional group having a pKa of 9 or greater to yield a suspension of said one or more magnetic beads in said solution wherein said nucleic acids bind to said at least one anion exchange functional group linked to said one or more magnetic beads;

isolating said one or more magnetic beads from said solution by application of a magnetic field;

removing said solution from said one or more magnetic beads;

washing said one or more magnetic beads to remove one or more contaminants with one or more wash buffers while said nucleic acids are bound to said at least one anion exchange functional group linked to said one or more magnetic beads; and eluting said nucleic acids from said at least one anion exchange functional group linked to said one or more magnetic beads with an elution buffer compatible with electrospray ionization mass spectrometry wherein said elution buffer does not comprise a metal cation salt.

2. The method of claim 1 further comprising analyzing said nucleic acids by mass spectrometry.

3. The method of claim 1 wherein said mixing, washing, and eluting steps are performed by a liquid handler.

4. The method of claim 1 wherein said mixing, washing, isolating, and eluting steps are performed by a robot.

5. The method of claim 1 wherein said mixing is accomplished by pipetting, vortexing, sonication, or shaking.

6. The method of claim 1 wherein said one or more wash buffers comprises ammonium acetate.

7. The method of claim 1 wherein said one or more wash buffers comprises ammonium bicarbonate.

8. The method of claim 1 wherein said one or more wash buffers comprises methanol.

9. The method of claim 1 wherein said elution buffer comprises ammonium hydroxide.

10. The method of claim 1 wherein said elution buffer comprises piperidine, imidazole and methanol.

11. The method of claim 1 wherein said nucleic acids are the products of a nucleic acid amplification reaction.

12. The method of claim 11 wherein said nucleic acid amplification reaction is selected from the group consisting of polymerase chain reaction, ligase chain reaction or strand displacement amplification reaction.

13. The method of claim 1 wherein said one or more contaminants is selected from the group consisting of buffer additives, salts, detergents, polymers, stabilizers, metal cations, proteins and deoxynucleotide triphosphates.

14. The method of claim 6 wherein said one or more wash buffers comprise 50 mM to 200 mM ammonium acetate.

15. The method of claim 7 wherein said one or more wash buffer comprise 50 mM to 200 mM ammonium bicarbonate.

16. The method of claim 8 wherein said one or more wash buffer comprise 20% to 50% methanol.

17. The method of claim 9 wherein said elution buffer comprises 2% to 6% ammonium hydroxide.

18. The method of claim 10 wherein said elution buffer comprises 10 mM to 50 mM piperidine, 10 mM to 50 mM imidazole, and methanol.

19. The method of claim 18 wherein said methanol is selected from the group consisting of 30% methanol and 35% methanol.

20. The method of claim 18 wherein said elution buffer comprises 25 mM piperidine, 25 mM imidazole, and methanol.

21. The method of claim 20 wherein said methanol is selected from the group consisting of 30% methanol and 35% methanol.

22. The method of claim 1, wherein said anion exchange functional group is polyethyleneimine.

23. The method of claim 1, wherein said anion exchange functional group is a diethylaminomethyl.

24. The method of claim 1, wherein said anion exchange functional group is a diethylaminoethyl.

* * * * *